(12) United States Patent
Ashman et al.

(10) Patent No.: US 7,807,788 B2
(45) Date of Patent: Oct. 5, 2010

(54) CHIMERIC AND HUMANISED MONOCLONAL ANTIBODIES AGAINST INTERLEUKIN-13

(75) Inventors: Claire Ashman, King of Prussia, PA (US); Martin John Cassidy, Stevenage (GB); Jonathan Henry Ellis, Stevenage (GB); Trevor Anthony Kenneth Wattam, Stevenage (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 11/570,736

(22) PCT Filed: Jun. 30, 2005

(86) PCT No.: PCT/GB2005/002581
§ 371 (c)(1),
(2), (4) Date: Dec. 15, 2006

(87) PCT Pub. No.: WO2006/003407
PCT Pub. Date: Jan. 12, 2006

(65) Prior Publication Data
US 2007/0258979 A1  Nov. 8, 2007

(30) Foreign Application Priority Data
Jul. 1, 2004 (GB) ................... 0414799.7
Oct. 25, 2004 (GB) ................... 0423675.8

(51) Int. Cl.
*C07K 16/00* (2006.01)
*C12P 21/00* (2006.01)
(52) U.S. Cl. ................... 530/387.1; 530/387.3
(58) Field of Classification Search ........... None
See application file for complete search history.

(56) References Cited

U.S. PATENT DOCUMENTS 6,468,528 B1  10/2002  Mak et al. ............. 424/130.1

| | | | |
|---|---|---|---|
| 2003/0235555 A1 | | 12/2003 | Shealey et al. ............. 424/85.1 |
| 2004/0126372 A1 | * | 7/2004 | Banerjee et al. ........... 424/145.1 |
| 2005/0065327 A1 | * | 3/2005 | Monk et al. ............. 530/388.23 |
| 2005/0239140 A1 | * | 10/2005 | O'neil et al. ................. 435/7.1 |
| 2006/0063228 A1 | * | 3/2006 | Kasaian et al. ............. 435/69.1 |

FOREIGN PATENT DOCUMENTS

WO  WO 03/092610 A  11/2003
WO  WO 2005/007699 A  1/2005

OTHER PUBLICATIONS

Punnonen et al. (J. Allergy & Clin. Immunol. 100(6)792-801 (1997)).*
Fundamental Immunology, William E. Paul M.D., ed., 3rd Ed., pp. 292-295, 1993.*
Rudikoff et al. Proc. Natl. Acad. Sci. USA, 79(6):1979-1983, Mar. 1982.*
Colman P. M. Research in Immunology, 145:33-36, 1994.*
MacCallum et al. J. Mol. Biol., 262, 732-745, 1996.*
Casset et al. Biochemical and Biophysical Research Communications, 307:198-205, 2003.*
Punnonen et al. *Journal of Allergy & Clinical Immunology*, 100(6): 792-801 (1997).
Fichtner, et al., Journal of Immunology, 178:5859-5870, 2007.
Fichtner, et al., Nature Medicine, vol. 12, No. 1, Jan. 2006, pp. 99-106.
Hu, et al., Cancer Research, 56, 3055-3061, Jul. 1, 1996.
Pack, et al., Biochemistry, 31, 1579-1584, Feb. 18, 1992.
McKenzie, et al., PNAS, vol. 901 pp. 3735-3739, Apr. 1993.

* cited by examiner

*Primary Examiner*—Larry R Helms
*Assistant Examiner*—Hong Sang
(74) *Attorney, Agent, or Firm*—Jonathan M. Dermott; William T. Han

(57) ABSTRACT

The present invention concerns immunoglobulins, particularly antibodies which specifically bind human Interleukin 13 (hIL-13). Antibodies of the invention may be used in the treatment of a variety of diseases or disorders responsive to modulation of the interaction between hIL-13 and the human IL-13 receptor. Such diseases include severe asthma, atopic dermatitis, COPD and various fibrotic diseases. Pharmaceutical compositions comprising said antibodies and methods of manufacture are also disclosed.

21 Claims, 28 Drawing Sheets

SEQUENCE LISTING

```
<160> NUMBER OF SEQ ID NOS: 137

<210> SEQ ID NO 1
<211> LENGTH: 9
<212> TYPE: PRT
<213> ORGANISM: Homo sapiens

<400> SEQUENCE: 1

Phe Tyr Ile Lys Asp Thr Tyr Met His
1               5

<210> SEQ ID NO 2
<211> LENGTH: 17
<212> TYPE: PRT
<213> ORGANISM: Homo sapiens

<400> SEQUENCE: 2

Thr Ile Asp Pro Ala Asn Gly Asn Thr Lys Tyr Val Pro Lys Phe Gln
1               5                   10                  15

Gly

<210> SEQ ID NO 3
<211> LENGTH: 16
<212> TYPE: PRT
<213> ORGANISM: Homo sapiens

<400> SEQUENCE: 3

Ser Ile Tyr Asp Asp Tyr His Tyr Asp Tyr Tyr Ala Met Asp Tyr
1               5                   10                  15

<210> SEQ ID NO 4
<211> LENGTH: 16
<212> TYPE: PRT
<213> ORGANISM: Homo sapiens

<400> SEQUENCE: 4

Arg Ser Ser Gln Asn Ile Val His Ile Asn Gly Asn Thr Tyr Leu Glu
1               5                   10                  15

<210> SEQ ID NO 5
<211> LENGTH: 7
<212> TYPE: PRT
<213> ORGANISM: Homo sapiens

<400> SEQUENCE: 5

Lys Ile Ser Asp Arg Phe Ser
1               5

<210> SEQ ID NO 6
<211> LENGTH: 9
```

```
<212> TYPE: PRT
<213> ORGANISM: Homo sapiens

<400> SEQUENCE: 6

Phe Gln Gly Ser His Val Pro Trp Thr
1               5

<210> SEQ ID NO 7
<211> LENGTH: 125
<212> TYPE: PRT
<213> ORGANISM: Homo sapiens

<400> SEQUENCE: 7

Glu Ile Gln Leu Gln Gln Ser Val Ala Glu Leu Val Arg Pro Gly Ala
1               5                   10                  15

Ser Val Arg Leu Ser Cys Thr Ala Ser Gly Phe Tyr Ile Lys Asp Thr
            20                  25                  30

Tyr Met His Trp Val Ile Gln Arg Pro Glu Gln Gly Leu Glu Trp Ile
        35                  40                  45

Gly Thr Ile Asp Pro Ala Asn Gly Asn Thr Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Arg Leu Ser Ser Leu Thr Ser Glu Asp Thr Ala Ile Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Ser Val Thr Val Ser Ser
        115                 120                 125

<210> SEQ ID NO 8
<211> LENGTH: 112
<212> TYPE: PRT
<213> ORGANISM: Homo sapiens

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ile
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Ile Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 9
<211> LENGTH: 112
<212> TYPE: PRT
<213> ORGANISM: Homo sapiens

<400> SEQUENCE: 9

Gly Pro Val Pro Pro Ser Thr Ala Leu Arg Glu Leu Ile Glu Glu Leu
1               5                   10                  15
```

```
Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu His Leu Lys Lys Leu Phe Arg Glu Gly Arg Phe Asn
                100                 105                 110
```

<210> SEQ ID NO 10
<211> LENGTH: 339
<212> TYPE: DNA
<213> ORGANISM: Homo sapiens

<400> SEQUENCE: 10

```
ggccctgtgc ctccctctac agccctcagg gagctcattg aggagctggt caacatcacc      60
cagaaccaga aggctccgct ctgcaatggc agcatggtat ggagcatcaa cctgacagct     120
ggcatgtact gtgcagccct ggaatccctg atcaacgtgt caggctgcag tgccatcgag     180
aagacccaga ggatgctgag cggattctgc ccgcacaagg tctcagctgg cagttttcc     240 agcttgcatg tccgagacac caaaatcgag gtggcccagt ttgtaaagga cctgctctta     300
catttaaaga aactttttcg cgagggacgg ttcaactga                            339
```

<210> SEQ ID NO 11
<211> LENGTH: 125
<212> TYPE: PRT
<213> ORGANISM: Homo sapiens

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
                100                 105                 110

Asp Tyr Trp Gly Gln Gly Thr Leu Val Thr Val Ser Ser
                115                 120                 125
```

<210> SEQ ID NO 12
<211> LENGTH: 125
<212> TYPE: PRT
<213> ORGANISM: Homo sapiens

<400> SEQUENCE: 12

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Ile Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser
            115                 120                 125

<210> SEQ ID NO 13
<211> LENGTH: 125
<212> TYPE: PRT
<213> ORGANISM: Homo sapiens

<400> SEQUENCE: 13

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Ile Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser
            115                 120                 125

<210> SEQ ID NO 14
<211> LENGTH: 125
<212> TYPE: PRT
<213> ORGANISM: Homo sapiens

<400> SEQUENCE: 14

Gln Val Gln Leu Val Gln Ser Gly Ala Glu Val Lys Lys Pro Gly Ser
 1               5                  10                  15

Ser Val Arg Val Ser Cys Lys Ala Ser Gly Phe Tyr Ile Lys Asp Thr
            20                  25                  30

Tyr Met His Trp Val Ile Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Thr Ser Thr Ser Thr Ala Tyr
65                  70                  75                  80
```

```
Met Arg Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser
        115                 120                 125
```

<210> SEQ ID NO 15
<211> LENGTH: 112
<212> TYPE: PRT
<213> ORGANISM: Homo sapiens

<400> SEQUENCE: 15

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ile
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Ile Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Phe Gln Gly
                85                  90                  95

Ser His Val Pro Trp Thr Phe Gly Gln Gly Thr Lys Leu Glu Ile Lys
            100                 105                 110
```

<210> SEQ ID NO 16
<211> LENGTH: 112
<212> TYPE: PRT
<213> ORGANISM: Homo sapiens

<400> SEQUENCE: 16

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ile
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Ile Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Phe Gln Gly
                85                  90                  95

Ser His Val Pro Trp Thr Phe Gly Gln Gly Thr Lys Leu Glu Ile Lys
            100                 105                 110
```

<210> SEQ ID NO 17
<211> LENGTH: 19
<212> TYPE: PRT
<213> ORGANISM: Homo sapiens

<400> SEQUENCE: 17

```
Met Gly Trp Ser Cys Ile Ile Leu Phe Leu Val Ala Thr Ala Thr Gly
1               5                   10                  15

Val His Ser
```

<210> SEQ ID NO 18
<211> LENGTH: 455
<212> TYPE: PRT
<213> ORGANISM: Homo sapiens

<400> SEQUENCE: 18

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Tyr Asp Asp Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
```

```
                370                 375                 380
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
                450                 455

<210> SEQ ID NO 19
<211> LENGTH: 455
<212> TYPE: PRT
<213> ORGANISM: Homo sapiens

<400> SEQUENCE: 19

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
                20                  25                  30

Tyr Met His Trp Val Ile Gln Ala Pro Gly Gln Gly Leu Glu Trp Met
                35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285
```

-continued

```
Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 20
<211> LENGTH: 455
<212> TYPE: PRT
<213> ORGANISM: Homo sapiens

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Ile Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

```
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 21
<211> LENGTH: 455
<212> TYPE: PRT
<213> ORGANISM: Homo sapiens

<400> SEQUENCE: 21

Gln Val Gln Leu Val Gln Ser Gly Ala Glu Val Lys Lys Pro Gly Ser
1               5                   10                  15
Ser Val Arg Val Ser Cys Lys Ala Ser Gly Phe Tyr Ile Lys Asp Thr
            20                  25                  30
Tyr Met His Trp Val Ile Gln Ala Pro Gly Gln Gly Leu Glu Trp Met
        35                  40                  45
Gly Thr Ile Asp Pro Ala Asn Gly Asn Thr Lys Tyr Val Pro Lys Phe
    50                  55                  60
Gln Gly Arg Val Thr Ile Thr Ala Asp Thr Ser Thr Ser Thr Ala Tyr
65                  70                  75                  80
Met Arg Leu Ser Ser Leu Arg Ser Glu Asp Thr Ala Val Tyr Tyr Cys
                85                  90                  95
Ala Arg Ser Ile Tyr Asp Asp Tyr His Tyr Asp Asp Tyr Tyr Ala Met
            100                 105                 110
Asp Tyr Trp Gly Gln Gly Thr Leu Val Thr Val Ser Ser Ala Ser Thr
```

-continued

```
                115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Leu Gly Thr Gln Thr Tyr Ile Cys
            195                 200                 205
Asn Val Asn His Lys Pro Ser Asn Thr Lys Val Asp Lys Lys Val Glu
        210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 22
<211> LENGTH: 219
<212> TYPE: PRT
<213> ORGANISM: Homo sapiens

<400> SEQUENCE: 22

Asp Ile Val Met Thr Gln Ser Pro Leu Ser Leu Pro Val Thr Pro Gly
  1               5                  10                  15
Glu Pro Ala Ser Ile Ser Cys Arg Ser Ser Gln Asn Ile Val His Ile
                20                  25                  30
```

Asn Gly Asn Thr Tyr Leu Glu Trp Tyr Leu Gln Lys Pro Gly Gln Ser
            35                  40                  45

Pro Arg Leu Leu Ile Tyr Lys Ile Ser Asp Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Ile Tyr Tyr Cys Phe Gln Gly
                 85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 23
<211> LENGTH: 219
<212> TYPE: PRT
<213> ORGANISM: Homo sapiens

<400> SEQUENCE: 23

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Asn Ile Val His Ile
            20                  25                  30

Asn Gly Asn Thr Tyr Leu Glu Trp Tyr Leu Gln Lys Pro Gly Gln Ser
            35                  40                  45

Pro Arg Leu Leu Ile Tyr Lys Ile Ser Asp Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Phe Gln Gly
                 85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 24
<211> LENGTH: 375
<212> TYPE: DNA
<213> ORGANISM: Homo sapiens

<400> SEQUENCE: 24
gaaattcagc tgcagcagtc tgtggcagaa cttgtgaggc caggggcctc agtcaggttg      60
tcctgcacag cttctggctt ctacattaaa gacacctata tgcactgggt gattcagagg     120
cctgaacagg gcctggagtg gattggaacg attgatcctg cgaatggtaa tactaaatat     180
gtcccgaagt tccagggcaa ggccactata actgcagaca catcctccaa cacagcctac     240
ctgcggctca gcagcctgac atctgaggac actgccatct attactgtgc tagaagcatc     300
tatgatgatt accactacga cgattactat gctatggact actggggtca aggaaccctca    360
gtcaccgtct cctca                                                      375

<210> SEQ ID NO 25
<211> LENGTH: 336
<212> TYPE: DNA
<213> ORGANISM: Homo sapiens

<400> SEQUENCE: 25
gatgttttga tgacccaaac tccactctcc ctgcctgtca gtcttggaga tcaagcctcc      60
atctcttgca gatctagtca gaacattgta catattaatg aaacacccta tttagaatgg     120
taccttcaga aaccaggcca gtctccaaag ctcctgatct acaaaattc cgaccgattt     180
tctggggtcc cagacaggtt cagtggcagt ggatcaggga cagatttcac gctcaagatc     240
agcagagtgg aggctgagga tctgggagtt tattactgct ttcaaggttc acatgttccg     300
tggacgttcg gtggaggcac caagctggaa atcaaa                               336

<210> SEQ ID NO 26
<211> LENGTH: 375
<212> TYPE: DNA
<213> ORGANISM: Homo sapiens

<400> SEQUENCE: 26
caggtgcagc tggtgcagtc tggggctgag gtgaagaagc ctgggtcctc ggtgaaggtc      60
tcctgcaagg cttctggatt ctacattaaa gacacctata tgcactgggt gcgacaggcc     120
cctggacaag ggcttgagtg gatgggaacg attgatcctg cgaatggtaa tactaaatat     180
gtcccgaagt tccagggcag agtcacgatt accgcggacg aatccacgag cacagcctac     240
atggagctga gcagcctgag atctgaggac acggccgtgt attactgtgc gagaagcatc     300
tatgatgatt accactacga cgattactat gctatggact actggggcca agggacacta     360
gtcaccgtct cctca                                                      375

<210> SEQ ID NO 27
<211> LENGTH: 375
<212> TYPE: DNA
<213> ORGANISM: Homo sapiens

<400> SEQUENCE: 27

```
caggtgcagc tggtgcagtc tggggctgag gtgaagaagc ctgggtcctc ggtgaaggtc      60
tcctgcaagg cttctggatt ctacattaaa gacacctata tgcactgggt gatacaggcc     120
cctggacaag ggcttgagtg gatgggaacg attgatcctg cgaatggtaa tactaaatat     180
gtcccgaagt tccagggcag agtcacgatt accgcggacg aatccacgag cacagcctac     240
atggagctga gcagcctgag atctgaggac acggccgtgt attactgtgc gagaagcatc     300
tatgatgatt accactacga cgattactat gctatggact actggggcca agggacacta     360
gtcaccgtct cctca                                                      375

<210> SEQ ID NO 28
<211> LENGTH: 375
<212> TYPE: DNA
<213> ORGANISM: Homo sapiens

<400> SEQUENCE: 28
caggtgcagc tggtgcagtc tggggctgag gtgaagaagc ctgggtcctc ggtgaaggtc      60
tcctgcaagg cttctggatt ctacattaaa gacacctata tgcactgggt gatacaggcc     120
cctggacaag ggcttgagtg gatgggaacg attgatcctg cgaatggtaa tactaaatat     180
gtcccgaagt tccagggcag agtcacgatt accgcggaca catccacgag cacagcctac     240
atggagctga gcagcctgag atctgaggac acggccgtgt attactgtgc gagaagcatc     300
tatgatgatt accactacga cgattactat gctatggact actggggcca agggacacta     360
gtcaccgtct cctca                                                      375

<210> SEQ ID NO 29
<211> LENGTH: 375
<212> TYPE: DNA
<213> ORGANISM: Homo sapiens

<400> SEQUENCE: 29
caggtgcagc tggtgcagtc tggggctgag gtgaagaagc ctgggtcctc ggtgagggtc      60
tcctgcaagg cttctggatt ctacattaaa gacacctata tgcactgggt gatacaggcc     120
cctggacaag ggcttgagtg gatgggaacg attgatcctg cgaatggtaa tactaaatat     180
gtcccgaagt tccagggcag agtcacgatt accgcggaca catccacgag cacagcctac     240
atgaggctga gcagcctgag atctgaggac acggccgtgt attactgtgc gagaagcatc     300
tatgatgatt accactacga cgattactat gctatggact actggggcca agggacacta     360
gtcaccgtct cctca                                                      375

<210> SEQ ID NO 30
<211> LENGTH: 336
<212> TYPE: DNA
<213> ORGANISM: Homo sapiens

<400> SEQUENCE: 30
gatattgtga tgactcagtc tccactctcc ctgcccgtca cccctggaga gccggcctcc      60
atctcctgca gatctagtca gaacattgta catattaatg aaacacccta tttagaatgg     120
tacctgcaga agccagggca gtctccacgg ctcttgatct ataaaatttc cgaccgattt     180
tctggggtcc ctgacaggtt cagtggcagt ggatcaggca cagatttac attgaaaatc     240 agcagagtgg aggctgacga tgttggaatt tattactgct ttcaaggttc acatgttccg     300
tggacgtttg gccaggggac caagctggag atcaag                               336
```

<210> SEQ ID NO 31
<211> LENGTH: 336
<212> TYPE: DNA
<213> ORGANISM: Homo sapiens

<400> SEQUENCE: 31

| | | | | | |
|---|---|---|---|---|---|
| gatattgtga | tgactcagtc | tccactctcc | ctgcccgtca | cccctggaga | gccggcctcc | 60 |
| atctcctgca | gatctagtca | gaacattgta | catattaatg | gaaacaccta | tttagaatgg | 120 |
| tacctgcaga | agccagggca | gtctccacgg | ctcttgatct | ataaatttc | cgaccgattt | 180 |
| tctggggtcc | ctgacaggtt | cagtggcagt | ggatcaggca | cagattttac | attgaaaatc | 240 |
| agcagagtgg | aggctgacga | tgttggagtt | tattactgct | ttcaaggttc | acatgttccg | 300 |
| tggacgtttg | gccaggggac | caagctggag | atcaag | | | 336 |

<210> SEQ ID NO 32
<211> LENGTH: 1368
<212> TYPE: DNA
<213> ORGANISM: Homo sapiens

<400> SEQUENCE: 32

| | | | | | |
|---|---|---|---|---|---|
| caggtgcagc | tggtgcagtc | tggggctgag | gtgaagaagc | ctgggtcctc | ggtgaaggtc | 60 |
| tcctgcaagg | cttctggatt | ctacattaaa | gacaccctata | tgcactgggt | gcgacaggcc | 120 |
| cctggacaag | ggcttgagtg | gatgggaacg | attgatcctg | cgaatggtaa | tactaaatat | 180 |
| gtcccgaagt | tccagggcag | agtcacgatt | accgcggacg | aatccacgag | cacagcctac | 240 |
| atggagctga | gcagcctgag | atctgaggac | acggccgtgt | attactgtgc | gagaagcatc | 300 |
| tatgatgatt | accactacga | cgattactat | gctatggact | actggggcca | agggacacta | 360 |
| gtcacagtct | cctcagcctc | caccaagggc | ccatcggtct | tccccctggc | accctcctcc | 420 |
| aagagcacct | ctgggggcac | agcggccctg | ggctgcctgg | tcaaggacta | cttccccgaa | 480 |
| ccggtgacgg | tgtcgtggaa | ctcaggcgcc | ctgaccagcg | gcgtgcacac | cttcccggct | 540 |
| gtcctacagt | cctcaggact | ctactccctc | agcagcgtgg | tgaccgtgcc | ctccagcagc | 600 |
| ttgggcaccc | agacctacat | ctgcaacgtg | aatcacaagc | ccagcaacac | caaggtggac | 660 |
| aagaaagttg | agcccaaatc | ttgtgacaaa | actcacacat | gcccaccgtg | cccagcacct | 720 |
| gaactcctgg | ggggaccgtc | agtcttcctc | ttccccccaa | aacccaagga | caccctcatg | 780 |
| atctcccgga | cccctgaggt | cacatgcgtg | gtggtggacg | tgagccacga | agaccctgag | 840 |
| gtcaagttca | actggtacgt | ggacggcgtg | gaggtgcata | atgccaagac | aaagccgcgg | 900 |
| gaggagcagt | acaacagcac | gtaccgtgtg | gtcagcgtcc | tcaccgtcct | gcaccaggac | 960 |
| tggctgaatg | gcaaggagta | caagtgcaag | gtctccaaca | aagccctccc | agcccccatc | 1020 |
| gagaaaacca | tctccaaagc | caaagggcag | ccccgagaac | cacaggtgta | caccctgccc | 1080 |
| ccatcccggg | atgagctgac | caagaaccag | gtcagcctga | cctgcctggt | caaaggcttc | 1140 |
| tatcccagcg | acatcgccgt | ggagtgggag | agcaatgggc | agccggagaa | caactacaag | 1200 |
| accacgcctc | ccgtgctgga | ctccgacggc | tccttcttcc | tctacagcaa | gctcaccgtg | 1260 |
| gacaagagca | ggtggcagca | ggggaacgtc | ttctcatgct | ccgtgatgca | tgaggctctg | 1320 |
| cacaaccact | acacgcagaa | gagcctctcc | ctgtctccgg | gtaaatga | | 1368 |

<210> SEQ ID NO 33
<211> LENGTH: 1368
<212> TYPE: DNA
<213> ORGANISM: Homo sapiens

<400> SEQUENCE: 33

```
caggtgcagc tggtgcagtc tggggctgag gtgaagaagc ctgggtcctc ggtgaaggtc      60
tcctgcaagg cttctggatt ctacattaaa gacacctata tgcactgggt gatacaggcc     120
cctggacaag ggcttgagtg gatgggaacg attgatcctg cgaatggtaa tactaaatat    180
gtcccgaagt tccagggcag agtcacgatt accgcggacg aatccacgag cacagcctac     240
atggagctga gcagcctgag atctgaggac acggccgtgt attactgtgc gagaagcatc     300
tatgatgatt accactacga cgattactat gctatggact actggggcca agggacacta     360
gtcacagtct cctcagcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa acccaaggac accctcatg      780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagggcag ccccgagaac cacaggtgta caccctgccc    1080
ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaatga                 1368
```

<210> SEQ ID NO 34
<211> LENGTH: 1368
<212> TYPE: DNA
<213> ORGANISM: Homo sapiens

<400> SEQUENCE: 34

```
caggtgcagc tggtgcagtc tggggctgag gtgaagaagc ctgggtcctc ggtgaaggtc      60
tcctgcaagg cttctggatt ctacattaaa gacacctata tgcactgggt gatacaggcc     120
cctggacaag ggcttgagtg gatgggaacg attgatcctg cgaatggtaa tactaaatat     180
gtcccgaagt tccagggcag agtcacgatt accgcggaca catccacgag cacagcctac     240
atggagctga gcagcctgag atctgaggac acggccgtgt attactgtgc gagaagcatc     300
tatgatgatt accactacga cgattactat gctatggact actggggcca agggacacta     360
gtcacagtct cctcagcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
```

```
gaactcctgg ggggaccgtc agtcttcctc ttccccccaa acccaagga caccctcatg     780 atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagggcag ccccgagaac acaggtgta caccctgccc    1080 ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaatga                 1368

<210> SEQ ID NO 35
<211> LENGTH: 1368
<212> TYPE: DNA
<213> ORGANISM: Homo sapiens

<400> SEQUENCE: 35
caggtgcagc tggtgcagtc tggggctgag gtgaagaagc ctgggtcctc ggtgagggtc      60
tcctgcaagg cttctggatt ctacattaaa gacacctata tgcactgggt gatacaggcc     120
cctggacaag ggcttgagtg gatgggaacg attgatcctg cgaatggtaa tactaaatat     180
gtcccgaagt tccagggcag agtcacgatt accgcggaca catccacgag cacagcctac     240
atgaggctga gcagcctgag atctgaggac acggccgtgt attactgtgc gagaagcatc     300
tatgatgatt accactacga cgattactat gctatggact actggggcca aggacacta     360 gtcacagtct cctcagcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa acccaaggac accctcatg     780 atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagggcag ccccgagaac acaggtgta caccctgccc    1080 ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaatga                 1368

<210> SEQ ID NO 36
```

```
<211> LENGTH: 660
<212> TYPE: DNA
<213> ORGANISM: Homo sapiens

<400> SEQUENCE: 36
gatattgtga tgactcagtc tccactctcc ctgcccgtca cccctggaga gccggcctcc      60
atctcctgca gatctagtca gaacattgta catattaatg gaaacaccta tttagaatgg     120
tacctgcaga agccagggca gtctccacgg ctcttgatct ataaaatttc cgaccgattt     180
tctggggtcc ctgacaggtt cagtggcagt ggatcaggca cagattttac attgaaaatc     240
agcagagtgg aggctgacga tgttggaatt tattactgct ttcaaggttc acatgttccg     300
tggacgtttg gccaggggac caagctggag atcaagcgta cggtggctgc accatctgtc     360
ttcatcttcc cgccatctga tgagcagttg aaatctggaa ctgcctctgt tgtgtgcctg     420
ctgaataact ctatcccag agaggccaaa gtacagtgga aggtggacaa cgccctccaa      480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct caacagggg agagtgttag      660

<210> SEQ ID NO 37
<211> LENGTH: 660
<212> TYPE: DNA
<213> ORGANISM: Homo sapiens

<400> SEQUENCE: 37
gatattgtga tgactcagtc tccactctcc ctgcccgtca cccctggaga gccggcctcc      60
atctcctgca gatctagtca gaacattgta catattaatg gaaacaccta tttagaatgg     120
tacctgcaga agccagggca gtctccacgg ctcttgatct ataaaatttc cgaccgattt     180
tctggggtcc ctgacaggtt cagtggcagt ggatcaggca cagattttac attgaaaatc     240
agcagagtgg aggctgacga tgttggagtt tattactgct ttcaaggttc acatgttccg     300
tggacgtttg gccaggggac caagctggag atcaagcgta cggtggctgc accatctgtc     360
ttcatcttcc cgccatctga tgagcagttg aaatctggaa ctgcctctgt tgtgtgcctg     420
ctgaataact ctatcccag agaggccaaa gtacagtgga aggtggacaa cgccctccaa      480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct caacagggg agagtgttag      660

<210> SEQ ID NO 38
<211> LENGTH: 20
<212> TYPE: PRT
<213> ORGANISM: Homo sapiens

<400> SEQUENCE: 38

Ser Gly Ser Gly Pro Ser Thr Ala Leu Arg Glu Leu Ile Glu Glu Leu
1               5                   10                  15

Val Asn Ile Thr
            20

<210> SEQ ID NO 39
<211> LENGTH: 20
<212> TYPE: PRT
<213> ORGANISM: Homo sapiens

<400> SEQUENCE: 39
```

```
Ser Gly Ser Gly Leu Arg Glu Leu Ile Glu Glu Leu Val Asn Ile Thr
1               5                   10                  15

Gln Asn Gln Lys
            20

<210> SEQ ID NO 40
<211> LENGTH: 20
<212> TYPE: PRT
<213> ORGANISM: Homo sapiens

<400> SEQUENCE: 40

Ser Gly Ser Gly Ile Glu Glu Leu Val Asn Ile Thr Gln Asn Gln Lys
1               5                   10                  15

Ala Pro Leu Cys
            20

<210> SEQ ID NO 41
<211> LENGTH: 20
<212> TYPE: PRT
<213> ORGANISM: Homo sapiens

<400> SEQUENCE: 41

Ser Gly Ser Gly Val Asn Ile Thr Gln Asn Gln Lys Ala Pro Leu Cys
1               5                   10                  15

Asn Gly Ser Met
            20

<210> SEQ ID NO 42
<211> LENGTH: 20
<212> TYPE: PRT
<213> ORGANISM: Homo sapiens

<400> SEQUENCE: 42

Ser Gly Ser Gly Gln Asn Gln Lys Ala Pro Leu Cys Asn Gly Ser Met
1               5                   10                  15

Val Trp Ser Ile
            20

<210> SEQ ID NO 43
<211> LENGTH: 20
<212> TYPE: PRT
<213> ORGANISM: Homo sapiens

<400> SEQUENCE: 43

Ser Gly Ser Gly Ala Pro Leu Cys Asn Gly Ser Met Val Trp Ser Ile
1               5                   10                  15

Asn Leu Thr Ala
            20

<210> SEQ ID NO 44
<211> LENGTH: 20
<212> TYPE: PRT
<213> ORGANISM: Homo sapiens

<400> SEQUENCE: 44

Ser Gly Ser Gly Asn Gly Ser Met Val Trp Ser Ile Asn Leu Thr Ala
1               5                   10                  15

Gly Met Tyr Cys
            20

<210> SEQ ID NO 45
```

-continued

<211> LENGTH: 20
<212> TYPE: PRT
<213> ORGANISM: Homo sapiens

<400> SEQUENCE: 45

Ser Gly Ser Gly Val Trp Ser Ile Asn Leu Thr Ala Gly Met Tyr Cys
1               5                   10                  15

Ala Ala Leu Glu
            20

<210> SEQ ID NO 46
<211> LENGTH: 20
<212> TYPE: PRT
<213> ORGANISM: Homo sapiens

<400> SEQUENCE: 46

Ser Gly Ser Gly Asn Leu Thr Ala Gly Met Tyr Cys Ala Ala Leu Glu
1               5                   10                  15

Ser Leu Ile Asn
            20

<210> SEQ ID NO 47
<211> LENGTH: 20
<212> TYPE: PRT
<213> ORGANISM: Homo sapiens

<400> SEQUENCE: 47

Ser Gly Ser Gly Gly Met Tyr Cys Ala Ala Leu Glu Ser Leu Ile Asn
1               5                   10                  15

Val Ser Gly Cys
            20

<210> SEQ ID NO 48
<211> LENGTH: 20
<212> TYPE: PRT
<213> ORGANISM: Homo sapiens

<400> SEQUENCE: 48

Ser Gly Ser Gly Ala Ala Leu Glu Ser Leu Ile Asn Val Ser Gly Cys
1               5                   10                  15

Ser Ala Ile Glu
            20

<210> SEQ ID NO 49
<211> LENGTH: 20
<212> TYPE: PRT
<213> ORGANISM: Homo sapiens

<400> SEQUENCE: 49

Ser Gly Ser Gly Ser Leu Ile Asn Val Ser Gly Cys Ser Ala Ile Glu
1               5                   10                  15

Lys Thr Gln Arg
            20

<210> SEQ ID NO 50
<211> LENGTH: 20
<212> TYPE: PRT
<213> ORGANISM: Homo sapiens

<400> SEQUENCE: 50

Ser Gly Ser Gly Val Ser Gly Cys Ser Ala Ile Glu Lys Thr Gln Arg
1               5                   10                  15

```
Met Leu Ser Gly
        20

<210> SEQ ID NO 51
<211> LENGTH: 20
<212> TYPE: PRT
<213> ORGANISM: Homo sapiens

<400> SEQUENCE: 51

Ser Gly Ser Gly Ser Ala Ile Glu Lys Thr Gln Arg Met Leu Ser Gly
1               5                   10                  15

Phe Cys Pro His
        20

<210> SEQ ID NO 52
<211> LENGTH: 20
<212> TYPE: PRT
<213> ORGANISM: Homo sapiens

<400> SEQUENCE: 52

Ser Gly Ser Gly Lys Thr Gln Arg Met Leu Ser Gly Phe Cys Pro His
1               5                   10                  15

Lys Val Ser Ala
        20

<210> SEQ ID NO 53
<211> LENGTH: 20
<212> TYPE: PRT
<213> ORGANISM: Homo sapiens

<400> SEQUENCE: 53

Ser Gly Ser Gly Met Leu Ser Gly Phe Cys Pro His Lys Val Ser Ala
1               5                   10                  15

Gly Gln Phe Ser
        20

<210> SEQ ID NO 54
<211> LENGTH: 20
<212> TYPE: PRT
<213> ORGANISM: Homo sapiens

<400> SEQUENCE: 54

Ser Gly Ser Gly Phe Cys Pro His Lys Val Ser Ala Gly Gln Phe Ser
1               5                   10                  15

Ser Leu His Val
        20

<210> SEQ ID NO 55
<211> LENGTH: 20
<212> TYPE: PRT
<213> ORGANISM: Homo sapiens

<400> SEQUENCE: 55

Ser Gly Ser Gly Lys Val Ser Ala Gly Gln Phe Ser Ser Leu His Val
1               5                   10                  15

Arg Asp Thr Lys
        20

<210> SEQ ID NO 56
<211> LENGTH: 20
<212> TYPE: PRT
<213> ORGANISM: Homo sapiens
```

```
<400> SEQUENCE: 56

Ser Gly Ser Gly Gly Gln Phe Ser Ser Leu His Val Arg Asp Thr Lys
1               5                   10                  15

Ile Glu Val Ala
            20

<210> SEQ ID NO 57
<211> LENGTH: 20
<212> TYPE: PRT
<213> ORGANISM: Homo sapiens

<400> SEQUENCE: 57

Ser Gly Ser Gly Ser Leu His Val Arg Asp Thr Lys Ile Glu Val Ala
1               5                   10                  15

Gln Phe Val Lys
            20

<210> SEQ ID NO 58
<211> LENGTH: 20
<212> TYPE: PRT
<213> ORGANISM: Homo sapiens

<400> SEQUENCE: 58

Ser Gly Ser Gly Arg Asp Thr Lys Ile Glu Val Ala Gln Phe Val Lys
1               5                   10                  15

Asp Leu Leu Leu
            20

<210> SEQ ID NO 59
<211> LENGTH: 20
<212> TYPE: PRT
<213> ORGANISM: Homo sapiens

<400> SEQUENCE: 59

Ser Gly Ser Gly Ile Glu Val Ala Gln Phe Val Lys Asp Leu Leu Leu
1               5                   10                  15

His Leu Lys Lys
            20

<210> SEQ ID NO 60
<211> LENGTH: 20
<212> TYPE: PRT
<213> ORGANISM: Homo sapiens

<400> SEQUENCE: 60

Ser Gly Ser Gly Gln Phe Val Lys Asp Leu Leu Leu His Leu Lys Lys
1               5                   10                  15

Leu Phe Arg Glu
            20

<210> SEQ ID NO 61
<211> LENGTH: 20
<212> TYPE: PRT
<213> ORGANISM: Homo sapiens

<400> SEQUENCE: 61

Ser Gly Ser Gly Asp Leu Leu Leu His Leu Lys Lys Leu Phe Arg Glu
1               5                   10                  15

Gly Arg Phe Asn
            20
```

```
<210> SEQ ID NO 62
<211> LENGTH: 20
<212> TYPE: PRT
<213> ORGANISM: Homo sapiens

<400> SEQUENCE: 62

Ser Gly Ser Gly Pro Ser Thr Ala Leu Lys Glu Leu Ile Glu Glu Leu
1               5                   10                  15

Val Asn Ile Thr
            20

<210> SEQ ID NO 63
<211> LENGTH: 20
<212> TYPE: PRT
<213> ORGANISM: Homo sapiens

<400> SEQUENCE: 63

Ser Gly Ser Gly Leu Lys Glu Leu Ile Glu Glu Leu Val Asn Ile Thr
1               5                   10                  15

Gln Asn Gln Lys
            20

<210> SEQ ID NO 64
<211> LENGTH: 20
<212> TYPE: PRT
<213> ORGANISM: Homo sapiens

<400> SEQUENCE: 64

Ser Gly Ser Gly Asn Gly Ser Met Val Trp Ser Ile Asn Leu Thr Ala
1               5                   10                  15

Gly Val Tyr Cys
            20

<210> SEQ ID NO 65
<211> LENGTH: 20
<212> TYPE: PRT
<213> ORGANISM: Homo sapiens

<400> SEQUENCE: 65

Ser Gly Ser Gly Val Trp Ser Ile Asn Leu Thr Ala Gly Val Tyr Cys
1               5                   10                  15

Ala Ala Leu Glu
            20

<210> SEQ ID NO 66
<211> LENGTH: 20
<212> TYPE: PRT
<213> ORGANISM: Homo sapiens

<400> SEQUENCE: 66

Ser Gly Ser Gly Asn Leu Thr Ala Gly Val Tyr Cys Ala Ala Leu Glu
1               5                   10                  15

Ser Leu Ile Asn
            20

<210> SEQ ID NO 67
<211> LENGTH: 20
<212> TYPE: PRT
<213> ORGANISM: Homo sapiens

<400> SEQUENCE: 67

Ser Gly Ser Gly Gly Val Tyr Cys Ala Ala Leu Glu Ser Leu Ile Asn
1               5                   10                  15
```

Val Ser Gly Cys
            20

<210> SEQ ID NO 68
<211> LENGTH: 20
<212> TYPE: PRT
<213> ORGANISM: Homo sapiens

<400> SEQUENCE: 68

Ser Gly Ser Gly Val Ser Gly Cys Ser Ala Ile Glu Lys Thr Gln Arg
1               5                   10                  15

Met Leu Asn Gly
            20

<210> SEQ ID NO 69
<211> LENGTH: 20
<212> TYPE: PRT
<213> ORGANISM: Homo sapiens

<400> SEQUENCE: 69

Ser Gly Ser Gly Ser Ala Ile Glu Lys Thr Gln Arg Met Leu Asn Gly
1               5                   10                  15

Phe Cys Pro His
            20

<210> SEQ ID NO 70
<211> LENGTH: 20
<212> TYPE: PRT
<213> ORGANISM: Homo sapiens

<400> SEQUENCE: 70

Ser Gly Ser Gly Lys Thr Gln Arg Met Leu Asn Gly Phe Cys Pro His
1               5                   10                  15

Lys Val Ser Ala
            20

<210> SEQ ID NO 71
<211> LENGTH: 20
<212> TYPE: PRT
<213> ORGANISM: Homo sapiens

<400> SEQUENCE: 71

Ser Gly Ser Gly Met Leu Asn Gly Phe Cys Pro His Lys Val Ser Ala
1               5                   10                  15

Gly Gln Phe Ser
            20

<210> SEQ ID NO 72
<211> LENGTH: 20
<212> TYPE: PRT
<213> ORGANISM: Homo sapiens

<400> SEQUENCE: 72

Ser Gly Ser Gly Phe Cys Pro His Lys Val Ser Ala Gly Gln Phe Ser
1               5                   10                  15

Ser Leu Arg Val
            20

<210> SEQ ID NO 73
<211> LENGTH: 20
<212> TYPE: PRT
<213> ORGANISM: Homo sapiens

```
<400> SEQUENCE: 73

Ser Gly Ser Gly Lys Val Ala Gly Gln Phe Ser Ser Leu Arg Val
1               5                   10                  15

Arg Asp Thr Lys
            20

<210> SEQ ID NO 74
<211> LENGTH: 20
<212> TYPE: PRT
<213> ORGANISM: Homo sapiens

<400> SEQUENCE: 74

Ser Gly Ser Gly Gly Gln Phe Ser Ser Leu Arg Val Arg Asp Thr Lys
1               5                   10                  15

Ile Glu Val Ala
            20

<210> SEQ ID NO 75
<211> LENGTH: 20
<212> TYPE: PRT
<213> ORGANISM: Homo sapiens

<400> SEQUENCE: 75

Ser Gly Ser Gly Ser Leu Arg Val Arg Asp Thr Lys Ile Glu Val Ala
1               5                   10                  15

Gln Phe Val Lys
            20

<210> SEQ ID NO 76
<211> LENGTH: 20
<212> TYPE: PRT
<213> ORGANISM: Homo sapiens

<400> SEQUENCE: 76

Ser Gly Ser Gly Ser Leu Arg Val Arg Asp Thr Lys Ile Glu Val Ala
1               5                   10                  15

Gln Phe Val Lys
            20

<210> SEQ ID NO 77
<211> LENGTH: 20
<212> TYPE: PRT
<213> ORGANISM: Homo sapiens

<400> SEQUENCE: 77

Ser Gly Ser Gly Ile Glu Val Ala Gln Phe Val Lys Asp Leu Leu Val
1               5                   10                  15

His Leu Lys Lys
            20

<210> SEQ ID NO 78
<211> LENGTH: 20
<212> TYPE: PRT
<213> ORGANISM: Homo sapiens

<400> SEQUENCE: 78

Ser Gly Ser Gly Gln Phe Val Lys Asp Leu Leu Val His Leu Lys Lys
1               5                   10                  15

Leu Phe Arg Glu
            20
```

```
<210> SEQ ID NO 79
<211> LENGTH: 20
<212> TYPE: PRT
<213> ORGANISM: Homo sapiens

<400> SEQUENCE: 79

Ser Gly Ser Gly Asp Leu Leu Val His Leu Lys Lys Leu Phe Arg Glu
1               5                   10                  15

Gly Gln Phe Asn
            20

<210> SEQ ID NO 80
<211> LENGTH: 16
<212> TYPE: PRT
<213> ORGANISM: Homo sapiens

<400> SEQUENCE: 80

Gln Phe Val Lys Asp Leu Leu Leu His Leu Lys Lys Leu Phe Arg Glu
1               5                   10                  15

<210> SEQ ID NO 81
<211> LENGTH: 16
<212> TYPE: PRT
<213> ORGANISM: Homo sapiens

<400> SEQUENCE: 81

Asp Leu Leu Leu His Leu Lys Lys Leu Phe Arg Glu Gly Arg Phe Asn
1               5                   10                  15

<210> SEQ ID NO 82
<211> LENGTH: 16
<212> TYPE: PRT
<213> ORGANISM: Homo sapiens

<400> SEQUENCE: 82

Gln Phe Val Lys Asp Leu Leu Val His Leu Lys Lys Leu Phe Arg Glu
1               5                   10                  15

<210> SEQ ID NO 83
<211> LENGTH: 16
<212> TYPE: PRT
<213> ORGANISM: Homo sapiens

<400> SEQUENCE: 83

Asp Leu Leu Val His Leu Lys Lys Leu Phe Arg Glu Gly Gln Phe Asn
1               5                   10                  15

<210> SEQ ID NO 84
<211> LENGTH: 12
<212> TYPE: PRT
<213> ORGANISM: Homo sapiens

<400> SEQUENCE: 84

Asp Leu Leu Leu His Leu Lys Lys Leu Phe Arg Glu
1               5                   10

<210> SEQ ID NO 85
<211> LENGTH: 12
<212> TYPE: PRT
<213> ORGANISM: Homo sapiens

<400> SEQUENCE: 85

Asp Leu Leu Val His Leu Lys Lys Leu Phe Arg Glu
1               5                   10
```

<210> SEQ ID NO 86
<211> LENGTH: 36
<212> TYPE: DNA
<213> ORGANISM: Homo sapiens

<400> SEQUENCE: 86
gatgaagctt gccaccatga aatgcagctg ggtcat            36

<210> SEQ ID NO 87
<211> LENGTH: 28
<212> TYPE: DNA
<213> ORGANISM: Homo sapiens

<400> SEQUENCE: 87
gatggactag tgttccttga ccccagta                     28

<210> SEQ ID NO 88
<211> LENGTH: 37
<212> TYPE: DNA
<213> ORGANISM: Homo sapiens

<400> SEQUENCE: 88
gatgaagctt gccaccatga agttgcctgt taggctg            37

<210> SEQ ID NO 89
<211> LENGTH: 31
<212> TYPE: DNA
<213> ORGANISM: Homo sapiens

<400> SEQUENCE: 89
gatgcgtacg tttgatttcc agcttggtgc c                 31

<210> SEQ ID NO 90
<211> LENGTH: 112
<212> TYPE: PRT
<213> ORGANISM: Homo sapiens

<400> SEQUENCE: 90

Ser Pro Val Pro Pro Ser Thr Ala Leu Lys Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Val Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Asn Gly Phe Cys Pro His Lys Val Ser Ala Gly Gln Phe Ser
65                  70                  75                  80

Ser Leu Arg Val Arg Asp Thr Lys Ile Glu Val Ala Gln Phe Val Lys
                85                  90                  95

Asp Leu Leu Val His Leu Lys Lys Leu Phe Arg Glu Gly Gln Phe Asn
            100                 105                 110

<210> SEQ ID NO 91
<211> LENGTH: 339
<212> TYPE: DNA
<213> ORGANISM: Homo sapiens

<400> SEQUENCE: 91
agccctgtgc ctccctctac agccctcaag gagctcattg aggagctggt caacatcacc    60

```
cagaaccaga aggccccgct ctgcaatggc agcatggtgt ggagcatcaa cctgacagct    120
ggcgtgtact gtgcagccct ggaatccctg atcaacgtgt caggctgcag tgccatcgag    180
aagacccaga ggatgctgaa cggattctgc ccgcacaagg tctcagctgg gcagttttcc    240
agcttgcgtg tccgagacac caaaatcgag gtggcccagt ttgtaaagga cctgctcgta    300
catttaaaga aacttttttcg cgagggacag ttcaactga                          339
```

<210> SEQ ID NO 92
<211> LENGTH: 126
<212> TYPE: PRT
<213> ORGANISM: Homo sapiens
<400> SEQUENCE: 92

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
                100                 105                 110

Asp Tyr Trp Gly Gln Gly Thr Leu Val Thr Val Ser Ser Gly
            115                 120                 125
```

<210> SEQ ID NO 93
<211> LENGTH: 112
<212> TYPE: PRT
<213> ORGANISM: Homo sapiens
<400> SEQUENCE: 93

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Asn Ile Val His Ile
                20                  25                  30

Asn Gly Asn Thr Tyr Leu Glu Trp Tyr Leu Gln Lys Pro Gly Gln Ser
            35                  40                  45

Pro Arg Leu Leu Ile Tyr Lys Ile Ser Asp Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Phe Gln Gly
                85                  90                  95

Ser His Val Pro Trp Thr Phe Gly Gln Gly Thr Lys Leu Glu Ile Lys
                100                 105                 110
```

<210> SEQ ID NO 94
<211> LENGTH: 18
<212> TYPE: PRT
<213> ORGANISM: Homo sapiens
<400> SEQUENCE: 94

-continued

Ser Gly Ser Gly Lys Asp Leu Leu His Leu Lys Lys Leu Phe Arg
1               5                   10                  15

Glu Gly

<210> SEQ ID NO 95
<211> LENGTH: 17
<212> TYPE: PRT
<213> ORGANISM: Homo sapiens

<400> SEQUENCE: 95

Ser Gly Ser Gly Asp Leu Leu Leu His Leu Lys Lys Leu Phe Arg Glu
1               5                   10                  15

Gly

<210> SEQ ID NO 96
<211> LENGTH: 16
<212> TYPE: PRT
<213> ORGANISM: Homo sapiens

<400> SEQUENCE: 96

Ser Gly Ser Gly Leu Leu Leu His Leu Lys Lys Leu Phe Arg Glu Gly
1               5                   10                  15

<210> SEQ ID NO 97
<211> LENGTH: 15
<212> TYPE: PRT
<213> ORGANISM: Homo sapiens

<400> SEQUENCE: 97

Ser Gly Ser Gly Leu Leu His Leu Lys Lys Leu Phe Arg Glu Gly
1               5                   10                  15

<210> SEQ ID NO 98
<211> LENGTH: 14
<212> TYPE: PRT
<213> ORGANISM: Homo sapiens

<400> SEQUENCE: 98

Ser Gly Ser Gly Leu His Leu Lys Lys Leu Phe Arg Glu Gly
1               5                   10

<210> SEQ ID NO 99
<211> LENGTH: 13
<212> TYPE: PRT
<213> ORGANISM: Homo sapiens

<400> SEQUENCE: 99

Ser Gly Ser Gly His Leu Lys Lys Leu Phe Arg Glu Gly
1               5                   10

<210> SEQ ID NO 100
<211> LENGTH: 12
<212> TYPE: PRT
<213> ORGANISM: Homo sapiens

<400> SEQUENCE: 100

Ser Gly Ser Gly Leu Lys Lys Leu Phe Arg Glu Gly
1               5                   10

<210> SEQ ID NO 101
<211> LENGTH: 11
<212> TYPE: PRT
<213> ORGANISM: Homo sapiens -continued

```
<400> SEQUENCE: 101

Ser Gly Ser Gly Lys Lys Leu Phe Arg Glu Gly
1               5                   10

<210> SEQ ID NO 102
<211> LENGTH: 10
<212> TYPE: PRT
<213> ORGANISM: Homo sapiens

<400> SEQUENCE: 102

Ser Gly Ser Gly Lys Leu Phe Arg Glu Gly
1               5                   10

<210> SEQ ID NO 103
<211> LENGTH: 9
<212> TYPE: PRT
<213> ORGANISM: Homo sapiens

<400> SEQUENCE: 103

Ser Gly Ser Gly Leu Phe Arg Glu Gly
1               5

<210> SEQ ID NO 104
<211> LENGTH: 8
<212> TYPE: PRT
<213> ORGANISM: Homo sapiens

<400> SEQUENCE: 104

Ser Gly Ser Gly Phe Arg Glu Gly
1               5

<210> SEQ ID NO 105
<211> LENGTH: 17
<212> TYPE: PRT
<213> ORGANISM: Homo sapiens

<400> SEQUENCE: 105

Ser Gly Ser Gly Lys Asp Leu Leu Leu His Leu Lys Lys Leu Phe Arg
1               5                   10                  15

Glu

<210> SEQ ID NO 106
<211> LENGTH: 16
<212> TYPE: PRT
<213> ORGANISM: Homo sapiens

<400> SEQUENCE: 106

Ser Gly Ser Gly Lys Asp Leu Leu Leu His Leu Lys Lys Leu Phe Arg
1               5                   10                  15

<210> SEQ ID NO 107
<211> LENGTH: 15
<212> TYPE: PRT
<213> ORGANISM: Homo sapiens

<400> SEQUENCE: 107

Ser Gly Ser Gly Lys Asp Leu Leu Leu His Leu Lys Lys Leu Phe
1               5                   10                  15

<210> SEQ ID NO 108
<211> LENGTH: 14
<212> TYPE: PRT
<213> ORGANISM: Homo sapiens
```

```
<400> SEQUENCE: 108

Ser Gly Ser Gly Lys Asp Leu Leu Leu His Leu Lys Lys Leu
1               5                   10

<210> SEQ ID NO 109
<211> LENGTH: 13
<212> TYPE: PRT
<213> ORGANISM: Homo sapiens

<400> SEQUENCE: 109

Ser Gly Ser Gly Lys Asp Leu Leu Leu His Leu Lys Lys
1               5                   10

<210> SEQ ID NO 110
<211> LENGTH: 12
<212> TYPE: PRT
<213> ORGANISM: Homo sapiens

<400> SEQUENCE: 110

Ser Gly Ser Gly Lys Asp Leu Leu Leu His Leu Lys
1               5                   10

<210> SEQ ID NO 111
<211> LENGTH: 11
<212> TYPE: PRT
<213> ORGANISM: Homo sapiens

<400> SEQUENCE: 111

Ser Gly Ser Gly Lys Asp Leu Leu Leu His Leu
1               5                   10

<210> SEQ ID NO 112
<211> LENGTH: 10
<212> TYPE: PRT
<213> ORGANISM: Homo sapiens

<400> SEQUENCE: 112

Ser Gly Ser Gly Lys Asp Leu Leu Leu His
1               5                   10

<210> SEQ ID NO 113
<211> LENGTH: 9
<212> TYPE: PRT
<213> ORGANISM: Homo sapiens

<400> SEQUENCE: 113

Ser Gly Ser Gly Lys Asp Leu Leu Leu
1               5

<210> SEQ ID NO 114
<211> LENGTH: 8
<212> TYPE: PRT
<213> ORGANISM: Homo sapiens

<400> SEQUENCE: 114

Ser Gly Ser Gly Lys Asp Leu Leu
1               5

<210> SEQ ID NO 115
<211> LENGTH: 18
<212> TYPE: PRT
<213> ORGANISM: Homo sapiens

<400> SEQUENCE: 115
```

```
Ser Gly Ser Gly Lys Asp Leu Leu Val His Leu Lys Lys Leu Phe Arg
1               5                   10                  15

Glu Gly

<210> SEQ ID NO 116
<211> LENGTH: 17
<212> TYPE: PRT
<213> ORGANISM: Homo sapiens

<400> SEQUENCE: 116

Ser Gly Ser Gly Asp Leu Leu Val His Leu Lys Lys Leu Phe Arg Glu
1               5                   10                  15

Gly

<210> SEQ ID NO 117
<211> LENGTH: 16
<212> TYPE: PRT
<213> ORGANISM: Homo sapiens

<400> SEQUENCE: 117

Ser Gly Ser Gly Leu Leu Val His Leu Lys Lys Leu Phe Arg Glu Gly
1               5                   10                  15

<210> SEQ ID NO 118
<211> LENGTH: 15
<212> TYPE: PRT
<213> ORGANISM: Homo sapiens

<400> SEQUENCE: 118

Ser Gly Ser Gly Leu Val His Leu Lys Lys Leu Phe Arg Glu Gly
1               5                   10                  15

<210> SEQ ID NO 119
<211> LENGTH: 14
<212> TYPE: PRT
<213> ORGANISM: Homo sapiens

<400> SEQUENCE: 119

Ser Gly Ser Gly Val His Leu Lys Lys Leu Phe Arg Glu Gly
1               5                   10

<210> SEQ ID NO 120
<211> LENGTH: 17
<212> TYPE: PRT
<213> ORGANISM: Homo sapiens

<400> SEQUENCE: 120

Ser Gly Ser Gly Lys Asp Leu Leu Val His Leu Lys Lys Leu Phe Arg
1               5                   10                  15

Glu

<210> SEQ ID NO 121
<211> LENGTH: 16
<212> TYPE: PRT
<213> ORGANISM: Homo sapiens

<400> SEQUENCE: 121

Ser Gly Ser Gly Lys Asp Leu Leu Val His Leu Lys Lys Leu Phe Arg
1               5                   10                  15

<210> SEQ ID NO 122
<211> LENGTH: 15
```

```
<212> TYPE: PRT
<213> ORGANISM: Homo sapiens

<400> SEQUENCE: 122

Ser Gly Ser Gly Lys Asp Leu Leu Val His Leu Lys Lys Leu Phe
1               5                   10                  15

<210> SEQ ID NO 123
<211> LENGTH: 14
<212> TYPE: PRT
<213> ORGANISM: Homo sapiens

<400> SEQUENCE: 123

Ser Gly Ser Gly Lys Asp Leu Leu Val His Leu Lys Lys Leu
1               5                   10

<210> SEQ ID NO 124
<211> LENGTH: 13
<212> TYPE: PRT
<213> ORGANISM: Homo sapiens

<400> SEQUENCE: 124

Ser Gly Ser Gly Lys Asp Leu Leu Val His Leu Lys Lys
1               5                   10

<210> SEQ ID NO 125
<211> LENGTH: 12
<212> TYPE: PRT
<213> ORGANISM: Homo sapiens

<400> SEQUENCE: 125

Ser Gly Ser Gly Lys Asp Leu Leu Val His Leu Lys
1               5                   10

<210> SEQ ID NO 126
<211> LENGTH: 11
<212> TYPE: PRT
<213> ORGANISM: Homo sapiens

<400> SEQUENCE: 126

Ser Gly Ser Gly Lys Asp Leu Leu Val His Leu
1               5                   10

<210> SEQ ID NO 127
<211> LENGTH: 10
<212> TYPE: PRT
<213> ORGANISM: Homo sapiens

<400> SEQUENCE: 127

Ser Gly Ser Gly Lys Asp Leu Leu Val His
1               5                   10

<210> SEQ ID NO 128
<211> LENGTH: 9
<212> TYPE: PRT
<213> ORGANISM: Homo sapiens

<400> SEQUENCE: 128

Ser Gly Ser Gly Lys Asp Leu Leu Val
1               5

<210> SEQ ID NO 129
<211> LENGTH: 20
<212> TYPE: PRT
<213> ORGANISM: Homo sapiens
```

```
<400> SEQUENCE: 129

Gln Phe Val Lys Asp Leu Leu Leu His Leu Lys Lys Leu Phe Arg Glu
1               5                   10                  15

Gly Arg Phe Asn
            20

<210> SEQ ID NO 130
<211> LENGTH: 20
<212> TYPE: PRT
<213> ORGANISM: Homo sapiens

<400> SEQUENCE: 130

Gln Phe Val Lys Asp Leu Leu Leu His Ala Lys Lys Leu Phe Arg Glu
1               5                   10                  15

Gly Arg Phe Asn
            20

<210> SEQ ID NO 131
<211> LENGTH: 20
<212> TYPE: PRT
<213> ORGANISM: Homo sapiens

<400> SEQUENCE: 131

Gln Phe Val Lys Asp Leu Leu Leu His Leu Ala Lys Leu Phe Arg Glu
1               5                   10                  15

Gly Arg Phe Asn
            20

<210> SEQ ID NO 132
<211> LENGTH: 20
<212> TYPE: PRT
<213> ORGANISM: Homo sapiens

<400> SEQUENCE: 132

Gln Phe Val Lys Asp Leu Leu Leu His Leu Lys Ala Leu Phe Arg Glu
1               5                   10                  15

Gly Arg Phe Asn
            20

<210> SEQ ID NO 133
<211> LENGTH: 20
<212> TYPE: PRT
<213> ORGANISM: Homo sapiens

<400> SEQUENCE: 133

Gln Phe Val Lys Asp Leu Leu Leu His Leu Lys Lys Ala Phe Arg Glu
1               5                   10                  15

Gly Arg Phe Asn
            20

<210> SEQ ID NO 134
<211> LENGTH: 20
<212> TYPE: PRT
<213> ORGANISM: Homo sapiens

<400> SEQUENCE: 134

Gln Phe Val Lys Asp Leu Leu Leu His Leu Lys Lys Leu Ala Arg Glu
1               5                   10                  15

Gly Arg Phe Asn
            20
```

```
<210> SEQ ID NO 135
<211> LENGTH: 20
<212> TYPE: PRT
<213> ORGANISM: Homo sapiens

<400> SEQUENCE: 135

Gln Phe Val Lys Asp Leu Leu Leu His Leu Lys Lys Leu Phe Ala Glu
 1               5                  10                  15

Gly Arg Phe Asn
            20

<210> SEQ ID NO 136
<211> LENGTH: 20
<212> TYPE: PRT
<213> ORGANISM: Homo sapiens

<400> SEQUENCE: 136

Gln Phe Val Lys Asp Leu Leu Leu His Leu Lys Lys Leu Phe Arg Ala
 1               5                  10                  15

Gly Arg Phe Asn
            20

<210> SEQ ID NO 137
<211> LENGTH: 5
<212> TYPE: PRT
<213> ORGANISM: Homo sapiens

<400> SEQUENCE: 137

Lys Lys Leu Phe Arg
 1               5
```

CHIMERIC AND HUMANISED MONOCLONAL ANTIBODIES AGAINST INTERLEUKIN-13

This application is a 371 of International Application No. PCT/GB2005/002581, filed 30 Jun. 2005, which claims priority from both GB Appln. No. 0414799.7, filed Jul. 1, 2004 and GB 0423675.8, filed Oct. 25, 2004.

FIELD OF THE INVENTION

The present invention relates to immunoglobulins that specifically bind Interleukin 13 (IL-13) and in particular human IL-13 (hIL-13). One embodiment of the invention relates to antibodies that specifically bind hIL-13. The present invention also concerns methods of treating diseases or disorders with said immunoglobulins, pharmaceutical compositions comprising said immunoglobulins and methods of manufacture. Other aspects of the present invention will be apparent from the description below.

BACKGROUND OF THE INVENTION

Interleukin-13 (IL-13)

IL-13 is a 12kDa secreted cytokine originally described as a T cell-derived cytokine that inhibits inflammatory cytokine production. Structural studies indicate that it has a four-helical bundle arrangement held by two disulphide bonds. Although IL-13 has four potential glycosylation sites, analysis of native IL-13 from rat lung has indicated that it is produced as an unglycosylated molecule. Expression of human IL-13 from NSO and COS-7 cells confirms this observation (Eisenmesser et al, J. Mol. Biol. 2001 310(1):231-241; Moy et al, J. Mol. Biol 2001310(1):219-230; Cannon-Carlson et al, Protein Expression and Purification 1998 12(2):239-248).

IL-13 is a pleiotropic cytokine produced by a variety of cell types including activated Th2 cells, mast cells, basophils, dendritic cells, keratinocytes and NKT cells. It can also be produced by Th0, Th1, CD8 and naïve CD45RA$^+$ T cells. IL-13 has immunoregulatory activities that partially overlap with those of IL4, this redundancy may be explained by shared components in the receptors for IL4 and IL-13. IL-13 signals through the type II IL4 receptor which is a heterodimer composed of the IL4Rα and the IL-13Rα1 chains. IL-13Rα1 binds IL-13 with low affinity (Kd=2-10 nM), but when paired with IL4Rα it binds with a high affinity (Kd=400 pM) and forms a functional IL-13 receptor (the human receptor is referred to herein as "hIL-13R") that signals, resulting in activation of JAK/STAT and IRS-1/IRS-2 pathways. An additional IL-13 receptor chain has also been characterised (IL-13Rα2) which binds IL-13 with high affinity (Kd =250 pM) but does not signal, instead it is believed to act as a decoy receptor. Functional receptors for IL-13 are expressed on a wide range of cells including the airway epithelium, smooth muscle, mast cells, eosinophils, basophils, B cells, fibroblasts, monocytes and macrophages. T cells do not have functional receptors for IL-13 (Hilton et al, PNAS 1996 93(1):497-501; Caput et al, J. Biol. Chem. 1996 271(28):16921-16926; Hershey G K, J.Allergy Clin. Immunol. 2003 111(4):677-690).

Both IL-13 and IL-4 act to modify immune and inflammatory responses by promoting allergy associated inflammation and suppressing inflammation due to bacteria, viruses and intracellular pathogens. The principal biological effects of IL-13 include; induction of B cell proliferation and regulation of isotype switching to IgE; induction of MHC II and CD23 expression on B cells and monocytes; up-regulation of VCAM-1 on endothelial cells; regulation of chemokine production; activation of mast cell, eosinophil and neutrophil function as well as inhibition of pro-inflammatory gene expression in monocyte and macrophage populations.

IL-13 does not have any proliferative effects on T cells. Thus unlike IL4, IL-13 does not appear to be important in the initial differentiation of CD4 T cells into Th2-type cells, but rather appears to be important in the effector phase of allergic inflammation (McKenzie et al, PNAS 1993 90(8):3735-3739; Wynn T A, Annu. Rev. Immunol. 2003 21:425-456).

IL-13 and Asthma

Asthma is a chronic lung disease, caused by inflammation of the lower airways and is characterised by recurrent breathing problems. Airways of patients are sensitive and swollen or inflamed to some degree all the time, even when there are no symptoms. Inflammation results in narrowing of the airways and reduces the flow of air in and out of the lungs, making breathing difficult and leading to wheezing, chest tightness and coughing. Asthma is triggered by super-sensitivity towards allergens (e.g. dust mites, pollens, moulds), irritants (e.g. smoke, fumes, strong odours), respiratory infections, exercise and dry weather. The triggers irritate the airways and the lining of the airways swell to become even more inflamed, mucus then clogs up the airways and the muscles around the airways tighten up until breathing becomes difficult and stressful and asthma symptoms appear.

There is strong evidence from animal models and patients that asthmatic inflammation and other pathologies are driven by dysregulated Th2 responses to aeroallergens and other stimuli (Busse et al, Am. J. Resp. Crit. Care Med.1995 152 (1):388-393). In particular, IL-13 is believed to be the major effector cytokine driving a variety of cellular responses in the lung, including airway hyperreactivity, eosinophilia, goblet cell metaplasia and mucus hyper-secretion.

Clinical Evidence for the Role of IL-13 in Asthma

The gene encoding IL-13 is located on chromosome 5q31. This region also contains genes encoding IL-3, IL-4, IL-5, IL-9 and GM-CSF, and has been linked with asthma. Genetic variants of IL-13 that are associated with asthma and atopy have been found both in the promoter and coding regions (Vercelli D, Curr. Opin. Allergy Clin. Immunol. 2002 2(5):389-393). Functional study data are available for the coding variant, Q130 IL-13 (referred to herein as "Q130 IL-13"). The +2044 G to A single nucleotide polymorphism (SNP) found in the fourth exon, results in a substitution of an arginine with a glutamine at position 130 (Q130 IL-13). Also note that in SEQ.ID.NO: 9, this is equivalent to position 110, where the first 'G' amino acid residue at the start of the mature human IL-13 amino acid sequence is position 1. This variant has been found to be associated with asthma, increased IgE levels and atopic dermatitis in Japanese and European populations. Q130 IL-13 is believed to have enhanced stability compared with wild-type IL-13. It also has slightly lower affinity for the IL-13Rα2 decoy receptor and consistent with these observations, higher median serum IL-13 levels are found in patients homozygous for the Q130 IL-13 variant compared with non-homozygous patients. These results indicate that Q130 IL-13 could influence the local and systemic concentrations of IL-13 (Kazuhiko et al, J. Allergy Clin. Immunol. 2002 109 (6):980-987).

Elevated IL-13 levels have been measured in both atopic and non-atopic asthmatics. In one study, average serum IL-13 levels of 50 pg/ml were measured in asthmatic patients compared to 8 pg/ml in normal control patients (Lee et al, J.

Asthma 200138(8):665-671). Increased IL-13 levels have also been measured in plasma, bronchio-alveolar lavage fluid, lung biopsy samples and sputum (Berry et al, J Allergy Clin. Immunol 2004 114(5):1106-1109; Kroegel et al, Eur Respir. J. 1996 9(5):899-904; Huang et al, J. Immunol. 1995 155(5): 2688-2694; Humbert et al, J. Allergy Clin. Immunol. 1997 99(5):657-665).

In vivo Evidence for Involvement of IL-13 in Asthma

A number of studies have defined a critical effector role for IL-13 in driving pathology in both acute and chronic mouse models of allergic asthma. The high affinity IL-13 receptor (IL-13Rα2) or anti-IL-13 polyclonal antibodies have been used to neutralize mouse IL-13 bioactivity in these models. Blockade of IL-13 at the time of allergen challenge completely inhibited OVA-induced airway hyper-reponsiveness, eosinophilia and goblet cell metaplasia. In contrast, administration of antibody to IL-4 after sensitisation and during the allergen challenge phase only partially reduced the asthma phenotype. Thus although exogenous IL-4 and IL-13 are both capable of inducing an asthma-like phenotype, the effector activity for IL-13 appears to be superior to that for IL-4. These data suggest a primary role for IL-4 in immune induction (particularly for Th2 cell development and recruitment to airways, and IgE production), whereas IL-13 is believed to be principally engaged in various effector outcomes, including airway hyper-responsiveness, mucus overproduction and cellular inflammation (Wills-Karp et al, Science 1998 282:2258-2261; Grunig et al, Science 1998 282:2261-2263; Taube et al, J. Immunol. 2002 169:6482-6489; Blease at al, J. Immunol 2001 166(8):5219-5224).

In complementary experiments, lung IL-13 levels have been raised by over-expression in a transgenic mouse or by instillation of IL-13 protein into the trachea of wild-type mice. In both settings, asthma-like characteristics were induced: non-specific airway hyper-responsiveness to cholinergic stimulation, pulmonary eosinophilia, epithelial cell hyperplasia, mucus cell metaplasis, sub-epithelial fibrosis, airways obstruction and Charcot-Leyden-like crystals. In addition, IL-13 was found to be a potent stimulator of matrix metalloproteinases and cathepsin proteases in the lung, resulting in emphysematous changes and mucus metaplasia. Therefore IL-13 may be an important effector molecule both in asthma and COPD disease phenotypes (Zhu et al, J. Clin. Invest. 1999 103(6):779-788; Zheng et al, J. Clin. Invest. 2000 106(9):1081-1093).

These data indicate that IL-13 activity is both necessary and sufficient to produce several of the major clinical and pathological features of allergic asthma in well-validated animal models.

Chronic Obstructive Pulmonary Disease (COPD)

COPD is a generic term covering several clinical syndromes including emphysema and chronic bronchitis. Symptoms are similar to asthma and COPD can be treated with the same drugs. COPD is characterised by a chronic, progressive and largely irreversible airflow obstruction. The contribution of the individual to the course of the disease is unknown, but smoking cigarettes is thought to cause 90% of the cases. Symptoms include coughing, chronic bronchitis, breathlessness and respiratory infections. Ultimately the disease will lead to severe disability and death. Chronic bronchitis is diagnosed in patients with a history of cough or sputum production on most days for at least 3 months over 2 years without any other explanation. Emphysema of the lung is characterised by an abnormal permanent enlargement of the air spaces and destruction of alveolar walls.

IL-13 may play a role in the development of COPD. Human smokers who develop COPD have many inflammatory cell types (neutrophils, macrophages, eosinophils) in the lung parenchyma. IL-13 is a proinflammatory Th2 cytokine therefore to model the progression of emphysema; Zheng et al targeted IL-13 over-expression to the airway epithelium in IL-13 transgenic mice. These animals developed airway and lung parenchymal inflammation and emphysema. They also developed mucus metaplasia reminiscent of chronic bronchitis (J. Clin. Invest. 2000 106(9): 1081-1093).

The IL-13 promoter polymorphism (−1055 C to T) that is associated with allergic asthma has also been reported to have an increased frequency in COPD patients compared to healthy controls. This implies a functional role for the IL-13 promoter polymorphism in the enhanced risk to develop COPD (Kraan et al, Genes and Immunity 2002 3:436-439). In addition, an increased number of IL-13 and IL-4 positive cells were observed in smokers with chronic bronchitis compared to asymptomatic smokers (Miotto et al, Eur. Resp. J. 2003 22:602-608). However a recent study to assess the level of IL-13 expression in the lungs of severe emphysema patients did not find an association between IL-13 levels and disease (Boutten et al, Thorax 2004 59:850-854).

Allergic Disease Including Atopic Dermatitis and Allergic Rhinitis

IL-13 has also been implicated in atopic disorders such as atopic rhinitis and atopic dermatitis. Allergic rhinitis is the most common atopic disease in the United States and is estimated to affect up to 25% of adults and more than 40% of children. There is a close relationship between allergic rhinitis and asthma. Both conditions share common immunopathology and pathophysiology; they have similar immunologic processes in which eosinophils and Th2 lymphocytes in nasal and bronchial tissue play a role. Excessive production of Th2 cytokines, particularly IL-4 and IL-5, is thought to be fundamental in the pathogenesis of allergic disease. IL-13 shares several characteristics and effector functions with IL-4 and this, combined with the functional overlap in IL-4 and IL-13 receptor usage, intracellular signaling components, and genetic organization provides compelling (albeit indirect) evidence for a role of IL-13 in promoting or maintaining human immediate hypersensitivity in vivo. This has been corroborated by Li et al (Li et al. *J Immunol* 1998;161:7007) who demonstrated that atopic subjects with seasonal allergic rhinitis exhibited significantly stronger IL-13 responses in response to Ag-dependent but not polyclonal activation.

Atopic dermatitis is a common, chronic, relapsing, highly pruritic inflammatory skin disease. The lesional skin of atopic dermatitis patients is histologically characterized by an inflammatory T-cell infiltrate, which during acute phases is associated with a predominance of IL-4, IL-5 and IL-13 expression (Simon et al, *J Allergy Clin Immunol* 2004;114: 887; Hamid et al. *J Allergy Clin Immunol* 1996; 98: 225) In addition, Tazawa et al have demonstrated that IL-13 mRNA (but not IL-4) is significantly upregulated in subacute and chronic skin lesions of atopic dermatitis patients (Tazawa et al, Arch Derm Res 2004;296:459). The frequency of IL-13 expressing circulating CD4+ and CD8+ T-cells is also significantly increased in these patients (Aleksza et al British J Dermatol 2002;147;1 135). This increased IL-13 activity is thought to result in raised levels of serum IgE, thereby contributing to the pathogenesis of atopic dermatitis. Furthermore, increased production of IL-13 by neonatal CD4+ T cells is a useful marker for identifying newborns at high risk for subsequent development of allergic diseases, esp. atopic dermatitis (Ohshima et al. *Pediatr Res* 2002; 51:195). Additional evidence for the importance of IL-13 in the etiology of atopic dermatitis was provided by Simon et al (Simon et al, *J Allergy Clin Immunol* 2004; 114:887); topical treatment with tacrolimus ointment (an immunosuppressive drug that inhibits intracellular signaling pathways for cytokine production) resulted in significant clinical and histological improvement of the atopic skin lesions accompanied by significant reductions in local expression of Th2 cytokines, including IL-13. Furthermore, IL-13 Rα1 (a cell surface protein that together with IL-4Rα forms a functional receptor for IL-13) has been shown to be over-expressed on the suprabasal keratinocytes in the skin of atopic dermatitis patients, and IL-13 was able to upregulate IL-13 Rα1 mRNA in vitro (Wongpiyabovorn et al., *J Dermatol Science* 2003;33:31).

These data collectively indicate that IL-13 targeted interventions, including an IL-13 monoclonal antibody, may provide an effective approach for treatment of human allergic disease.

Esophagal Eosinophilia

The accumulation of eosinophils in the esophagus is a common medical problem in patients with diverse diseases, including gastro-esophageal reflux disease, eosinophilic esophagitis, eosinophilic gastroenteritis, and parasitic infections. Esophageal eosinophilia is associated with allergic responses, and repeated challenging of mice with aeroallergens established a link between allergic airway inflammation and esophagal eosinophilia. Th2 cells are thought to induce eosinophil-associated inflammation through the secretion of an array of cytokines including IL-4 and IL-13 that activate inflammatory and effector pathways both directly and indirectly. IL-13 appears to be particularly important because it is produced in high quantities by Th2-cells and regulates multiple features of allergic disease (e.g. IgE production, mucus over-production, eosinophil recruitment and survival, and airway hyperreactivity. Eosinophils can generate functionally active IL-13 after exposure to GM-CSF and/or IL-5 under in vitro, ex vivo, and in vivo conditions in eosinophilic inflammatory responses. (Schmid-Grendelmeier J *Immunology*, 2002,169:1021-1027). IL-13 delivered to the lung of wild-type, STAT-6, eotaxin-1 or IL-5 deficient mice by intratracheal administration, established that pulmonary inflammation, triggered by IL-13, is associated with the development of esophagal eosinophilia (Mishra et al. *Gastroenterol* 2003; 125:1419). Taken together, these data provide evidence for a role of IL-13 in esophagal eosinophilia.

Oncology Indications

Another important area of interest is in targeting IL-13 or IL-13 receptors to inhibit growth of certain types of tumors. Type I T cell-mediated host defenses are believed to mediate optimal tumor rejection in vivo, and deviation to a Th2-type response may contribute to blocking tumor rejection and/or promotion of tumor recurrence (Kobayashi M et al. *J. Immunol.* 1998; 160:5869). Several animal studies using transplantable tumor cell lines support this notion by demonstrating that Stat6, IL-4, and IL-13 (produced in part by NKT cells) were capable of inhibiting tumor rejection (Terabe et al. *Nat. Immunol.* 2000;1:515; Kacha et al. *J. Immunol.* 2000; 165:6024-28; Ostrand-Rosenberg et al. *J. Immunol.* 2000; 165:6015). The potent anti-tumor activity in the absence of Stat-6 was thought to be due to enhancement of tumor-specific IFNg production and CTL activity. In addition, a loss of NKT cells has been shown to reduce IL-13 production with a concomitant rise in tumor recurrence, indicating that IL-13, produced in part by NKT cells is important for immunosurveillance (Terabe et al. *Nat. Immunol.* 2000; 1:515). As such, these findings suggest that IL-13 inhibitors or novel IL-13 antagonists, including IL-13 mAb, may be effective as cancer immunotherapeutics by interfering with the negative regulatory IL-13 plays in downregulating immune responses to tumor cells.

In addition to boosting Th-type-1-associated anti-tumor defenses, IL-13 inhibitors may also be able to block tumor cell growth more directly. For example, in B-cell chronic lymphocytic leukemia (B-CLL) and Hodgkin's disease, IL-13 either blocks apoptosis or promotes tumor cell proliferation (Chaouchi et al. *Blood* 1996; 87:1022; Kapp et al. *J. Exp Med.* 1999; 189:1939). B-CLL is a clinically heterogeneous disease originating from B lymphocytes that involves apoptotic defect in the leukemic cells. IL-13 is not thought to act as a direct growth factor but protects tumor cells from in vitro spontaneous apoptosis (Chaouchi et al. *Blood* 1996; 87:1022; Lai et al. *J. Immunol* 1999; 162:78) and may contribute to B-CLL by preventing neoplastic cell death.

Hodgkin's disease is a type of lymphoma that primarily affects young adults and accounts for about 7,500 cases a year in the United States. The cancer is characterized by the presence of large multi-nucleated Hodgkin/Reed-Sternberg cells (H/RS). In a large majority of cases, the malignant cell population arises from B cells. Several Hodgkin's disease-derived cell lines, as well as lymph node tissue taken from Hodgkin's lymphoma patients, overexpress IL-13 and/or IL-13 receptors. (Kapp et al. *J. Exp Med.* 1999;189:1939, Billard et al. *EurCytokine Netw* 1997;8:19; Skinnider et al. *Blood* 2001; 97:250; Oshima et al, *Cell Immunol* 2001;211:37). Neutralizing anti-IL-13 mAbs or IL-13 antagonists have been shown to inhibit H/RS cell proliferation in a dose-dependent manner (Kapp et al. *J. Exp Med.* 1999; 189:1939; Oshima et al, *Cell Immunol* 2001; 211:37). Similarly, delivery of soluble IL-13Rα2 decoy receptor to NOD/SCID mice with an implanted Hodgkin's disease-derived cell line delayed tumor onset and growth, and enhanced survival, demonstrating that IL-13 neutralization can suppress Hodgkin's lymphoma growth in vitro and in vivo (Trieu et al. *Cancer Research* 2004;64:3271). Collectively, these studies indicate that IL-13 stimulates the proliferation of H/RS cells in an autocrine fashion (Kapp et al. *J. Exp Med.* 1999; 189:1939; Ohshima et al. *Histopathology* 2001; 38:368).

Neutralization of IL-13 may therefore represent an attractive and effective treatment for Hodgkin's disease and other B cell-associated cancers by inhibiting tumor cell growth while at the same time enhancing anti-tumor defenses.

Inflammatory Bowel Diseases

There is a possible role for IL-13 in the pathogenesis of inflammatory bowel disease (IBD). Inflammatory bowel disease comprises a number of diseases clinically classified as ulcerative colitis, Crohn's disease and indeterminate colitis. Its main manifestation is chronic intestinal inflammation due to an exaggerated immune response with an imbalance in the activation of Th1 and Th2 lymphocytes in the intestinal mucosa. This has been demonstrated in animal models of crohn's disease (Bamias et al. Gastroenterol 2005; 128:657) and ulcerative colitis (Heller et al, Immunity 2002; 17:629). Neutralization of IL-13 by IL-13Rα2-Fc administration prevented colitis in a murine Th2 model of human ulcerative colitis (Heller et al, Immunity 2002; 17:629). Furthermore, IL-13 production rapidly supersedes that of IL-4 in this model, and IL-13 production can be induced by stimulation of NKT cells, suggesting that tissue damage may result from toxic activity of IL-13 on the epithelium cells. There are some human data to support these findings: the frequency of IL-13 positive rectal biopsy specimens from patients with ulcerative colitis was significantly higher than of inflammatory and non-inflammatory control subjects, and a higher rate IL-4 and IL-13 expression was observed in acute than non-acute ulcerative colitis (Inoue et al. Am J Gastroenterol 1999;94:2441). In addition Akido et al characterized the immune activity in the muscularis externa from intestinal segments of Crohn's disease patients and found that IL-4 and IL-13 mediate hypercontractility of the intestinal smooth muscle cells via a STAT-6 pathway. The authors concluded that this pathway may contribute to the hypercontractility of intestinal muscles in Crohn's disease (Akiho et al., *Am J Physiol Gastrointest Liver Physiol* 2005; 288:619).

Thus, an IL-13 mAb, possibly in combination with molecules directed at other cytokines, may provide an approach to stop or slow the progression of IBDs.

Psoriasis and Psoriatic Arthritis

Psoriasis is a chronic skin disease characterized by hyperproliferation of keratinocytes and an immunologic cellular infiltrate, including activated T cells, producing various cytokines that can influence the phenotype of epidermal keratinocytes. CDw60 is a carbohydrate-bearing molecule that is upregulated on the surface of psoriatic basal and suprabasal keratinocytes of psoriatic skin. IL-4 and IL-13 secreted from T cells derived from psoriatic lesions have been shown to strongly up-regulate the expression of CDw60 on keratinocytes, (Skov et al., *Am J Pathol* 1997;15:675), whereas interferon-gamma blocked IL-4/IL-13 mediated induction of CDw60 on cultured keratinocytes (Huang et al., *J Invest Dermatol* 2001;116:305). Thus, CDw60 expression on psoriatic epidermal keratinocytes is thought to be induced at least in part by IL-13 secreted by activated T cells within the lesion. In addition, IL-13 Rα1 and IL-4Rα, cell surface proteins that together form a receptor complex for IL-13, are differently expressed in skin biopsies from patients with and without psoriasis (Cancino-Diaz et al., *J Invest Dermatol* 2002;1 19:1114; Wongpiyabovorn et al., *J Dermatol Science* 2003; 33:31), and in vitro experiments demonstrated that IL-13 (but not IL-4) could upregulate the expression of IL-13Rα1 (Wongpiyabovorn et al., *J Dermatol Science* 2003;33:31). Since IL-13 has an effect on a variety of cell types, these studies suggest that the IL-13 receptor may play a part in the early inflammatory process of psoriasis.

Psoriatic arthritis is characterized by synovitis which is mediated by both pro-inflammatory and anti-inflammatory cytokines. The role of IL-13 in various forms of arthritis has been receiving increased interest. Spadaro et al have observed significantly higher levels of IL-13 in synovial fluid of patients with psoriatic arthritis and rheumatoid arthritis than in patients with osteoarthritis. In addition, synovial fluid levels of IL-13 were significantly higher than those in serum in patients with psoriatic arthritis, and the IL-13 synovial fluid/serum ratio was markedly higher in the psoriatic arthritis group than in the rheumatoid arthritis group, suggesting a possible role for the locally produced IL-13 in synovial tissues of patients with psoriatic arthritis (Spadaro et al., *Ann Rheum Dis* 2002; 61:174).

Potential Role of IL-13 in Other Conditions

Acute graft-versus-host disease is a serious cause of morbidity and mortality following stem cell transplantation and is directly related to the degree of human leukocyte antigen (HLA) incompatibility between donor and recipient. Jordan et al first identified IL-13 as a typical Th2 cytokine that is abundantly produced during unrelated, unmatched MLRs (mixed lymphocyte reaction; an in vitro assay for fine-tuning donor selection after initial HLA typing) (Jordan et al. *J Immunol Methods*; 2002;260:1). The same group subsequently showed that IL-13 production by donor T-cells is predictive of acute graft-versus-host-disease (aGVHD) following unrelated donor stem cell transplantation (Jordan et al. *Blood* 2004; 103:717). All patients with severe, grade III aGVHD following stem cell transplantation had donors who produced very high pre-transplantation IL-13 responses, demonstrating a significant link between IL-13 levels and aGVHD and raising the possibility that IL-13 may be directly responsible for some of the aGVHD associated pathology. Consequently, a therapy based on specific blocking of IL-13 may be useful for the treatment of post-stem cell transplantation aGVHD.

Diabetic nephropathy is one of the major causes of end stage renal disease in the Western world. Although the incidence of nephropathy owing to type I diabetes is declining, diabetes mellitus type 2 is now the most common single cause of renal insufficiency in the USA, Japan and Europe. Furthermore, this group of patients has a very poor prognosis on maintenance dialysis owing to extremely high mortality caused by cardiovascular events. It is now increasingly clear that hemodynamic, metabolic and structural changes are interwoven, and various enzymes, transcription factors and growth factors have been identified that play a role in the pathogenesis of this disease. Particularly, TGF-β is important in the development of renal hypertrophy and accumulation of extracellular matrix components, and is considered the pivotal cytokine in mediating collagen formation in the kidney (Cooper. *Diabetologia* 2001; 44:1957; Wolf. *Eur J Clin Invest* 2004; 34 (12): 785). In experimental and human diabetic nephropathy TGF-1 bioactivity is increased and administration of TGF-β1 antibodies to diabetic mouse led to improvement in renal function and reduced extra-cellular matrix accumulation. IL-13 was recently shown in a transgenic mouse model of lung fibrosis to mediate its effects at least in part by regulating the production and activation of TGF-β and collagen deposition (Lee et al. *J. Exp. Med.* 2001; 194:809; Zhu et al. *J. Clin. Invest.* 1999; 103:779), thereby establishing a direct functional link between IL-13 and TGF-β. Consequently a similar role for IL-13 in regulating TGF-b1 activity in the diabetic kidney can be envisioned and IL-13 targeted interventions could potentially have a role in the management of diabetic nephropathy.

Fibrotic Conditions

Pulmonary fibrosis is a condition of inappropriate and harmful scarring of the lungs, leading to disability and often death. The term encompasses a variety of different conditions with distinct etiologies, pathologies and responses to treatment. In some cases the cause of the fibrosis is identified. Causes include: (1) inhaled profibrotic material such as asbestos or silicon, or hard metal dust (2) inhaled organic material to which the patient has an idiosyncratic immunological response leading to fibrosis (e.g. farmer's lung) (3) drugs, such as nitrofurantoin, amiodarone and methotrexate (4) in association with a systemic inflammatory disease, such as Systemic Sclerosis or Rheumatoid Arthritis.

However, in many instances no cause or underlying condition is identified. Many such patients are diagnosed with Idiopathic Pulmonary Fibrosis (IPF). This is a relative rare condition (prevalence 20/100 000). The diagnosis is based on the absence of an identified cause combined with certain radiological and pathological features, particularly honeycombing on the CT or lung biopsy. The disease is usually seen in older patients (>50) and often follows a relentless course of progressive lung impairment leading to death, with the median survival quoted as 2-5 years. Moreover, the patients have the most unpleasant experience of breathlessness progressing over months or years. This initially restricts physical activity, but in the terminal phase—which may last several months—the patient is breathless even at rest and is furthermore oxygen dependent.

At present there is no satisfactory treatment for this disease. Current treatment generally takes the form of corticosteroids and immunosuppressives such as azathioprine. However, corticosteroids may be ineffective in many of patients and their side effects may make the situation worse. There are many potential treatments under investigation including Interferon gamma, which has shown a trend to improved survival in a recent large study, and perfenidone.

There is evidence that IL-13 and cytokines associated with the Th2 phenotype are involved in the process of fibrosis in tissue repair (Wynn T A, Nat. Rev. Immunol. 2004 4:583-594; Jakubzick et al, Am. J. Pathol. 2004 164(6):1989-2001; Jakubzick et al, Immunol. Res. 2004 30(3):339-349; Jakubzick et al, J. Clin. Pathol. 2004 57:477-486). IL-13 and IL-4 have been implicated in a variety of fibrotic conditions. Hepatic fibrosis induced by *Schistosoma* appears to be IL-13 dependent and there is limited evidence that IL-13 is involved in the pathogenesis of scleroderma (Hasegawa et al, J. Rheumatol. 1997 24:328-332; Riccieri et al, Clin. Rheumatol. 2003 22:102-106)

In terms of pulmonary fibrosis, in vitro studies have shown that IL-13 promotes a fibrogenic phenotype. Animal studies have shown elevated levels of IL-13 expression in artificially induced models of fibrosis, and that fibrosis can be reduced by elimination of IL-13.

IL-13 promotes a profibrotic phenotype. At a cellular level, there are several mechanisms by which IL-13 may promote fibrosis. The signal pathways and importance of these various mechanisms are not well defined.

There is evidence that IL-13 acts on the fibroblast both to promote the production of collagen, and to inhibit its breakdown, thus favouring a fibrotic phenotype. Skin fibroblasts possess IL-13 receptors and exposure of cultured skin fibroblasts to IL-13 leads to upregulation of collagen generation (Oriente et al, J. Pharmacol. Exp. Ther. 2000 292:988-994). IL-4 also has a similar, but more transitory effect. A human lung fibroblast cell line (ICIG7) expresses the type II IL-4 receptor (Jinnin et al, J. Biol. Chem 2004 279:41783-41791). Exposure of these cells to IL-13 promotes secretion of a variety of inflammatory and profibrotic mediators: GM-CSF, G-CSF, VCAM beta1 integrin (Doucet et al, Int. Immunol. 1998 10(10):1421-1433).

IL-13 inhibits IL-1a-induced matrix metalloproteinases 1 and 3 protein production by skin fibroblasts which would tend to reduce breakdown of EC matrix (Oriente et al, J. Pharmacol. Exp. Ther. 2000 292:988-994). IL-13 acts synergistically with TGF-β on human fibroblasts obtained by biopsy of asthma airways to promote expression of tissue inhibitor of metalloproteinase 1 (TIMP-1). Breakdown of extracellular matrix is effected by matrix metalloproteinases, which are inhibited by TIMP-1. This action of IL-13 would thus tend to reduce matrix degradation (Zhou et al, Am. J. Physiol. Cell Physiol. 2005 288:C435-C442)

Over-expression of IL-13 in transgenic mice leads to subepithelial fibrosis, epithelial cell hypertrophy, goblet cell hyperplasia, crystal deposition (acidic mammalian chitinase), airway hyper-responsiveness, interstitial fibrosis, type 2 cell hypertrophy and surfactant accumulation (Zhu et al, J. Clin. Invest. 1999 103(6):779-788).

Different strains of mice have different susceptibilities to bleomycin-induced pulmonary fibrosis. C57B1/6J mice, which are susceptible, exhibit rapid up regulation of IL-13, IL-13Roc and IL-4 (as well as TGFβ, TNFRα and IL1Rs) in response to bleomycin. BALB/c mice, which are not susceptible, do not show upregulation of IL-13.

Belperio et al (Am. J. Respir. Cell Mol. Biol. 2002 27:419-427) studied the expression and role of IL-13, IL-4 and the CC chemokine C10 in a mouse bleomycin fibrosis model. Lung tissue levels of both IL-13 and IL-4 increased in response to bleomycin. Prior neutralisation of IL-13 using polyclonal anti IL-13 antibodies significantly reduced lung fibrosis in response to bleomycin as assessed by lung hydroxyproline levels. Despite the increased expression of IL-4 in the same model, neutralisation of IL-4 had no effect on lung fibrosis.

In another model of acute lung fibrosis induced by FITC in the BALB/c mouse, absence of IL-13 (in knockouts), but not IL-4, protected against lung fibrosis. There is no added protection of knockout of IL-4 in IL-13 knockouts (Kolodsick et al, J. Immunol. 2004 172:4068-4076). The protective effect of IL-13 absence is not due to a difference in cell recruitment into the lung: in all knockouts and BALB/c total cell numbers recruited are similar, so the initial inflammatory component seems to be the unaffected. Eosinophil recruitment is lower in IL-4 and IL-13 knockouts compared with BALB/c, but since IL-4–/– were not protected against fibrosis this cannot explain the difference in fibrosis. Perhaps surprisingly, there was no difference in the levels of cytokines between IL-13+/+ and –/–, including for IL10, MCP-1, gamma interferon, TGF-i. In addition, the same number of fibroblasts were isolated from lungs of the different animals post FITC, but in the IL-13–/– mice the production of collagen I is reduced. This indicates the loss of IL-13 is not simply preventing the inflammatory response, but rather is having a more specific anti-fibrotic role. It has been suggested that IL-13 might exert its fibrotic effect via TGF-i (Lee et al, J. Exp. Med. 2001 194:809-821). However in this FITC model, expression of TGF-i was not reduced in IL-13 knock-out mice.

Interleukin 4 may be expected to exert a similar effect as IL-13 as both act via the same receptor. IL-4 is significantly upregulated in the lungs of mice with bleomycin induced lung fibrosis (Gharaee-Kermani et al, Cytokine 2001 15:138-147). However, comparing bleomycin-induced lung fibrosis in C57BL6/J mice which overexpress IL-4, IL-4 knockouts and wild type, lzbicki et al (Am. J. Physiol. Lung Cell Mol. Physiol 2002 283(5):L1110-L1116) did not find evidence that IL-4 was involved in lung fibrosis. Fibrosis was not reduced in IL-4 knockouts, and IL-4 over-expressing mice had increased levels of fibrosis.

BAL cytokine levels of IL-13 are significantly elevated in patients with a variety of forms of pulmonary fibrosis, though with considerable variability. Expression of IL-13 is significantly upregulated in alveolar macrophages obtained from patients with lung fibrosis.

The strongest clinical evidence comes from research at the University of Michigan. Jakubzick and colleagues have studied gene expression of IL-13 and IL-4 and their receptors in surgical lung biopsies from patients with pulmonary fibrosis. IL-13 gene expression is markedly greater in specimens from IPF affected lung than lung from normals or other lung fibrotic conditions. Fibroblasts cultured from patients with IPF/UIP show heightened expression of the IL-13 and IL-4 receptor, compared with tissue and fibroblasts obtained biopsies from patients with normal lungs or other forms of lung fibrosis. In particular, the fibroblastic foci, which are presumably the epicentre of disease activity, stain particularly strongly for these receptors (Jakubzick et al, J. Immunol 2003 171:2684-2693; Jakubzick et al, Am. J. Pathol. 2003 162:

1475-1486; Jakubzick et al, Am. J. Pathol. 2004 164(6):1989-2001; Jakubzick et al, Immunol. Res. 2004 30(3):339-349; Jakubzick et al, J. Clin. Pathol. 2004 57:477-486).

There is good in vitro evidence that Th2 cytokines in general and IL-13 in particular promote a profibrotic phenotype. In at least 2 animal models it has been shown that chemically-induced fibrosis can be reduced by elimination of IL-13 (either in gene knock-out or by anti-IL-13 antibodies). Some evidence indicates that IL-13 is more important at promoting pulmonary fibrosis than IL-4. Clinical evidence for the role of IL-13 in pulmonary fibrosis suggests that IL-13 and its receptors are unregulated in the lungs of patients with IPF.

A growing body of data suggests an important role for IL-13 based therapies for the treatment of a variety of fibrotic conditions, including schistosomiasis-induced hepatic fibrosis, and various forms of pulmponary fibrosis (e.g. IPF [discussed elsewhere], scleroderma).

Experiments in which IL-4 and IL-13 were inhibited independently identified IL-13 as the dominant effector cytokine of fibrosis in several models (Chiaramonte et al *J. Clin. Invest.* 1999;104: 777-785; Blease et al. *J. Immunol* 2001; 166:5219; Kumar et al. *Clin. Exp. Allergy* 2002; 32:1104). In schistosomiasis, although the egg-induced inflammatory response was unaffected by IL-13 blockade, collagen deposition decreased by more than 85% in chronically infected animals (Chiaramonte et al *J. Clin. Invest.* 1999; 104: 777; Chiaramonte et al *Hepatology* 2001; 34:273) despite continued and undiminished production of IL-4.

The amino acid sequence for hIL-13 is set forth as SEQ.I.D.NO: 9. (This is the mature protein sequence, that is, no signal sequence is present).

A CDNA encoding hIL-13 is set forth in SEQ.I.D.NO:10. (This is the DNA sequence for the mature protein sequence, that is, no signal sequence is present).

All patent and literature references disclosed within the present specification (including any patent application to which this application claims priority) are expressly and entirely incorporated herein by reference.

Recently vaccines raising immune responses against IL-13 for the treatment of asthma have been described (WO 02/070711). A role for IL-13 in the sensitisation of the skin to environmental allergens has also been recently described (Herrick et al., The Journal of Immunology, 2003, 170:2488-2495).

The present invention provides, inter alia, an antibody referred to as 6A1. As demonstrated below, 6A1 binding with hIL-13 appears dependent on the presence of arginine at position 107 of SEQ.I.D.NO:9. Arginine at position 107 of SEQ.I.D.NO:9 is reported to be an important residue involved in hIL-13/hIL-13R interaction. Thompson J. P and Debinski W (1999) J.Biol.Chem, vol.24, No:42 pp29944-29950 stated "Glutamic acids at positions 13 and 16 in hIL 3 α-helix A, arginine and serine at positions 66 and 69 in helix C, and arginine at position 109 in helix D were found to be important in inducing biological signalling since their specific mutation resulted in loss and/or gain of function phenomena." (See abstract and entire disclosure). The arginine at position 109 of this paper is equivalent to 107 in SEQ.I.D.NO:9 of the present specification due to a differing numbering approach used by the present inventors to that used by the authors of this paper. Thus 6A1 binding with hIL-13 involves one of the residues on hIL-13 previously identified as being important in hIL-13/hIL-13R interaction and therefore biological signalling of the IL-13 pathway.

SUMMARY OF THE INVENTION

The present invention therefore provides a therapeutic antibody or antigen binding fragment thereof which specifically binds hIL-13 and neutralises the activity of hIL-13. See, for example, Table A below.

The term "specifically binds" as used throughout the present specification in relation to antibodies and antigen binding fragments thereof of the invention means that the antibody binds hIL-13 with no or insignificant binding to other human proteins and in particular human IL-4. The term however does not exclude the fact that antibodies of the invention may also be cross-reactive with cynomolgus IL-13.

In another aspect of the present invention there is provided a therapeutic antibody or antigen binding fragment thereof which specifically binds hIL-13 and modulates (e.g. inhibits or blocks) the interaction between hIL-13 and hIL-13R. Such inhibition includes but is not limited to competitive inhibition. In certain embodiments, antibodies of the invention at least inhibit the interaction between hIL-13 and hIL-13R but may also block the interaction between hIL-13 and hIL-13R thereby decoupling the hIL-13/hIL-13R signalling pathway.

In another aspect, there is provided a therapeutic antibody or antigen binding fragment thereof which specifically binds hIL-13, and comprises a CDRH3 having the sequence set forth in SEQ.I.D.NO:3.

In another aspect of the invention there is provided a therapeutic antibody or antigen binding fragment thereof which specifically binds hIL-13 and comprises a CDRH3 which is a variant of the sequence set forth in SEQ.I.D.NO:3 in which one or two residues within said CDRH3 of said variant differs from the residue in the corresponding position in SEQ.I.D.NO:3.

In another aspect of the present invention there is provided a therapeutic antibody or antigen binding fragment thereof which specifically binds hIL-13, and comprises the following CDRs:

```
CDRH1:          SEQ. I.D. NO: 1
CDRH2:          SEQ. I.D. NO: 2
CDRH3:          SEQ. I.D. NO: 3
CDRL1:          SEQ. I.D. NO: 4
CDRL2:          SEQ. I.D. NO: 5
CDRL3:          SEQ. I.D. NO: 6
```

Throughout this specification, amino acid residues in antibody sequences are numbered according to the Kabat scheme. Similarly, the terms "CDR", "CDRL1", "CDRL2", "CDRL3", "CDRH1", "CDRH2", "CDRH3" follow the Kabat numbering system as set forth in Kabat et al; *Sequences of proteins of Immunological Interest* NIH, 1987. "CDRH1" is taken to be the stretch of sequence which includes both the Kabat definition of CDRH1 (residues 31-35B) and also the CDRH1 definition of Chothia (Chothia et al (1989); Conformations of immunoglobulins hypervariable regions; Nature 342, p877-883) which comprises Kabat 26-32. Therefore the following defines the CDRs according to the invention:

| CDR: | Residues |
| --- | --- |
| CDRH1: | 26-35B |
| CDRH2: | 50-65 |
| CDRH3: | 95-102 |
| CDRL1: | 24-34 |
| CDRL2: | 50-56 |
| CDRL3: | 89-97 |

In another aspect of the invention there is provided a therapeutic antibody or antigen binding fragment thereof comprising a VH domain having the sequence set forth in SEQ.I.D.NO:7 and a VL domain having the sequence set forth in SEQ.I.D.NO:8.

In another aspect of the invention there is provided an isolated VH domain of an antibody comprising (or consisting essentially of, or consisting of) SEQ.I.D.NO: 7 or 11,12, 13, 14.

In another aspect of the invention there is provided a therapeutic antibody or antigen binding fragment thereof comprising a VH domain selected from the group consisting of; SEQ.I.D.NO: 7 or 11,12,13,14

In another aspect of the present invention there is provided a therapeutic antibody or antigen binding fragment thereof which competitively inhibits the binding of the therapeutic antibody comprising the CDRH3 of SEQ I.D.NO: 3 to hIL-13.

In another aspect of the invention there is provided a therapeutic antibody or antigen binding fragment thereof which competitively inhibits the binding of the therapeutic antibody comprising CDRs of SEQ.I.D. NO: 1,2,3,4, 5 and 6 to hIL-13.

In another aspect of the invention there is provided a therapeutic antibody or antigen binding fragment thereof which competitively inhibits the binding of the therapeutic antibody comprising a heavy chain of SEQ.I.D.NO: 18 and a light chain of SEQ.I.D.NO:22 to hIL-13.

In accordance with the present invention there is provided a humanised therapeutic antibody which antibody comprises a VH domain selected from the group consisting of: SEQ.I.D.NO:11, 12, 13, 14 and a VL domain selected from the group consisting of: SEQ.I.D.NO:15, 16.

In another aspect of the invention there is provided a method of treating a human patient afflicted with a disease or disorder responsive to modulation of the interaction between hIL-13 and hIL-13R (such as asthma, COPD, allergic rhinitis, atopic dermatitis) which method comprises the step of administering to said patient a therapeutically effective amount of the therapeutic antibody or antigen binding fragment thereof as described herein.

Use of an antibody of the invention in the manufacture of a medicament for the treatment of a disease or disorder responsive to modulation of the interaction between hIL-13 and hIL-13R is also provided.

In another aspect of the present invention there is provided a therapeutic antibody that specifically binds human IL-13, which antibody specifically binds human IL-13 between residues 97 to 108 of SEQ.I.D.NO:9. As is apparent to those skilled in the art on the basis of the results disclosed below, "between residues 97 to 108 of SEQ.I.D.NO:9" is inclusive of positions 97 and 108.

In another aspect of the present invention there is provided a therapeutic antibody that competitively inhibits the binding of the therapeutic antibody having CDRH3 of SEQ.I.D.NO:3 to human IL-13 (such as a therapeutic antibody comprising a heavy chain of SEQ.I.D.NO:18 and a light chain of SEQ.I.D.NO:22), which competing antibody specifically binds human IL-13 between residues 97 to 108 of SEQ.I.D.NO:9.

In another aspect of the present invention there is provided a therapeutic antibody that specifically binds human IL-13 between residues 103 to 107 inclusively of SEQ.I.D.NO:9 and modulates (e.g. inhibits or blocks) the interaction between hIL-13 and hIL-13R.

In one embodiment of the invention there is provided a pharmaceutical composition comprising a plurality of monoclonal therapeutic antibodies (which are typically human or humanised) which specifically bind hIL-13 between residues 103 to 107, of SEQ.I.D.NO:9 and modulate (e.g. inhibits or blocks) the interaction between hIL-13 and hIL-13R and a pharmaceutical acceptable carrier.

In another embodiment of the invention there is provided a method of producing a therapeutic antibody which specifically binds hIL-13 between residues 103 to 107 of SEQ.I.D.NO:9 and modulate (e.g. inhibits or blocks) the interaction between hIL-13 and hIL-13R which method comprises the step of culturing in a serum-free culture media, a recombinant host cell comprising a first and second vector wherein said first vector comprises a polynucleotide encoding the heavy chain of said antibody and said second vector comprises a polynucleotide encoding the light chain of said antibody. As will be apparent to the skilled person on the basis of the results below "between 103 to 107 of SEQ.I.D.NO:9" is inclusive of positions 103 and 107.

In another embodiment of the invention there is provided a method of producing a therapeutic antibody which specifically binds hIL-13 between residues 97 to 108 of SEQ.I.D.NO:9 and modulate (e.g. inhibits or blocks) the interaction between hIL-13 and hIL-13R which method comprises the step of culturing in a serum-free culture media, a recombinant host cell comprising a first and second vector wherein said first vector comprises a polynucleotide encoding the heavy chain of said antibody and said second vector comprises a polynucleotide encoding the light chain of said antibody.

In another embodiment of the invention there is provided an intact therapeutic antibody which binds hIL-13 and modulates (e.g. inhibits or blocks) the interaction between hIL-13 and hIL-13R which antibody interacts with residue 107 of SEQ.I.D.NO:9.

In another embodiment of the invention there is provided an intact therapeutic antibody which binds hIL-13 and modulates (e.g. inhibits or blocks) the interaction between hIL-13 and hIL-13R wherein the binding between said therapeutic antibody and hIL-13 depends on (or positively correlates to) the presence of an arginine residue at position 107 of SEQ.I.D.NO:9.

In another embodiment there is provided a therapeutic antibody that specifically binds hIL-13 and modulates (e.g. inhibits or blocks) the interaction between hIL-13 and hIL-13R and has a dissociation constant $k_{off}$ in the range $1.4 \times 10^{-4}$ to $8.22 \times 10^{-5}$ $s^{-1}$ (for example as measured by Biacore™). Such antibody may comprise a CDRH3 of SEQ.I.D.NO:3 or variant thereof and may further comprise in addition to SEQ.I.D.NO:3 or variant thereof, SEQ.I.D.NO:1, 2, 4, 5 and 6.

In another embodiment there is provided an antibody that specifically binds hIL-13 and modulates (e.g. inhibits or blocks) the interaction between hIL-13 and hIL-13R which antibody comprises CDRH3 of SEQ.I.D.NO:3 and optionally further comprises each of CDRH1 of SEQ.I.D.NO:1, CDRH2 of SEQ.I.D.NO:2, CDRL1 of SEQ.I.D.NO:4, CDRL2 of SEQ.I.D.NO:5 and CDRL3 of SEQ.I.D.NO:6 wherein said antibody is also cross-reactive with cynomolgus IL-13 (cIL-13).

DETAILED DESCRIPTION OF THE INVENTION

1. Antibody Structures 1.1 Intact Antibodies

Figure 1:
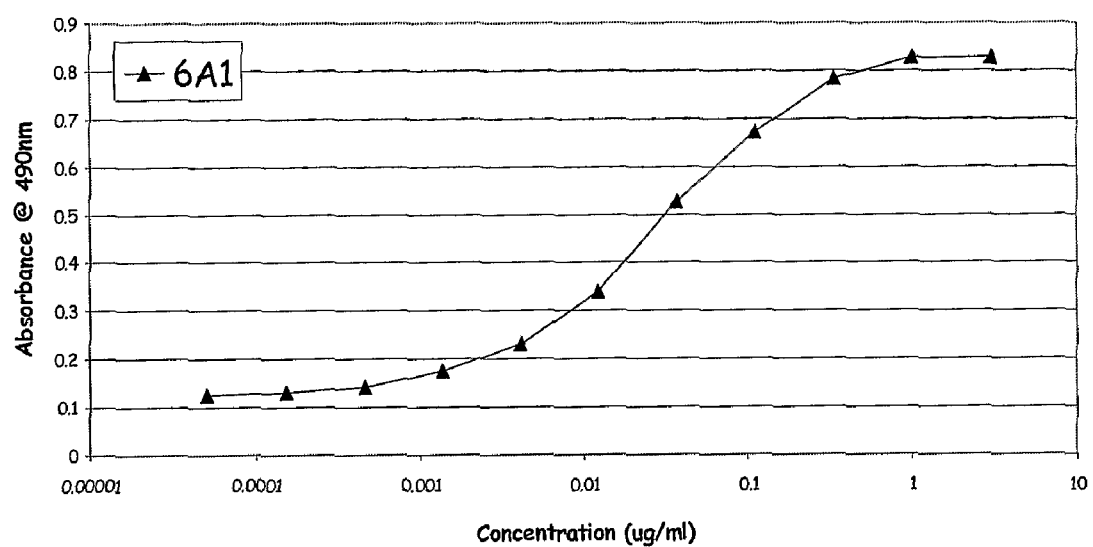
FIG. 1
Sandwich ELISA illustrating the binding of monoclonal antibody 6A1 to recombinant *E.coli*-expressed human IL-13 at increasing concentrations.

Intact antibodies include heteromultimeric glycoproteins comprising at least two heavy and two light chains. Aside from IgM, intact antibodies are usually heterotetrameric glycoproteins of approximately 150 Kda, composed of two identical light (L) chains and two identical heavy (H) chains.

Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain (VH) followed by a number of constant regions. Each light chain has a variable domain (VL) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called Framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade.

In one embodiment therefore we provide an intact therapeutic antibody that specifically binds hIL-13, which antibody modulates (e.g. inhibits or blocks) the interaction between hIL-13 and hIL-13R. The intact therapeutic antibody may comprise a constant region of any isotype or subclass thereof described supra. In one embodiment, the antibody is of the IgG isotype, particularly IgG1. The antibody may be rat, mouse, rabbit, primate or human. In one typical embodiment, the antibody is primate (such as cynomolgus, Old World monkey or Great Ape, see e.g. WO99/55369, WO93/02108) or human.

In another embodiment there is provided an isolated intact therapeutic antibody comprising a CDRH3 of SEQ.I.D.NO: 3. In another embodiment there is provided an intact therapeutic antibody comprising a variable region having CDRs of SEQ.I.D.NO: 1, 2,3,4,5 and 6.

In another embodiment, there is provided an isolated murine intact therapeutic antibody or antigen binding fragment thereof comprising a VH domain having the sequence of SEQ.I.D.NO: 7 and a VL domain of the sequence of SEQ.I.D.NO: 8.

1.1.2 Human Antibodies

Human antibodies may be produced by a number of methods known to those of skill in the art. Human antibodies can be made by the hybridoma method using human myeloma or mouse-human heteromyeloma cells lines see Kozbor J.Immunol 133, 3001, (1984) and Brodeur. *Monoclonal Antibody Production Techniques and Applications*, pp51-63 (Marcel Dekker Inc, 1987). Alternative methods include the use of phage libraries or transgenic mice both of which utilize human V region repertories (see Winter G, (1994), Annu.Rev.Immunol 12,433-455, Green L L (1999), J.Immunol.methods 231, 11-23).

Several strains of transgenic mice are now available wherein their mouse immunoglobulin loci has been replaced with human immunoglobulin gene segments (see Tomizuka K, (2000) PNAS 97,722-727; Fishwild D. M (1996) Nature Biotechnol. 14,845-851, Mendez M J, 1997, Nature Genetics, 15,146-156). Upon antigen challenge such mice are capable of producing a repertoire of human antibodies from which antibodies of interest can be selected. Of particular note is the Trimera™ system (see Eren R et al, (1998) Immunology 93:154-161) where human lymphocytes are transplanted into irradiated mice, the Selected Lymphocyte Antibody System (SLAM, see Babcook et al, PNAS (1996) 93:7843-7848) where human (or other species) lymphocytes are effectively put through a massive pooled in vitro antibody generation procedure followed by deconvulated, limiting dilution and selection procedure and the Xenomouse II™ (Abgenix Inc). An alternative approach is available from Morphotek Inc using the Morphodoma T technology.

Phage display technology can be used to produce human antibodies (and fragments thereof), see McCafferty; Nature, 348, 552-553 (1990) and Griffiths A D et al (1994) EMBO 13:3245-3260. According to this technique antibody V domain genes are cloned in frame into either a major or minor coat of protein gene of a filamentous bacteriophage such as M13 or fd and displayed (usually with the aid of a helper phage) as functional antibody fragments on the surface of the phage particle. Selections based on the functional properties of the antibody result in selection of the gene encoding the antibody exhibiting those properties. The phage display technique can be used to select antigen specific antibodies from libraries made from human B cells taken from individuals afflicted with a disease or disorder described above or alternatively from unimmunized human donors (see Marks; J.Mol.Bio. 222,581-597, 1991). Where an intact human antibody is desired comprising a Fc domain it is necessary to redone the phage displayed derived fragment into a mammalian expression vectors comprising the desired constant regions and establishing stable expressing cell lines. The technique of affinity maturation (Marks; Bio/technol 10,779-783 (1992)) may be used to improve binding affinity wherein the affinity of the primary human antibody is improved by sequentially replacing the H and L chain V regions with naturally occurring variants and selecting on the basis of improved binding affinities. Variants of this technique such as "epitope imprinting" are now also available see WO 93/06213. See also Waterhouse; Nucl.Acids Res 21, 2265-2266 (1993).

Thus in another embodiment there is provided an isolated human intact therapeutic antibody or antigen binding fragment thereof which specifically binds hIL-13 and modulates (e.g. inhibits or blocks) the interaction between hIL-13 and hIL-13R.

In another aspect there is provided an isolated human intact therapeutic antibody or antigen binding fragment thereof comprising a CDRH3 of SEQ.I.D.NO: 3 which specifically binds hIL-13 and modulates (e.g. inhibits or blocks) the interaction between hIL-13 and hIL-13R. In another aspect there is provided an isolated human intact therapeutic antibody or antigen binding fragment thereof comprising a variable region having CDRs of SEQ.I.D.NO: 1, 2, 3, 4, 5 and 6 as defined supra.

1.2 Chimaeric and Humanised Antibodies

The use of intact non-human antibodies in the treatment of human diseases or disorders carries with it the potential for the now well established problems of immunogenicity, that is the immune system of the patient may recognise the non-human intact antibody as non-self and mount a neutralising response. This is particularly evident upon multiple administration of the non-human antibody to a human patient. Various techniques have been developed over the years to overcome these problems and generally involve reducing the composition of non-human amino acid sequences in the intact antibody whilst retaining the relative ease in obtaining non-human antibodies from an immunised animal e.g. mouse, rat or rabbit. Broadly two approaches have been used to achieve this. The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimaeric antibodies are typically produced using recombinant DNA methods. DNA.encoding the antibodies (e.g. cDNA) is isolated and sequenced using conventional procedures (e.g. by using oligonucleotide probes that are capable of binding specifically to genes encoding the H and L chains of the antibody of the invention, e.g. DNA encoding SEQ.I.D.NO 1,2,3,4,5 and 6 described supra). Hybridoma cells serve as a typical source of such DNA. Once isolated, the DNA is placed into expression vectors which are then transfected into host cells such as E.coli, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ("donor" antibodies) onto human framework ("acceptor framework") and constant regions (see Jones et al (1986) Nature 321,522-525 and Verhoeyen M et al (1988) Science 239, 1534-1536). However, CDR grafting per se may not result in the complete retention of antigen-binding properties and it is frequently found that some framework residues (sometimes referred to as "back-mutations") of the donor antibody need to be preserved in the humanised molecule if significant antigen-binding affinity is to be recovered (see Queen C et al (1989) PNAS 86,10,029-10,033, Co, M et al (1991) Nature 351, 501-502). In this case, human V regions showing the greatest sequence homology to the non-human donor antibody are chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody maybe used to help identify such structurally important residues, see WO99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A. et al; (1991) Mol.lmmunol.28, 489-498 and Pedersen J. T. et al (1994) J.Mol.Biol. 235; 959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system (see also Mark G. E. et al (1994) in Handbook of Experimental Pharmacology vol. 113: The pharmacology of monoclonal Antibodies, Springer-Verlag, pp 105-134). This procedure of humanisation is referred to as "veneering" because only the surface of the antibody is altered, the supporting residues remain undisturbed.

Thus another embodiment of the invention there is provided a chimaeric therapeutic antibody comprising a non-human (e.g. rodent) variable domain fused to a human constant region (which maybe of a IgG isotype e.g. IgG1) which specifically binds hIL-13 and modulates (e.g. inhibits or blocks) the interaction between hIL-13 and hIL-13R.

In another embodiment there is provided a chimaeric therapeutic antibody comprising a non-human (e.g. rodent) variable region and a human constant region (which maybe of an IgG isotype e.g. IgG1) which specifically binds hIL-13, which antibody further comprises a CDRH3 of SEQ.I.D.NO3. Such antibodies may further comprise a human constant region of the IgG isotype, e.g. IgG1

In another embodiment there is chimaeric therapeutic antibody comprising a non-human (e.g. rodent) variable region and a human constant region (which maybe of a IgG isotype e.g. IgG1) which specifically binds hIL-13 having the CDRs of SEQ.I.D.NO: 1, 2,3,4,5 and 6.

In another embodiment there is provided a chimaeric therapeutic antibody comprising a VH domain of SEQ.I.D.NO:7 and a VL domain of SEQ.I.D.NO:8 and a human constant region of an IgG isotype, e.g. IgG1which specifically binds hIL-13 and modulates (e.g. inhibits or blocks) the interaction between hIL-13 and hIL-13R.

In another embodiment there is provided a humanised therapeutic antibody or antigen binding fragment thereof which specifically binds hIL-13 and modulates (e.g. inhibits or blocks) the interaction between hIL-13 and hIL-13R.

In another embodiment there is provided a humanised therapeutic antibody or antigen binding fragment thereof which specifically binds hIL-13 and comprises a CDRH3 of SEQ.I.D.NO: 3. Such antibodies may comprise a human constant region of the IgG isotype, e.g. IgG1.

In another embodiment there is provided a humanised therapeutic antibody or antigen binding fragment thereof which specifically binds hIL-13 and comprises CDRs of SEQ.I.D.NO1, 2,3,4,5 and 6. Such antibodies may comprise a human constant region of the IgG isotype, e.g. IgG1.

In accordance with the present invention there is provided a humanised therapeutic antibody which antibody comprises a VH domain selected from the group of: SEQ.I.D.NO:11, 12, 13, 14 and a VL domain selected from the group of:

SEQ.I.D.NO:15,16. Such antibodies may comprise a human constant region of the IgG isotype e.g. IgG1.

In another embodiment there is provided a humanised therapeutic antibody which antibody comprises a VH domain of SEQ.I.D.NO: 11 and a VL domain of SEQ.I.D.NO:15.

In another embodiment there is provided a humanised therapeutic antibody which antibody comprises a VH domain of SEQ.I.D.NO: 12 and a VL domain of SEQ.I.D.NO:15.

In another embodiment there is provided a humanised therapeutic antibody which antibody comprises a VH domain of SEQ.I.D.NO: 13 and a VL domain of SEQ.I.D.NO:15.

In another embodiment there is provided a humanised therapeutic antibody which antibody comprises a VH domain of SEQ.I.D.NO: 14 and a VL domain of SEQ.I.D.NO:15.

In another embodiment there is provided a humanised therapeutic antibody which antibody comprises a VH domain of SEQ.I.D.NO: 11 and a VL domain of SEQ.I.D.NO:16.

In another embodiment there is provided a humanised therapeutic antibody which antibody comprises a VH domain of SEQ.I.D.NO: 12 and a VL domain of SEQ.I.D.NO:16.

In another embodiment there is provided a humanised therapeutic antibody which antibody comprises a VH domain of SEQ.I.D.NO: 13 and a VL domain of SEQ.I.D.NO:16.

In another embodiment there is provided a humanised therapeutic antibody which antibody comprises a VH domain of SEQ.I.D.NO: 14 and a VL domain of SEQ.I.D.NO:16

In another embodiment of the present invention there is provided a humanised therapeutic antibody or antigen binding fragment thereof which specifically binds hIL-13 wherein said antibody or fragment thereof comprises CDRH3 (SEQ.I.D.NO:3) optionally further comprising CDRs of SEQ.I.D.NO:1,2,4,5 and 6 wherein the residues selected from the group consisting of 19,38,73 and 81 of the human acceptor heavy chain framework region and the residue at position 85 of the human acceptor light chain framework are substituted by the corresponding residues found in the donor antibody framework from which CDRH3 is derived.

It will be apparent to those skilled in the art that the term "derived" is intended to define not only the source in the sense of it being the physical origin for the material but also to define material which is structurally identical (in terms of primary amino acid sequence) to the material but which does not originate from the reference source. Thus "residues found in the donor antibody from which CDRH3 is derived" need not necessarily have been purified from the donor antibody.

In another embodiment there is provided a humanised therapeutic antibody or antigen binding fragment thereof which specifically binds hIL-13 wherein said antibody or fragment thereof comprises CDRH3 of SEQ.I.D.NO:3 optionally further comprising CDRs of SEQ.I.D.NO:1, 2, 4, 5 and 6 wherein the human heavy chain framework comprises one or more (e.g. all) of the following residues (or a conservative substitute thereof):

| Position | Residue |
|----------|---------|
| 38 | I |
| 19 | R |
| 73 | T |
| 81 | R |
| and the human light chain comprises | |
| 85 | V |

It is well recognised in the art that certain amino acid substitutions are regarded as being "conservative". Amino acids are divided into groups based on common side-chain properties and substitutions within groups that maintain all or substantially all of the binding affinity of the antibody of the invention or antigen binding fragment thereof are regarded as conservative substitutions, see the following table:

| Side chain | Members |
|------------|---------|
| Hydrophobic | met, ala, val, leu, ile |
| neutral hydrophilic | cys, ser, thr |
| Acidic | asp, glu |
| Basic | asn, gln, his, lys, arg |
| residues that influence chain orientation | gly, pro |
| Aromatic | trp, tyr, phe |

In accordance with the present invention there is provided a humanised therapeutic antibody comprising a heavy chain selected from the group consisting of: SEQ.I.D.NO: 18,19, 20,21 and a light chain selected from the group consisting of; SEQ.I.D.NO:22, 23.

In one embodiment of the invention there is provided a humanised therapeutic antibody which specifically binds hIL-13 comprising a heavy chain of SEQ.I.D.NO:18 and a light chain of SEQ.I.D.NO:22.

In one embodiment of the invention there is provided a humanised therapeutic antibody which specifically binds hIL-13 comprising a heavy chain of SEQ.I.D.NO:19 and a light chain of SEQ.I.D.NO:22.

In one embodiment of the invention there is provided a humanised therapeutic antibody which specifically binds hIL-13 comprising a heavy chain of SEQ.I.D.NO:20 and a light chain of SEQ.I.D.NO:22.

In one embodiment of the invention there is provided a humanised therapeutic antibody which specifically binds hIL-13 comprising a heavy chain of SEQ.I.D.NO:21 and a light chain of SEQ.I.D.NO:22.

In one embodiment of the invention there is provided a humanised therapeutic antibody which specifically binds hIL-13 comprising a heavy chain of SEQ.I.D.NO:18 and a light chain of SEQ.I.D.NO:23.

In one embodiment of the invention there is provided a humanised therapeutic antibody which specifically binds hIL-13 comprising a heavy chain of SEQ.I.D.NO:19 and a light chain of SEQ.I.D.NO:23.

In one embodiment of the invention there is provided a humanised therapeutic antibody which specifically binds hIL-13 comprising a heavy chain of SEQ.I.D.NO:20 and a light chain of SEQ.I.D.NO:23.

In one embodiment of the invention there is provided a humanised therapeutic antibody which specifically binds hIL-13 comprising a heavy chain of SEQ.I.D.NO:21 and a light chain of SEQ.I.D.NO:23.

1.3 Bispecific Antibodies

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. In one preferred approach, the bispecific antibody is composed of a H chain with a first binding specificity in one arm and a H-L chain pair, providing a second binding specificity in the other arm, see WO94/04690. Also see Suresh et al Methods in Enzymology 121, 210, 1986.

In one embodiment of the invention there is provided a bispecific therapeutic antibody wherein at least one binding specificity of said antibody is for hIL-13, wherein said antibody modulates (e.g. inhibits or blocks) the interaction between hIL-13 and IL-13R. Such antibodies may further comprise a human constant region of the IgG isotype, e.g. IgG1. In some embodiments, the bispecific therapeutic antibody has a first binding specificity for hIL-13 and modulates (e.g. inhibits or blocks) the interaction between hIL-13 and hIL-13R and a second binding specificity for hIL-4 and modulates (e.g. inhibits or blocks) the interaction between hIL-4 and a receptor for hIL-4.

In one embodiment of the invention there is provided a bispecific therapeutic antibody wherein at least one binding specificity of said antibody is for hIL-13, wherein said antibody comprises a CDRH3 of SEQ.I.D.NO: 3. Such antibodies may further comprise a human constant region of the IgG isotype, e.g. IgG1.

In one embodiment of the invention there is provided a bispecific therapeutic antibody wherein at least one binding specificity of said antibody is for hIL-13, wherein said antibody comprises at least CDRs of SEQ.I.D.NO: 1, 2,3,4,5 and 6. Such antibodies may further comprise a human constant region of the IgG isotype, e.g. IgG1.

1.4 Antibody Fragments

In certain embodiments of the invention there is provided therapeutic antibody fragments which modulate the interaction between hIL-13 and hIL-13R. Such fragments may be functional antigen binding fragments of intact and/or humanised and/or chimaeric antibodies such as Fab, Fab', F(ab')$_2$, Fv, ScFv fragments of the antibodies described supra. Traditionally such fragments are produced by the proteolytic digestion of intact antibodies by e.g. papain digestion (see for example, WO 94/29348) but may be produced directly from recombinantly transformed host cells. For the production of ScFv, see Bird et al; (1988) Science, 242, 423-426. In addition, antibody fragments may be produced using a variety of engineering techniques as described below.

Fv fragments appear to have lower interaction energy of their two chains than Fab fragments. To stablise the association of the VH and VL domains, they have been linked with peptides (Bird et a, (1988) Science 242, 423-426, Huston et al, PNAS, 85, 5879-5883), disulphide bridges (Glockshuber et al, (1990) Biochemistry, 29,1362-1367) and "knob in hole" mutations (Zhu et al (1997), Protein Sci., 6, 781-788). ScFv fragments can be produced by methods well known to those skilled in the art see Whitlow et al (1991) Methods companion Methods Enzymol, 2, 97-105 and Huston et al (1993) Int.Rev.Immunol 10, 195-217. ScFv may be produced in bacterial cells such as *E.coli* but are more preferably produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFV containing an additional C terminal cysteine by chemical coupling (Adams et al (1993) Can.Res 53,4026-4034 and McCartney etal(1995) Protein Eng. 8,301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to 3 to 12 residues to form "diabodies", see Holliger et al PNAS (1993), 90, 6444-6448. Reducing the linker still further can result in ScFV trimers ("triabodies", see Kortt et al (1997) Protein Eng, 10, 423-433) and tetramers ("tetrabodies", see Le Gall et al (1999) FEBS Lett, 453,164-168). Construction of bivalent ScFV molecules can also be achieved by genetic fusion with protein dimerizing motifs to form "miniantibodies" (see Pack et al (1992) Biochemistry 31, 1579-1584) and "minibodies" (see Hu et al (1996), Cancer Res. 56,3055-3061). ScFv-Sc-Fv tandems ((ScFV)2) may also be produced by linking two ScFv units by a third peptide linker, see Kurucz et al (1995) J.Immol.154, 4576-4582. Bispecific diabodies can be produced through the noncovalent association of two single chain fusion products consisting of VH domain from one antibody connected by a short linker to the VL domain of another antibody, see Kipriyanov et al (1998), Int.J.Can 77,763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al (1999) J.Immunol.Methods 226 179-188. Tetravalent bispecific molecules are available by e.g. fusing a ScFv fragment to the CH3 domain of an IgG molecule or to a Fab fragment through the hinge region see Coloma et al (1997) Nature Biotechnol. 15, 159-163. Alternatively, tetravalent bispecific molecules have been created by the fusion of bispecific single chain diabodies (see Alt et al, (1999) FEBS Left 454, 90-94. Smaller tetravalent bispecific molecules can also be formed by the dimerization of either ScFv-ScFv tandems with a linker containing a helix-loop-helix motif (DiBi miniantibodies, see Muller et al (1998) FEBS Lett 432, 45-49) or a single chain molecule comprising four antibody variable domains (VH and VL) in an orientation preventing intramolecular pairing (tandem diabody, see Kipriyanov et al, (1999) J.Mol.Biol. 293, 41-56). Bispecific F(ab')$_2$ fragments can be created by chemical coupling of Fab' fragments or by heterodimerization through leucine zippers (see Shalaby et al, (1992) J.Exp.Med. 175, 217-225 and Kostelny et al (1992), J.lmmunol. 148,1547-1553). Also available are isolated VH and VL domains (Domantis plc), see U.S. Pat. Nos. 6,248,516; 6,291,158; 6, 172,197.

In one embodiment there is provided a therapeutic antibody fragment (e.g. ScFv, Fab, Fab', F(ab')$_2$) or an engineered antibody fragment as described supra that specifically binds hIL-13 and modulates (e.g. inhibits or blocks) the interaction between hIL-13 and hIL-13R. The therapeutic antibody fragment typically comprises a CDRH3 having the sequence of SEQ.I.D.NO: 3 optionally together with CDRs having the sequence set forth in SEQ.I.D.NO: 1,2,4,5 and 6.

1.5 Heteroconiugate Antibodies

Heteroconjugate antibodies also form an embodiment of the present invention. Heteroconjugate antibodies are composed of two covalently joined antibodies formed using any convenient cross-linking methods. See, for example, U.S. Pat. No. 4,676,980.

1.6 Other Modifications.

The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies of the invention may be carried out depending on the desired property. For example, specific mutations in the Fc region to render an otherwise lytic antibody, non-lytic is detailed in EP 0629 240B1 and EP 0307 434B2 or one may incorporate a salvage receptor binding epitope into the antibody to increase serum half life see U.S. Pat. No. 5,739,277. There are five currently recognised human Fcγ receptors, FcγR (I), FcγRIIa, FcγRIIb, FcγRIIIa and neonatal FcRn. Shields et al, (2001) J.Biol.Chem 276, 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRI but did not affect binding to the other receptor (e.g. Ser-267Ala improved binding to FcγRII but binding to FcγRIII was unaffected). Other variants exhibited improved binding to FcγRII or FcγRII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in both antibody clearance and the transcytosis across tissues (see Junghans R. P (1997) Immunol.Res 16. 29-57 and Ghetie et al (2000) Annu.Rev.Immunol. 18, 739-766). Human IgG1 residues determined to interact directly with human FcRn includes Ile253, Ser254, Lys288, Thr307, Gln311, Asn434 and His435. Switches at any of these positions described in this section may enable increased serum half-life and/or altered effector properties of antibodies of the invention.

Other modifications include glycosylation variants of the antibodies of the invention. Glycosylation of antibodies at conserved positions in their constant regions is known to have a profound effect on antibody function, particularly effector functioning such as those described above, see for example, Boyd et al(1996), Mol.Immunol. 32,1311-1318. Glycosylation variants of the therapeutic antibodies or antigen binding fragments thereof of the present invention wherein one or more carbohydrate moiety is added, substituted, deleted or modified are contemplated. Introduction of an asparagine-X-serine or asparagine-X-threonine motif creates a potential site for enzymatic attachment of carbonhydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1, 4-galactosyltransferace and/or alpha, 2,3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al Science (2004), 303, 371, Sears et al, Science, (2001) 291, 2344, Wacker et al (2002) Science, 298 1790, Davis et al (2002) Chem.Rev. 102, 579, Hang et al (2001) Acc.Chem.Res 34, 727. Thus the invention contemplates a plurality of therapeutic (monoclonal) antibodies (which maybe of the IgG isotype, e.g. IgG1) as herein described comprising a defined number (e.g. 7 or less, for example 5 or less such as two or a single) glycoform(s) of said antibodies or antigen binding fragments thereof.

Further embodiments of the invention include therapeutic antibodies of the invention or antigen binding fragments thereof coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis I. L. et al (2000) Int.J.Pharmaceut. 198:83-95.

2. Competing Antibodies

The present invention also contemplates antibodies and antigen binding fragments of antibodies which specifically bind hIL-13 and competitively inhibit, the binding to hIL-13 of the therapeutic antibody of the invention or antigen binding fragment thereof comprising a CDRH3 of SEQ.I.D.NO: 3 and/or a therapeutic antibody or antigen binding fragment thereof comprising CDRs of SEQ.I.D.NO: 1,2,3,4,5 and 6 to hIL-13. In some embodiments, the therapeutic antibody is the murine antibody comprising a VH domain of SEQ.I.D.NO:7 and a VL domain of SEQ.I.D.NO:8. Such competing antibodies bind to the same, overlapping or spatially adjacent epitope of hIL-13 as that bound by the therapeutic antibody comprising CDRs of SEQ.I.D.NO:1, 2,3,4,5 and 6. The competing antibody or antibody fragment displays, at equimolar concentrations, at least 25% inhibition, typically 35% or greater, more typically at least 50% inhibition.

Thus in one embodiment of the invention there is provided a method of screening a candidate antibody or antibody fragment to determine whether the candidate antibody or antibody fragment is a competing antibody as herein described which method comprises the steps of;

(a) incubating the candidate antibody or antibody fragment with a therapeutic antibody comprising CDRH3 of SEQ.I.D.NO: 3, optionally further comprising CDRs of SEQ.I.D.NO: 1,2,4,5 and 6 (such as a murine therapeutic antibody having a VH domain of SEQ.I.D.NO:7 and a VL domain of SEQ.I.D.NO:8 or a humanised therapeutic antibody having a heavy chain of SEQ.I.D.NO: 18 and a light chain of SEQ.I.D.NO:22 or a humanised therapeutic antibody having a heavy chain of SEQ.I.D.NO:19 and a light chain of SEQ.I.D.NO:23) or antigen binding fragment thereof; (b) determining whether the candidate antibody or antibody fragment thereof of step (a) competitively inhibits the binding of the therapeutic antibody or antigen binding fragment thereof to hIL-13.

There is also provided a competing antibody or antigen binding fragment thereof which competitively inhibits the binding of a therapeutic antibody or antigen binding fragment thereof which therapeutic antibody or antigen binding fragment thereof comprises CDR having the sequences set forth in SEQ.I.D.NO: 1, 2,3,4,5 and 6.

In another embodiment there is provided a competing antibody or antigen binding fragment thereof which competitively inhibits the binding of a therapeutic antibody of the invention to hIL-13 which therapeutic antibody comprises a heavy chain of SEQ.I.D.NO:18 and a light chain of SEQ.I.D.NO:22.

A competing antibody or antigen binding fragment thereof maybe of any of the above antibody structures. For example, the competing antibody may be a primate or human intact antibody or a humanised antibody preferably of an IgG isotype e.g. IgG1 or IgG4. Competing antibody fragments maybe Fab, Fab', F(ab')$_2$, ScFv and the like. A competing antibody may be produced according to the methods disclosed within this present specification.

3. Production Methods

Antibodies of the invention maybe produced as a polyclonal population but are more preferably produced as a monoclonal population (that is as a substantially homogenous population of identical antibodies directed against a specific antigenic binding site). It will of course be apparent to those skilled in the art that a population implies more than one antibody entity. Antibodies of the present invention may be produced in transgenic organisms such as goats (see Pollock et al (1999), J.Immunol.Methods 231:147-157), chickens (see Morrow K J J (2000) Genet.Eng.News 20:1-55, mice (see Pollock et al) or plants (see Doran P M, (2000) Curr.Opinion Biotechnol. 11,199-204, Ma J K-C (1998), Nat.Med. 4; 601-606, Baez J et al, BioPharm (2000) 13: 50-54, Stoger E et al; (2000) Plant Mol.Biol. 42:583-590). Antibodies may also be produced by chemical synthesis. However, antibodies of the invention are typically produced using recombinant cell culturing technology well known to those skilled in the art. A polynucleotide encoding the antibody is isolated and inserted into a replicable vector such as a plasmid for further cloning (amplification) or expression. One useful expression system is a glutamate synthetase system (such as sold by Lonza Biologics), particularly where the host cell is CHO or NS0 (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and transfected into the same host cell or, if desired both the heavy chain and light chain can be inserted into the same vector for transfection into the host cell. Thus according to one aspect of the present invention there is provided a process of constructing a vector encoding the light and/or heavy chains of a therapeutic antibody or antigen binding fragment thereof of the invention, which method comprises inserting into a vector, a polynucleotide encoding either a light chain and/or heavy chain of a therapeutic antibody of the invention.

In other aspect of the invention there is provided a polynucleotide encoding a murine VH domain having the sequence set forth as SEQ.I.D.NO:24.

In another aspect of the invention there is provided polynucleotide encoding a murine VL domain having the sequence set forth as SEQ.I.D.NO: 25.

In another embodiment there is provided a polynucletotide encoding a VH domain having the sequence selected from the group consisting of SEQ.I.D.NO:26, 27, 28, 29.

In another embodiment there is provided a polynucletotide encoding a VL domain having the sequence selected from the group consisting of; SEQ.I.D.NO:30, 31.

In accordance with the present invention there is provided a polynucleotide encoding a heavy chain of the invention which polynucleotide is selected from the group consisting of; SEQ.I.D.NO:32, 33, 34, 35.

In accordance with the present invention there is provided a polynucleotide encoding a light chain of the invention which polynucleotide is selected from the group consisting of; SEQ.I.D.NO:36, 37.

It will be immediately apparent to those skilled in the art that due to the redundancy of the genetic code, alternative polynucleotides to those disclosed herein are also available that will encode the polypeptides of the invention.

3.1 Signal Sequences

Antibodies of the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, a factor leader or acid phosphatase leaders see e.g. WO90/13646. In mammalian cell systems, viral secretory leaders such as herpes simplex gD signal and a native immunoglobulin signal sequence are available. Typically the signal sequence is ligated in reading frame to DNA encoding the antibody of the invention.

3.2 Origin of Replication

Origin of replications are well known in the art with pBR322 suitable for most gram-negative bacteria, 2 µ plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

3.3 Selection Marker

Typical selection genes encode proteins that (a) confer resistance to antibiotics or other toxins e.g. ampicillin, neomycin, methotrexate or tetracycline or (b) complement auxiotrophic deficiencies or supply nutrients not available in the complex media. The selection scheme may involve arresting growth of the host cell. Cells, which have been successfully transformed with the genes encoding the therapeutic antibody of the present invention, survive due to e.g. drug resistance conferred by the selection marker. Another example is the so-called DHFR selection marker wherein transformants are cultured in the presence of methotrexate. In typical embodiments, cells are cultured in the presence of increasing amounts of methotrexate to amplify the copy number of the exogenous gene of interest. CHO cells are a particularly useful cell line for the DHFR selection. A further example is the glutamate synthetase expression system (Lonza Biologics). A suitable selection gene for use in yeast is the trp1 gene, see Stinchcomb et al Nature 282, 38, 1979.

3.4 Promoters

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowipox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression. In one embodiment therefore there is provided a first plasmid comprising a RSV and/or SV40 and/or CMV promoter, DNA encoding light chain V region (VL) of the invention, κC region together with neomycin and ampicillin resistance selection markers and a second plasmid comprising a RSV or SV40 promoter, DNA encoding the heavy chain V region (VH) of the invention, DNA encoding the γ1 constant region, DHFR and ampicillin resistance markers 3.5 Enhancer Element Where appropriate, e.g. for expression in higher eukaroytics, an enhancer element operably linked to the promoter element in a vector may be used. Suitable mammalian enhancer sequences include enhancer elements from globin, elastase, albumin, fetoprotein and insulin. Alternatively, one may use an enhancer element from a eukaroytic cell virus such as SV40 enhancer (at bp100-270), cytomegalovirus early promoter enhancer, polyma enhancer, baculoviral enhancer or murine IgG2a locus (see WO04/009823). The enhancer is preferably located on the vector at a site upstream to the promoter.

3.6 Host Cells

Suitable host cells for cloning or expressing vectors encoding antibodies of the invention are prokaroytic, yeast or higher eukaryotic cells. Suitable prokaryotic cells include eubacteria e.g. enterobacteriaceae such as *Escherichia* e.g. *E.coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as Bacilli such as *B.subtilis* and *B.licheniformis* (see DD 266 710), *Pseudomonas* such as *P.aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), yarrowia (EP402, 226), *Pichia Pastoris* (EP183, 070, see also Peng et al J.Biotechnol. 108 (2004) 185-192), *Candida, Trichoderma reesia* (EP244, 234), *Penicillin, Tolypocladium* and *Aspergillus* hosts such as *A.nidulans* and *A.niger* are also contemplated.

Although Prokaryotic and yeast host cells are specifically contemplated by the invention, preferably however, host cells of the present invention are higher eukaryotic cells. Suitable higher eukaryotic host cells include mammalian cells such as COS-1 (ATCC No.CRL 1650) COS-7 (ATCC CRL 1651), human embryonic kidney line 293, baby hamster kidney cells (BHK) (ATCC CRL.1632), BHK570 (ATCC NO: CRL 10314), 293 (ATCC NO.CRL 1573), Chinese hamster ovary cells CHO (e.g. CHO-K1, ATCC NO: CCL 61, DHFR-CHO cell line such as DG44 (see Urlaub et al, (1986) Somatic Cell Mol.Genet.12, 555-556)), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0. Thus in one embodiment of the invention there is provided a stably transformed host cell comprising a vector encoding a heavy chain and/or light chain of the therapeutic antibody or antigen binding fragment thereof as herein described. Preferably such host cells comprise a first vector encoding the light chain and a second vector encoding said heavy chain.

Bacterial Fermentation

Bacterial systems are particularly suited for the expression of antibody fragments. Such fragments are localised intracellularly or within the periplasma. Insoluble periplasmic proteins can be extracted and refolded to form active proteins according to methods known to those skilled in the art, see Sanchez et al (1999) J.Biotechnol. 72, 13-20 and Cupit P M et al (1999) Lett Appl Microbiol, 29, 273-277.

3.7 Cell Culturing Methods.

Host cells transformed with vectors encoding the therapeutic antibodies of the invention or antigen binding fragments thereof may be cultured by any method known to those skilled in the art. Host cells may be cultured in spinner flasks, roller bottles or hollow fibre systems but it is preferred for large scale production that stirred tank reactors are used particularly for suspension cultures. Preferably the stirred tankers are adapted for aeration using e.g. spargers, baffles or low shear impellers. For bubble columns and airlift reactors direct aeration with air or oxygen bubbles maybe used. Where the host cells are cultured in a serum free culture media it is preferred that the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly invertebrate host cells may utilise a variety of operational modes such as fed-batch, repeated batch processing (see Drapeau et al (1994) cytotechnology 15: 103-109), extended batch process or perfusion culture. Although recombinantly transformed mammalian host cells may be cultured in serum-containing media such as fetal calf serum (FCS), it is preferred that such host cells are cultured in synthetic serum-free media such as disclosed in Keen et al (1995) Cytotechnology 17:153-163, or commercially available media such as ProCHO-CDM or Ultra-CHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in *Animal Cell technology: Developments towards the 21st century* (Beuvery E. C. et al eds), pp619-623, Kluwer Academic publishers).

Antibodies of the invention secreted into the media may be recovered and purified using a variety of techniques to provide a degree of purification suitable for the intended use. For example the use of therapeutic antibodies of the invention for the treatment of human patients typically mandates at least 95% purity, more typically 98% or 99% or greater purity (compared to the crude culture medium). In the first instance, cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (preferably monoclonal) preparation comprising at least 75 mg/ml or greater e.g. 100 mg/ml or greater of the antibody of the invention or antigen binding fragment thereof is provided and therefore forms an embodiment of the invention. Suitably such preparations are substantially free of aggregated forms of antibodies of the invention.

4. Pharmaceutical Compositions

Purified preparations of antibodies of the invention (particularly monoclonal preparations) as described supra, may be incorporated into pharmaceutical compositions for use in the treatment of human diseases and disorders such as atopic diseases e.g. asthma, allergic rhinitis, COPD. Typically such compositions comprise a pharmaceutically acceptable carrier as known and called for by acceptable pharmaceutical practice, see e.g. Remingtons Pharmaceutical Sciences, 16th edition, (1980), Mack Publishing Co. Examples of such carriers include sterilised carrier such as saline, Ringers solution or dextrose solution, buffered with suitable buffers to a pH within a range of 5 to 8. Pharmaceutical compositions for injection (e.g. by intravenous, intraperitoneal, intradermal, subcutaneous, intramuscular or intraportal) or continuous infusion are suitably free of visible particulate matter and may comprise between 0.1 ng to 100 mg of antibody, preferably between 5 mg and 25 mg of antibody. Methods for the preparation of such pharmaceutical compositions are well known to those skilled in the art. In one embodiment, pharmaceutical compositions comprise between 0.1 ng to 100 mg of therapeutic antibodies of the invention in unit dosage form, optionally together with instructions for use. Pharmaceutical compositions of the invention may be lyophilised (freeze dried) for reconstitution prior to administration according to methods well known or apparent to those skilled in the art. Where embodiments of the invention comprise antibodies of the invention with an IgG1 isotype, a chelator of copper such as citrate (e.g. sodium citrate) or EDTA or histidine may be added to pharmaceutical composition to reduce the degree of copper-mediated degradation of antibodies of this isotype, see EP0612251. Anti-hIL-13 treatment maybe given orally, by inhalation, topically (for example, intraocular, intransnasal, rectal into wounds on the skin).

Effective doses and treatment regimes for administering the antibody of the invention are generally determined empirically and are dependent on factors such as the age, weight and health status of the patient and disease or disorder to be treated. Such factors are within the purview of the attending physician. Guidance in selecting appropriate doses may be found in e.g. Smith et al (1977) Antibodies in human diagnosis and therapy, Raven Press, New York but will in general be between 1 mg and 1000 mg.

Depending on the disease or disorder to be treated (but particularly asthma), pharmaceutical compositions comprising a therapeutically effective amount of the antibody of the invention may be used simultaneously, separately or sequentially with an effective amount of another medicament such as anti-inflammatory agents (e.g. corticosteroid or an NSAID), anticholinergic agents (particularly M1/M2/M3 receptor antagonists), $\beta_2$ adrenoreceptor agonists, antiinfective agents (e.g. antibiotics, antivirals), antihistamines, PDE4 inhibitor. Examples of $\beta_2$ adrenoreceptor agonists include salmeterol, salbutamol, formoterol, salmefamol, fenoterol, terbutaline. Preferred long acting $\beta_2$ adrenoreceptor agonists include those described in WO02/66422A, WO02/270490, WO02/076933, WO03/024439 and WO03/072539. Suitable corticosteroids include methyl prednisolone, prednisolone, dexamethasone, fluticasone propionate, 6α, 9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (eg. the 17-propionate ester or the 17,21-dipropionate ester), budesonide, flunisolide, mometasone esters (eg. the furoate ester), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-1 26. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds having glucocorticoid agonism that may posess selectivity for transrepression over transactivation and that may be useful in combination therapy include those covered in the following patents: WO03/082827, WO01/1 0143, WO98/54159, WO04/005229, WO04/009016, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277.

Suitable anti-inflammatory agents include non-steroidal anti-inflammatory drugs (NSAID's).

Suitable NSAID's include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis (eg. montelukast), iNOS inhibitors, tryptase and elastase inhibitors, beta-2 integrin antagonists and adenosine receptor agonists or antagonists (e.g. adenosine 2a agonists), cytokine antagonists (e.g. chemokine antagonists, such as a CCR3 antagonist) or inhibitors of cytokine synthesis, or 5-lipoxygenase inhibitors. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

Of particular interest is use of the antibodies of the invention in combination with a phosphodiesterase 4 (PDE4) inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 03 Sep., 1996; this patent and the compounds it discloses are incorporated herein in full by reference.

AWD-12-281 from Elbion (Hofgen, N. et al. 15th EFMC Int Symp Med Chem (Sept 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-1 1294A from Napp (Landells, L. J. et al. Eur Resp J [Annu Cong Eur Resp Soc (Sept 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*, 10bS*)-9-ethoxy-1 ,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds of interest are disclosed in the published international patent application WO04/024728 (Glaxo Group Ltd), PCT/EP2003/014867 (Glaxo Group Ltd) and PCT/EP2004/005494 (Glaxo Group Ltd).

Suitable anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (e.g. as the bromide, CAS 22254-24-6, sold under the name Atrovent), oxitropium (e.g. as the bromide, CAS 30286-75-0) and tiotropium (e.g. as the bromide, CAS 136310-93-5, sold under the name Spiriva). Also of interest are revatropate (e.g. as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (e.g. as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other suitable anticholinergic agents include compounds of formula (XXI), which are disclosed in US patent application 60/487981:

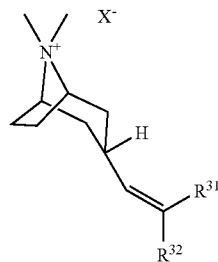

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom.

$X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further suitable anticholinergic agents include compounds of formula (XXII) or (XXIII), which are disclosed in US patent application 60/511009:

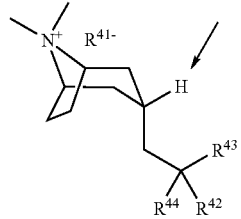

(XXII)

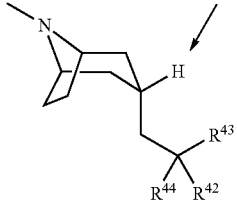

(XXIII)

wherein:

the H atom indicated is in the exo position;

$R^{41-}$ represents an anion associated with the positive charge of the N atom. $R^{1-}$ may be but is not limited to chloride, bromide, iodide, sulfate, benzene sulfonate and toluene sulfonate;

$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to10 carbon atoms) and N or O as the heteroatom, aryl, optionally substituted aryl, heteroaryl, and optionally substituted heteroaryl;

$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —CN, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CO(R^{46})$, —$CH_2N(R^{48})SO_2(R^{46})$, —$CH_2N(R^{48})CO_2(R^{45})$, —$CH_2N(R^{48})CONH(R^{47})$;

$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;

$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;

$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:

(Endo)-3-(2-methoxy-2 ,2-di-thiophen-2-yl-ethyl)-8,8-dimethyl-8-azonia-bicyclo[3.2.1]octane iodide;

3-((Endo)-8-methyl-8-aza-bicyclo[3.2.1]oct-3-yl)-2,2-diphenyl-propionitrile;

(Endo)-8-methyl-3-(2,2,2-triphenyl-ethyl)-8-aza-bicyclo[3.2.1]octane;

3-((Endo)-8-methyl-8-aza-bicyclo[3.2.1]oct-3-yl)-2,2-diphenyl-propionamide;

3-((Endo)-8-methyl-8-aza-bicyclo[3.2.1]oct-3-yl)-2,2-diphenyl-propionic acid;

(Endo)-3-(2-cyano-2,2-diphenyl-ethyl)-8,8-dimethyl-8-azonia-bicyclo[3.2.1]octane iodide;

(Endo)-3-(2-cyano-2,2-diphenyl-ethyl)-8,8-dimethyl-8-azonia-bicyclo[3.2.1]octane bromide;

3-((Endo)-8-methyl-8-aza-bicyclo[3.2.1]oct-3-yl)-2,2-diphenyl-propan-1-ol;

N-Benzyl-3-((endo)-8-methyl-8-aza-bicyclo[3.2.1]oct-3-yl)-2,2-diphenyl-propionamide;

(Endo)-3-(2-carbamoyl-2,2-diphenyl-ethyl)-8,8-dimethyl-8-azonia-bicyclo[3.2.1]octane iodide;

1-Benzyl-3-[3-((endo)-8-methyl-8-aza-bicyclo[3 .2.1 ]oct-3-yl)-2,2-diphenyl-propyl]-urea;

1-Ethyl-3-[3-((endo)-8-methyl-8-aza-bicyclo[3.2.1]oct-3-yl)-2,2-diphenyl-propyl]-urea;

N-[3-((Endo)-8-methyl-8-aza-bicyclo[3.2.1]oct-3-yl)-2,2-diphenyl-propyl]-acetamide;

N-[3-((Endo)-8-methyl-8-aza-bicyclo[3.2.1]oct-3-yl)-2,2-diphenyl-propyl]-benzamide;

3-((Endo)-8-methyl-8-aza-bicyclo[3.2.1]oct-3-yl)-2,2-dithiophen-2-yl-propionitrile;

(Endo)-3-(2-cyano-2,2-di-thiophen-2-yl-ethyl)-8,8-dimethyl-8-azonia-bicyclo[3.2.1]octane iodide;

N-[3-((Endo)-8-methyl-8-aza-bicyclo[3.2.1]oct-3-yl)-2,2-diphenyl-propyl]-benzenesulfonamide;

[3-((Endo)-8-methyl-8-aza-bicyclo[3.2.1]oct-3-yl)-2,2-diphenyl-propyl]-urea;

N-[3-((Endo)-8-methyl-8-aza-bicyclo[3.2.1]oct-3-yl)-2,2-diphenyl-propyl]-methanesulfonamide; and/or (Endo)-3-{2,2-diphenyl-3-[(1-phenyl-methanoyl)-amino]-propyl}-8,8-dimethyl-8-azonia-bicyclo[3.2.1]octane bromide.

More preferred compounds useful in the present invention include:

(Endo)-3-(2-methoxy-2,2-di-thiophen-2-yl-ethyl)-8,8-dimethyl-8-azonia-bicyclo[3.2.1]octane iodide;

(Endo)-3-(2-cyano-2,2-diphenyl-ethyl)-8,8-dimethyl-8-azonia-bicyclo[3.2.1]octane iodide;

(Endo)-3-(2-cyano-2,2-diphenyl-ethyl)-8,8-dimethyl-8-azonia-bicyclo[3.2.1]octane bromide;

(Endo)-3-(2-carbamoyl-2,2-diphenyl-ethyl)-8,8-dimethyl-8-azonia-bicyclo[3.2.1]octane iodide;

(Endo)-3-(2-cyano-2,2-di-thiophen-2-yl-ethyl)-8,8-dimethyl-8-azonia-bicyclo[3.2.1]octane iodide; and/or (Endo)-3-{2,2-diphenyl-3-[(1-phenyl-methanoyl)-amino]-propyl}-8,8-dimethyl-8-azonia-bicyclo[3.2.1]octane bromide.

Suitable antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, e.g diphenylhydramine, pyrilamine, clemastine, chlropheniramine. Second generation antagonists, which are non-sedating, include loratidine, desloratidine,terfenadine,astemizole,acrivastine, azelastine, levocetirizine fexofenadine and cetirizine.

Examples of preferred anti-histamines include loratidine, desloratidine, fexofenadine and cetirizine.

Other contemplated combinations include the use of antibodies of the invention in combination with an anti-IL-4 agent (e.g. anti-IL-4 antibody such as pascolizumab) and/or anti-IL-5 agent (e.g. anti-IL-5 antibody such as mepolizumab) and/or anti-IgE agent (e.g. anti-IgE antibody such as omalizumab (Xolair™) or talizumab).

Conveniently, a pharmaceutical composition comprising a kit of parts of the antibody of the invention or antigen binding fragment thereof together with such another medicaments optionally together with instructions for use is also contemplated by the present invention.

The invention furthermore contemplates a pharmaceutical composition comprising a therapeutically effective amount of monoclonal therapeutic antibody or antigen binding fragment thereof as herein described for use in the treatment of diseases responsive to modulation of the interaction between hIL-13 and hIL-13R.

In accordance with the present invention there is provided a pharmaceutical composition comprising a therapeutically effective amount of a monoclonal humanised therapeutic antibody which antibody comprises a VH domain selected from the group consisting of: SEQ.I.D.NO:11,12,13,14 and a VL domain selected from the group consisting of: SEQ.I.D.NO:15,16.

In accordance with the present invention there is provided a pharmaceutical composition comprising a monoclonal therapeutic antibody comprising a heavy chain selected from the group consisting of: SEQ.I.D.NO: 18,19,20,21 and a light chain selected from the group consisting of; SEQ.I.D.NO:22, 23.

In accordance with the present invention there is provided a pharmaceutical composition comprising a monoclonal therapeutic antibody comprising a heavy chain of SEQ.I.D.NO:18 and a light chain of SEQ.I.D.NO:22 and a pharmaceutically acceptable carrier.

In accordance with the present invention there is provided a pharmaceutical composition comprising a monoclonal antibody comprising (or consisting essentially of) a heavy chain of SEQ.I.D.NO:18 and a light chain of SEQ.I.D.NO:22 and a pharmaceutically acceptable carrier.

In accordance with the present invention there is provided a pharmaceutical composition comprising a pharmaceutically acceptable carrier and a therapeutically effective amount of a monoclonal population of therapeutic antibody which therapeutic antibody comprises a heavy chain of SEQ.I.D.NO:18 and a light chain of SEQ.I.D.NO:22.

5. Clinical Uses.

Antibodies of the invention may be used in the treatment of atopic diseases/ disorders and chronic inflammatory diseases/ disorders. Of particular interest is their use in the treatment of asthma, such as allergic asthma, particularly severe asthma (that is asthma that is unresponsive to current treatment, including systemically administered corticosteroids; see Busse W W et al, J Allergy Clin. Immunol 2000, 106: 1033-1042), "difficult" asthma (defined as the asthmatic phenotype characterised by failure to achieve control despite maximally recommended doses of prescribed inhaled steroids, see Barnes P J (1998), Eur Respir J 12:1208-1218), "brittle" asthma (defines a subgroup of patients with severe, unstable asthma who maintain a wide peak expiratory flow (PEF) variability despite high doses of inhaled steroids, see Ayres J G et al (1998) Thorax 58:315-321), nocturnal asthma, premenstrual asthma, steroid resistant asthma (see Woodcock A J (1993) Eur Respir J 6:743-747), steroid dependent asthma (defined as asthma that can be controlled only with high doses of oral steroids), aspirin induced asthma, adult-onset asthma, paediatric asthma . Antibodies of the invention maybe used to prevent, reduce the frequency of, or mitigate the effects of acute, asthmatic episodes (status asthmaticus). Antibodies of the invention may also be used to reduce the dosing required (either in terms of amount administered or frequency of dosing) of other medicaments used in the treatment of asthma. For example, antibodies of the invention may be used to reduce the dosing required for steroid treatment of asthma such as corticosteroid treatment ("steroid sparing"). Other diseases or disorders that may be treated with antibodies of the invention include atopic dermatitis, allergic rhinitis, Crohn's disease, chronic obstructive pulmonary disease (COPD), eosinophilic esophagitis, fibrotic diseases or disorders such as idiopathic pulmonary fibrosis, progressive systemic sclerosis (scleroderma), hepatic fibrosis, hepatic granulomas, schistosomiasis, leishmaniasis, and diseases of cell cycle regulation, e.g. Hodgkins disease, B cell chronic lymphocytic leukaemia. Further diseases or disorders that may be treated with antibodies of the invention are detailed in the Background of the invention section above.

In one embodiment of the invention there is provided a method of treating a human patient afflicted with an asthmatic condition which is refractory to treatment with corticosteroids which method comprises the step of administering to said patient a therapeutically effective amount of an antibody of the invention.

In another embodiment there is provided a method of preventing an acute asthmatic attack in a human patient which method comprises the step of administering to said patient a therapeutically effective amount of an antibody of the invention.

In another embodiment there is provided a method of reducing the frequency of and/or mitigating the effects of an acute asthmatic attack in a human patient which method comprises the step of administering to said patient a therapeutically effective amount of an antibody of the invention.

In another embodiment of the invention there is provided a method of biasing T helper cell response towards a Th1 type response following an inflammatory and/or allergic insult in a human patient which method comprises administering to said patient a therapeutically effective amount of an antibody or antigen binding fragment thereof of the invention.

In another embodiment of the invention there is provided a method of treating a human patient having the Q130hIL-13 variant which patient is afflicted with asthma, such as severe asthma, said method comprising the step of administering to said patient a therapeutically effective amount of an antibody or antigen binding fragment thereof of the invention.

Although the present invention has been described principally in relation to the treatment of human diseases or disorders, the present invention may also have applications in the treatment of similar diseases or disorders in non-human mammals.

The present invention is now described by way of example only.

Exemplification

1. Generation of Monoclonal Antibodies and Characterisation of Mouse Monoclonal Antibodies 6A1

Monoclonal antibodies (mAbs) are produced by hybridoma cells generally in accordance with the method set forth in E Harlow and D Lane, Antibodies a Laboratory Manual, Cold Spring Harbor Laboratory, 1988. The result of the fusion of mouse myeloma cells with B-lymphocytes from mice immunised with the target antigen. The hybridoma cell is immortalised by the myeloma fusion partner while the capacity to produce antibodies is provided by the B lymphocyte.

Five SJL mice were immunised by intraperitoneal injection each with 2 µg recombinant human IL-13 derived from *E.coli* (Cambridge Bioscience, Cat. No. CH-013). An immunisation schedule was used to develop a high titre anti-human IL-13 antibody immune response in the mice. After 5 immunisations over 64 days, the mice were culled and spleen cells harvested. Spleen cells from 3 of the mice were removed and B lymphocytes fused with mouse myeloma cells derived from P3X cells using PEG1500 (Boehringer) to generate hybridomas. Individual hybridoma cell lines were cloned by limiting dilution (E Harlow and D Lane, supra). Wells containing single colonies were identified microscopically and supernatants tested for activity. Cells from the most active clones were expanded for cryopreservation, antibody production etc.

Initially, hybridoma supernatants were screened for binding activity against an *E.coli*-expressed recombinant det-1 tagged human IL-13 protein (made in-house) in a sandwich assay format. A secondary screen of these positives was completed using a BIAcore™ method to detect for binding to the det-1 tagged human IL-13 protein. Samples from these hybridomas were then tested for ability to neutralise the bioactivity of *E.coli*-expressed recombinant human IL-13 (Cambridge Bioscience, cat. no CH-013) in a TF-1 cell bioassay.

Six positives identified from the human IL-13 neutralising bioassay were subcloned by limiting dilution to generate stable monoclonal cell lines. Immunoglobulins from these hybridomas, grown in cell factories under serum free conditions, were purified using immobilised Protein A columns. These purified mAbs were then re-screened in the following assay systems;

Binding to *E.coli*-expressed recombinant human IL-13 (in a sandwich ELISA format)

Inhibition of *E.coli*-expressed recombinant det-1 tagged human IL-13 binding to both IL-13 receptor chains (in a sandwich ELISA format)

Neutralisation of either human or cynomolgus *E.coli*-expressed recombinant IL-13 (in a TF-1 cell bioassay)

Neutralisation of mammalian-expressed human IL-13 (in a TF-1 cell bioassay)

Neutralisation of an *E.coli*-expressed recombinant Q130 human IL-13 variant (in a TF-1 cell bioassay)

Specificity for binding to human IL-13 by assessment of mAb cross-reactivity to human IL-4 in an anti-IL-4 ELISA and assessment of mAb cross-reactivity to human IL5 in an IL5 neutralisation bioassay BIAcore™ analysis for binding affinity measurements to human IL-13

Monoclonal antibody 6A1 was identified as an antibody that neutralised both human and cynomolgus IL-13 bioactivity. The following analyses describe the profile for monoclonal antibody 6A1 in these assays.

1.1 Binding to *E.coli*-expressed Recombinant Human IL-13

6A1 bound *E.coli*-expressed recombinant human IL-13 in a sandwich ELISA, method substantially as described in section 7. See FIG. 1.

Figure 2A:
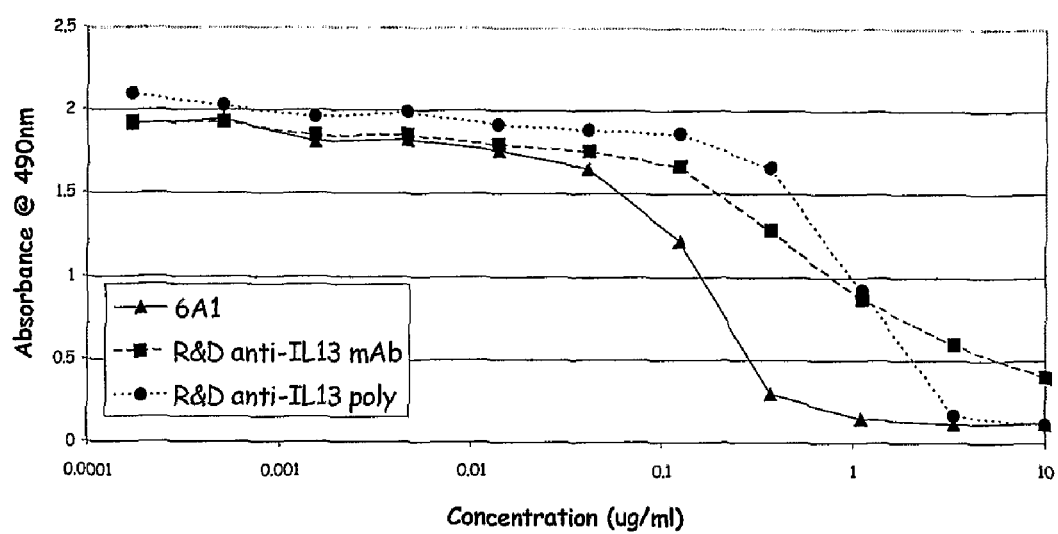
FIG. 2A
ELISA illustrating the ability of monoclonal antibody 6A1 at increasing concentrations to inhibit recombinant *E.coli*-expressed human IL-13 binding to the human IL-13 receptor α1 chain.
Figure 2B:
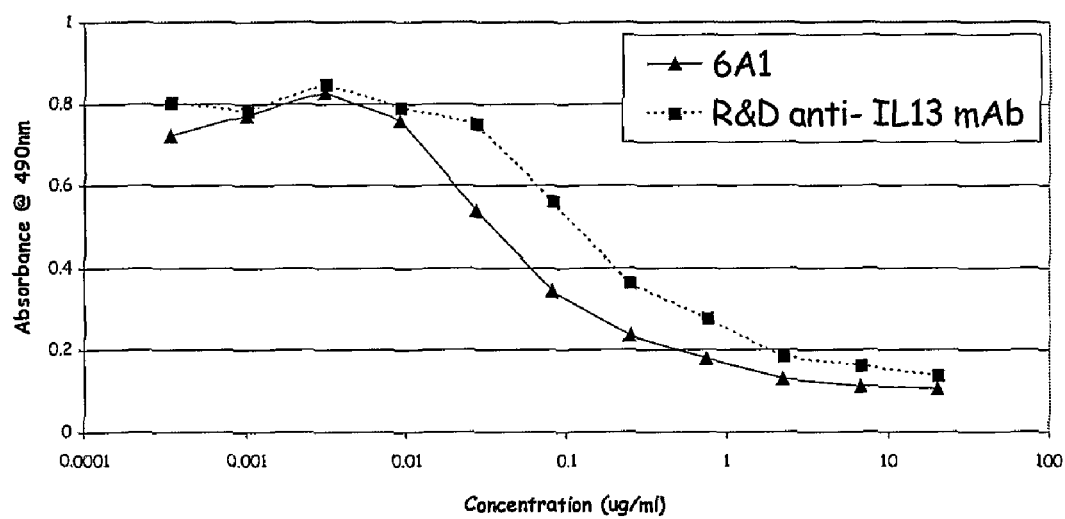
FIG. 2B
ELISA illustrating the ability of monoclonal antibody 6A1 at increasing concentrations to inhibit recombinant *E.coli*-expressed human IL-13 binding to the human IL-13 receptor α2 chain.

1.2 Inhibition of *E.coli*-expressed Recombinant det-1 Tagged Human IL-13 Binding to IL-13Rα1 and IL-13Rα2 in an ELISA Format 6A1 inhibited the binding of *E.coli*-expressed recombinant det-1 tagged human IL-13 to both human IL-13 receptor chains. In addition, it inhibited binding more effectively than a commercially available anti-human IL-13 polyclonal and an anti-human IL-13 monoclonal antibody reagent (sourced from R&D Systems). An $IC_{50}$ value of 0.1 65 μg/ml was calculated for the inhibition of human IL-13 binding to human IL-13Rα1 by monoclonal antibody 6A1. An $IC_{50}$ value of 0.056 μg/ml was calculated for the inhibition of human IL-13 binding to human IL-13Rα2 by monoclonal antibody 6A1. See FIGS. 2A and 2B. A control IgG of irrelevant specificity had no detectable activity.

Figure 3:
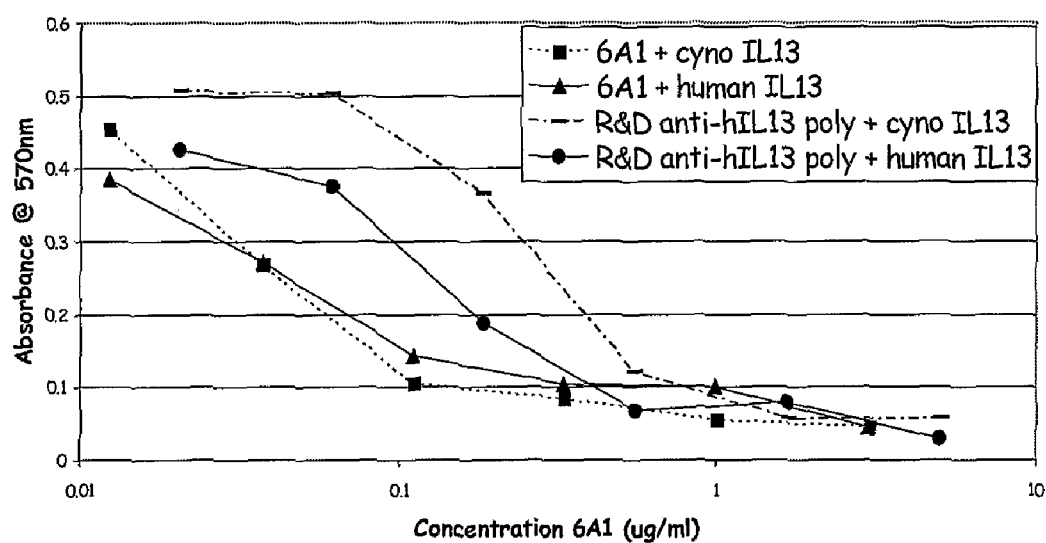
FIG. 3
Neutralisation assay illustrating the ability of 6A1 at increasing concentrations to inhibit the bioactivity of recombinant *E.coli*-expressed human and cynomolgus in a TF-1 cell proliferation assay.

1.3 Neutralisation of *E.coli*-expressed Recombinant Human and Cynomolgus IL-13 in a TF-1 Cell Proliferation Bioassay TF-1 cells can proliferate in response to human IL-13 and cynomolgus IL-13. A bioassay was developed to assess the neutralisation capacity of an anti-IL-13 mAb on human and cynomolgus IL-13-induced TF-1 cell proliferation. 6A1 neutralised the bioactivty of both recombinant human and cynomolgus IL-13 in a TF-1 cell bioassay. In addition, it neutralised both human and cynomolgus IL-13 more potently than commercially available anti-human IL-13 polyclonal and anti-human IL-13 monoclonal antibody reagents (sourced from R&D Systems). See FIG. 3.

An average $ND_{50}$ value of 0.0783pg/ml was calculated for the neutralisation of 5 ng/ml *E. coli*-expressed recombinant human IL-13 bioactivity in a TF-1 cell bioassay by monoclonal antibody 6A1. An $ND_{50}$ value of 0.04 μg/ml was calculated for the neutralisation of 5 ng/ml *E.coli*-expressed recombinant cynomolgus IL-13 bioactivity in a TF-1 cell bioassay by monoclonal antibody 6A1. [The $ND_{50}$ (neutralisation dose) value is the concentration of monoclonal antibody required to reduce TF-1 cell proliferation by 50%, in response to a set concentration of IL-13].

Figure 4:
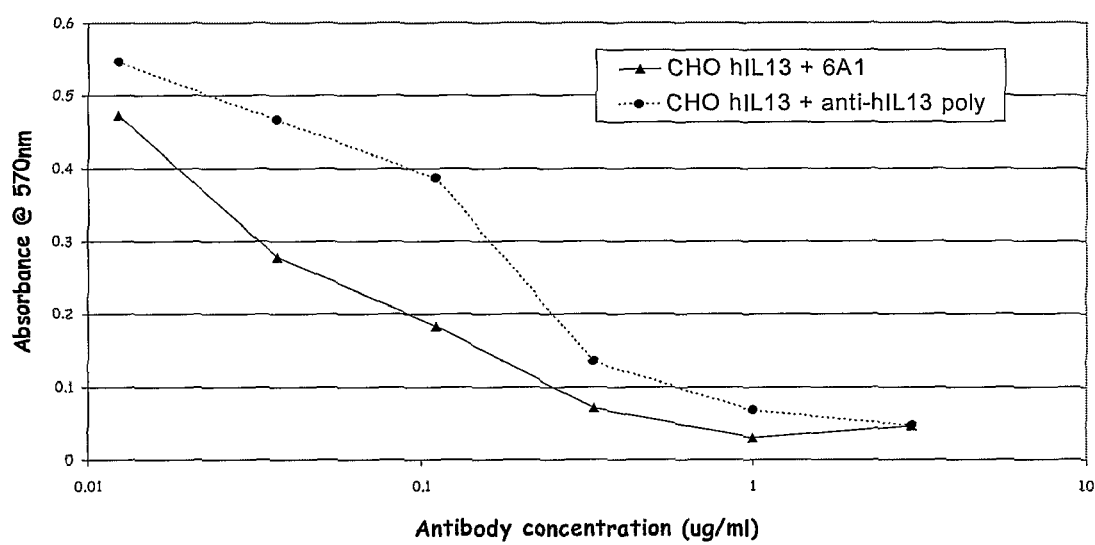
FIG. 4
Neutralisation assay illustrating the ability of 6A1 at increasing concentrations to inhibit the bioactivity of mammalian-expressed (CHO cell) human IL-13 in a TF-1 cell proliferation assay.

1.4 Neutralisation of Mammalian-expressed (CHO Cell) Human IL-13 in a TF-1 Cell Proliferation Bioassay The neutralisation capacity of monoclonal antibody 6A1 for human IL-13 expressed from CHO cells was assessed in a TF-1 cell proliferation assay. 6A1 neutralised mammalian-expressed human IL-13 more potently than a commercially available anti-human IL-13 polyclonal reagent as measured by $ND_{50}$ values. An $ND_{50}$ value of 0.037 μg/ml was calculated for the neutralisation of ~50 ng/mi mammalian-expressed human IL-13 in a TF-1 cell bioassay by monoclonal antibody 6A1. See FIG. 4.

Figure 5:
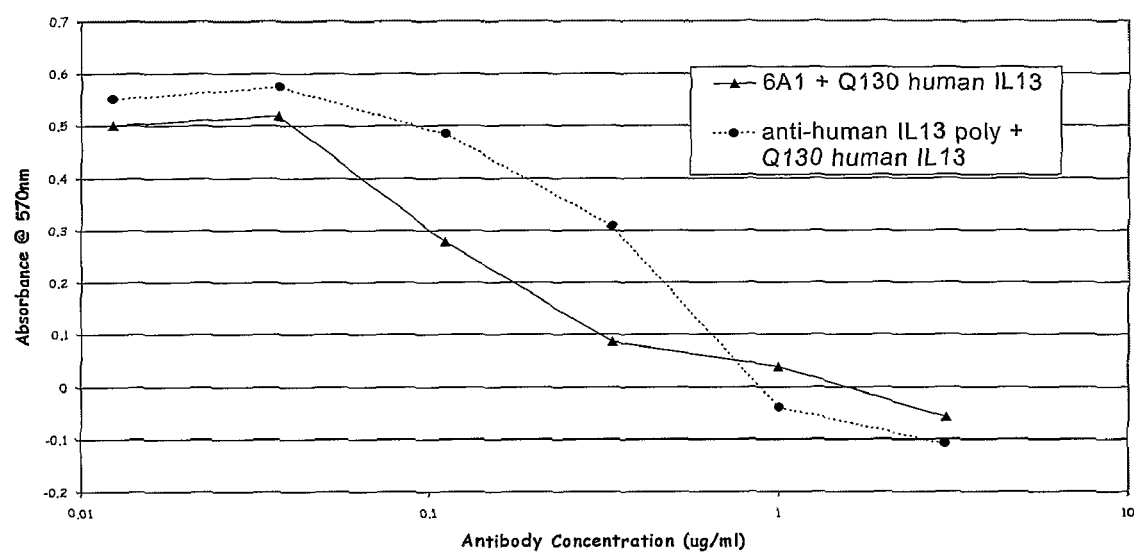
FIG. 5
Neutralisation assay illustrating the ability of 6A1 at increasing concentrations to inhibit the bioactivity of recombinant *E.coli*-expressed Q130 human IL-13 in a TF-1 cell proliferation assay.

1.5 Neutralisation of Recombinant Q130 Human IL-13 Variant in a TF-1 Cell Proliferation Bioassay The neutralisation capacity of monoclonal antibody 6A1 for *E.coli*-expressed recombinant Q130 human IL-13 (Peprotech, Cat. No. 200-13A) was assessed in a TF-1 cell proliferation assay. 6A1 neutralised Q130 human IL-13 more potently than a commercially available anti-human IL-13 polyclonal reagent. An $ND_{50}$ value of 0.11 μg/ml was calculated for the neutralisation of 60 ng/ml Q130 human IL-13 bioactivity in a TF-1 cell bioassay by monoclonal antibody 6A1. See FIG. 5.

1.6 Specificity for Binding to Human IL-13

Figure 6:
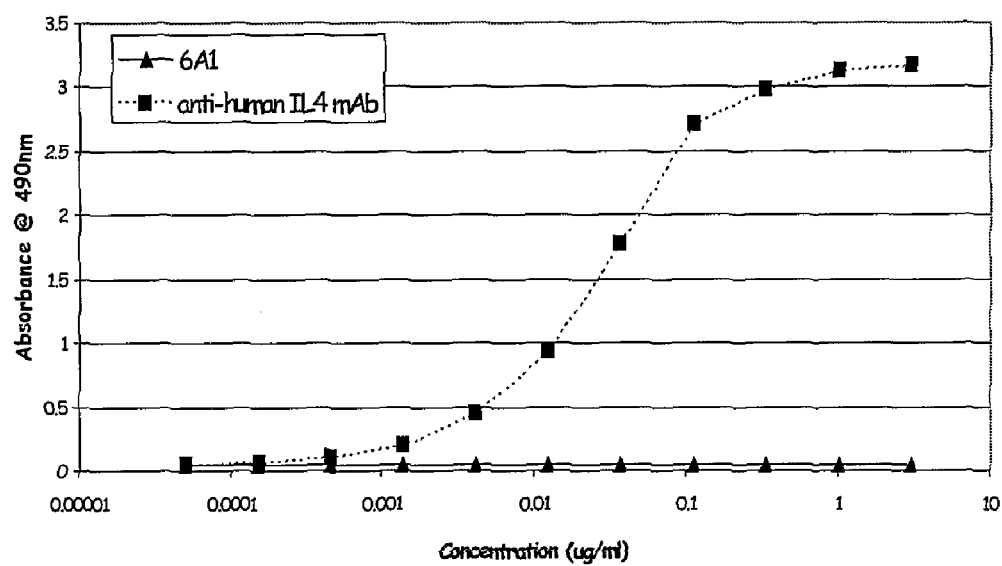
FIG. 6
Sandwich ELISA demonstrating that 6A1 does not bind recombinant *E.coli*-expressed human IL-4.
Figure 7:
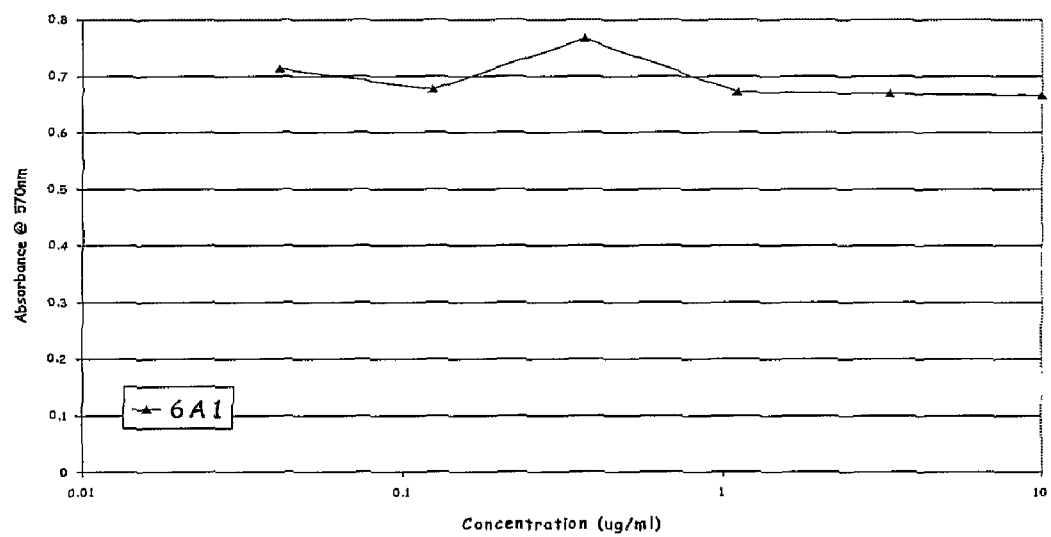
FIG. 7
An IL5 neutralisation assay, demonstrating that 6A1 does not inhibit the bioactivity of recombinant *E.coli*-expressed human IL-5 in a TF-1 cell proliferation assay.

As human IL-4 shares the most identity with human IL-13 both structurally and functionally, the specificity of monoclonal antibody 6A1 for human IL-13 was assessed in a human IL-4 binding ELISA. 6A1 did not detectably bind *E.coli*-expressed recombinant human IL-4, indicating the high level of specificity of this monoclonal antibody for human IL-13. In addition, 6A1 did not detectably cross-neutralise the bioactivity of *E.coli*-expressed recombinant human IL5 in a TF-1 cell bioassay. See FIGS. 6 and 7.

1.7 BIAcore™ Analysis

The affinity of 6A1 for recombinant human and cynomolgus IL-13 was assessed by BIAcore™ analysis. See Table 1.

TABLE 1

| IL13 sample | On rate Ka (1/Ms) | Off rate Kd (1/s) | Affinity constant (KD) |
|---|---|---|---|
| det-1 tagged human IL13 | $2.25 \times 10^6$ | $7.2 \times 10^{-5}$ | 32 pM |
| human IL13 (CA) | $6.82 \times 10^5$ | $1.84 \times 10^{-4}$ | 270 pM |
| cyno IL13 (CA) | $9.14 \times 10^5$ | $5.6 \times 10^{-5}$ | 61.2 pM |

These data indicate that 6A1 has an affinity for both human and cynomolgus IL-13. [Two different human IL-13 samples (both generated in *E.coli*) were used for this analysis. IL-13 is substantially insoluble when produced in *E.coli* but can be solubilised and then refolded in vitro. Differences in the quality of the two refolded IL-13 samples may explain the difference in binding affinities for each of these human IL-13 samples].

2. Cloning of Variable Regions of Clone 6A1

Total RNA was extracted from clone 6A1 hybridoma cells and the cDNA of the heavy and light variable domains was produced by reverse transcription using primers specific for the murine leader sequence and the antibody constant regions according to the pre-determined isotype (IgG1/κ). The cDNA of the variable heavy and light domains was then cloned into vector pCR2.1 for sequencing.

2.1 RNA Extraction

Total RNA was extracted from pellets of approximately $10^6$ cells of hybridoma clone 6A1 using the SV Total RNA Isolation System from Promega according to manufacturer's instructions.

2.2 Reverse Transcription

RNA was reverse transcribed to produce cDNA of the variable heavy and light domains using primers specific for the murine leader sequences and murine IgG1/κ constant regions. The mixture of primers used is set forth in Jones S T and Bendig M M Bio/technology 9:88-89 (1991)

Pools of murine $V_H$ and $V_L$ leader sequence forward primers were prepared at 50 μM. Solutions of the murine IgG1 and κ constant region reverse primers were also prepared at 50 μM.

2.3 Reverse Transcription PCR (RT-PCR)

Reverse transcription of the RNA encoding the variable heavy and light regions were carried out in duplicates using the Access RT-PCR System from Promega according to manufacturer's instructions. VH and VL forward and reverse primers were as described above.

2.4 Gel Purification of RT-PCR Product

The products of RT-PCR ($2\times V_H$ and $2\times V_L$) were loaded in gel loading solution on a preparative 1% agarose gel containing 0.01% ethidium bromide and run in TAE buffer at 100V for 1 hour and the V region bands excised. A 100 bp DNA ladder was also run on the gel to allow identification of the $V_H$ and $V_L$ bands.

The DNA fragments were extracted and purified from the gel using the QIAquick ™Gel extraction kit from Qiagen according to manufacturer's instructions.

2.5 Ligation

The purified RT-PCR fragments ($2\times V_H$ and $2\times V_L$) were cloned into the pCR2.1 vector using the TA cloning kit from Invitrogen according to manufacturer's instructions.

2.6 Transformation

Ligated plasmids were transformed into TOP10F' cells according to TA cloning kit instructions. 50 μl and 200 μl of transformed cells were spread oh L-agar plates containing 100 μg/ml ampicillin and coated with 8 μl of 500 mM IPTG solution and 16 μl of 50 mg/ml X-Gal solution in DMF. Plates were incubated overnight at 37° C.

2.7 Sequencing

Colonies were picked and cultured overnight at 37° C. in 5 ml LB medium supplemented with 100 μg/ml ampicillin.

pCR2.1 plasmids containing 6A1 $V_H$ and $V_L$ domains were extracted and purified using the Qiagen QIAprep Spin Miniprep kit according to manufacturer's instructions. The $V_H$ and $V_L$ domains were sequenced using primers T7, M13 forward and M13 reverse.

6A1 $V_H$ region amino acid sequence (consensus of 10 clones from 2 RT-PCR reactions):

SEQ.I.D.NO:7

6A1 $V_L$ region amino acid sequence (consensus of 10 clones from 2 RT-PCR reactions):

SEQ.I.D.NO:8

3. Chimaeric Antibody

A chimaeric antibody consisting of parent murine V regions (described in section 2.7) was grafted onto human IgG1/k wild type C regions, this was designed to confirm the cloning of the correct murine V regions and also to be used as a reference when testing humanised constructs. The chimaeric antibody was expressed in CHO cells, purified and tested for binding to human IL-13 by ELISA.

3.1 PCR Amplification

The cloned murine V regions were amplified by PCR to introduce restriction sites required for cloning into mammalian expression vectors RId and RIn. Hind III and Spe I sites were designed to frame the $V_H$ domain and allow cloning into a modified RId vector containing the human γ1 wild type C region. Hind III and BsiW I sites were designed to frame the $V_L$ domain and allow cloning into a modified RIn vector containing the human κ C region.

$V_H$ forward primer:

(SEQ. I.D. NO: 86)
5'-GAT GAA GCT TGC CAC CAT GAA ATG CAG CTG GGT CAT C-3'

The Hind III restriction site is underlined and Kozak sequence in bold.

$V_H$ reverse primer:

(SEQ. I.D. NO: 87)
5'-GAT GGA CTA GTG TTC CTT GAC CCC AGT A-3'

The Spe I restriction site is underlined.

$V_L$ forward primer:

(SEQ. I.D. NO: 88)
5'-GAT GAA GCT TGC CAC CAT GAA GTT GCC TGT TAG GCT G-3'

The Hind III restriction site is underlined and Kozak sequence in bold.

$V_L$ reverse primer:

(SEQ. I.D. NO: 89)
5'-GAT GCG TAC GTT TGA TTT CCA GCT TGG TGC C-3'

The BsiW I restriction site is underlined

| PCR reaction: | water | 66 μl |
|---|---|---|
| | 10x PCR buffer | 10 μl |
| | dNTP (2 mM) | 10 μl |
| | primer 1 (5 μM) | 4 μl |
| | primer 2 (5 μM) | 4 μl |
| | AmpliTaq polymerase | 2 μl |
| | purified plasmid | 4 μl |
| | total vol | 100 μl |

Primer 1: $V_H$ or $V_L$ forward primer
Primer 2: $V_H$ or $V_L$ reverse primer
Purified plasmid: pCR2.1 $V_H$ or $V_L$ plasmid purified by Qiagen Minipreps (diluted 200×)

| PCR cycle: | 1-95° C. for 4 min |
|---|---|
| | 2-95° C. for 1 min |
| | 3-55° C. for 1 min |
| | 4-72° C. for 1 min |
| | 5-72° C. for 7 min | steps 2 to 4: were repeated 30 times

3.2 Cloning into Mammalian Expression Vectors

The PCR products were purified using the MinElute PCR Purification kit from Qiagen according to manufacturer's instructions.

The $V_H$ PCR product and RId hCγ1wt mammalian expression vector were digested Hind III-Spe I:

| | |
|---|---|
| 10x buffer (NEBuffer2) | 5 μl |
| BSA 100x (NEB) | 0.5 μl |
| DNA | 5 μl |
| Hind III (Promega) | 2 μl |
| Spe I (NEB) | 2 μl |
| water | 35.5 μl |
| total vol | 50 μl |

DNA: purified $V_H$ PCR product or RId hCγ1 wt vector (at 0.25 mg/ml) Incubated at 2 h at 37° C.

The $V_L$ PCR product and RIn hCκ mammalian expression vector were digested Hind III-BsiW I:

| | |
|---|---|
| 10x buffer (NEBuffer2) | 5 μl |
| DNA | 5 μl |
| Hind III (Promega) | 2 μl |
| water | 38 μl |
| total vol | 50 μl |

DNA: purified $V_L$ PCR product or RIn hCκ vector (at 0.25 mg/ml) Incubated at 2 h at 37° C. 2 μl of BsiW I (NEB) was added and incubated 2 h at 55° C.

The products of restriction digests were loaded in gel loading solution on a preparative 1% agarose gel containing 0.01% ethidium bromide and run in TAE buffer at 100V for 1 hour and the RId and RIn vector as well as $V_H$ and $V_L$ PCR fragment bands were excised. A 100 bp DNA ladder was also run on the gel to allow identification of the $V_H$, $V_L$ and vector bands. The DNA was extracted and purified from the gel using the QIAquick Gel extraction kit from Qiagen according to manufacturer's instructions. The $V_H$ PCR fragment Hind III-Spe I digested was ligated into the RId hCγ1wt vector Hind III-Spe I digested. The $V_L$ PCR fragment Hind III-BsiW I digested was ligated into the RIn hCκ vector Hind III-BsiW I digested. The ligation was carried out using the LigaFast Rapid DNA Ligation System from Promega according to manufacturer's instructions providing:

| | |
|---|---|
| $V_H$: | vector: RId hCγ1wt Hind III-Spe I digested |
| | insert: $V_H$ PCR fragment Hind III-Spe I digested |
| $V_L$: | vector: RIn hCκ Hind III-BsiW I digested |
| | insert: $V_L$ PCR fragment Hind III-BsiW I digested |

Ligated products were transformed into DH5α competent cells. 200 μl DH5α vials were thawed on ice. 50 μl aliquots were prepared in transformation tubes. 2 μl of ligation mixture was added and mixed gently with a pipette tip followed by incubation for 30 min on ice. The mixture was incubated for 45 sec at 42° C. without shaking. This was then transferred to ice for 2 min. 450 μl SOC medium was added and the tubes incubated for 1 h at 37° C. on shaker incubator. 100 μg/ml of culture was spread on L-agar plates supplemented with 100 μg/ml ampicillin and incubated overnight at 37° C.

3.3 Sequencing $V_H$ and $V_L$ clones were cultured overnight at 37° C. in 5ml LB medium supplemented with 100 μg/ml ampicillin. RId and RIn plasmids containing $V_H$ and $V_L$ domains respectively were extracted and purified using the QIAprep Spin Miniprep kit from Qiagen according to manufacturer's instructions. The $V_H$ region was sequenced using forward primers in the RId vector and signal sequence and reverse primer in the human Cγ1 region.

The $V_L$ region was sequenced using forward primers in the RIn vector and signal sequence and reverse primer in the human Cκ region. Clones with the correct $V_H$ and $V_L$ sequences were identified and plasmids prepared for expression in CHO cells.

3.4 Chimaeric Antibody Expression in CHO Cells

RId and RIn plasmids containing 6A1 $V_H$ and $V_L$ domains respectively were transiently co-transfected into CHO cells and expressed. The chimaeric antibody produced was purified from cell culture supernatant by affinity chromatography on Protein A Sepharose.

3.4.1 Plasmid Purification

DH5α cells containing RId-6A1$V_H$ and RIn-6A1$V_L$ plasmids were cultured in 5 ml of LB media supplemented with 100 μg/ml ampicillin for 8 h at 37° C. in a shaker incubator. 200 ml of LB media supplemented with 100 μg/ml ampicillin was inoculated with 1 ml of day culture and incubated overnight at 37° C. in a shaker incubator. The plasmids were extracted and purified using the QIAfilter Plasmid Maxi kit from Qiagen according to manufacturer's instructions. The ethanol pellet was resuspended in 200 μl TE buffer and plasmid concentration was measured by absorbance at 260 nm after 100-fold dilution of stock solution.

3.4.2 Transfection

CHO cells were cultured to confluence in Dulbecco's MEM with Glutamax-1 (DMEM) media supplemented with Ultra Low Fetal Bovine Serum and 1% Penicillin-Streptomycin in 4×175 $cm^2$ BD Falcon tissue culture flasks at 37° C.

For each flask, in a 50 ml Falcon tube, the following were added and mixed:
  8 ml Optimem 1 with Glutamax-1
  20 μg RId-6A1$V_H$ purified plasmid
  20 μg RIn-6A1$V_L$ purified plasmid
  240 μl TransFast Transfection Reagent under vortex The mixture was incubated for 10-15min at RT. DMEM media was removed from flask then the mixture was vortexed and added to flask. The mixture was incubated at 37° C. for 1 h. 32 ml Optimem was added to the flask and incubated at 37° C. for 48-72 h.

3.4.3 Purification of Chimaeric Antibody

Media from all 175 $cm^2$ flasks were pooled and centrifuged at 1500 rpm for 3 min on an MSE Mistral 2000 and supernatant passed through a 500 mL Filter System 0.22μm CA. The antibody was purified from clarified supernatant on an Amersham Biosciences Akta Explorer using Unicorn software. The column used was a 1 ml HiTrap rprotein A Sepharose FF.

The flow rate was 1 ml/min.

The column was equilibrated with 10CV of Dulbecco's PBS then loaded with clarified supernatant through pump A. The column was washed with 20CV of Dulbecco's PBS, pump A was washed to waste and a further 10CV of Dulbecco's PBS was passed through the column to ensure complete clearance of supernatant.

The antibody was eluted with 10CV of ImmunoPure IgG Elution Buffer (Pierce) and collected in 1 ml fractions containing 100 μl of 1M Trizma-HCl pH8.0 neutralisation buffer. The column was re-equilibrated with 5CV of Dulbecco's PBS.

Antibody in eluate fractions was quantified by reading the absorbance at 280 nm against a blank solution containing 10 volumes of ImmunoPure IgG Elution Buffer +1 volume of 1M Trizma-HCl pH8.0 and fractions with sufficient amounts of pure antibody were pooled and stored in 100 µl aliquots at −20° C.

3.4.4 Analysis of Chimaeric Antibody

Figure 8:
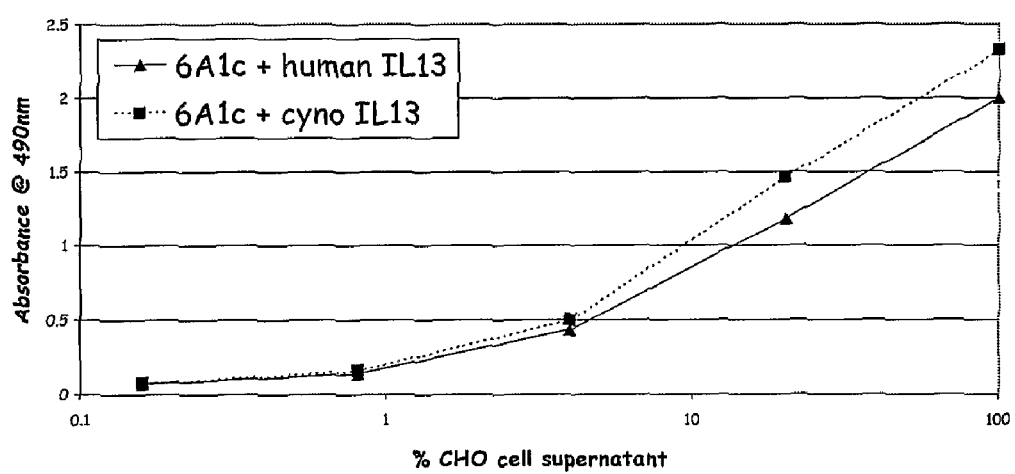
FIG. 8
Sandwich ELISA illustrating the binding of chimaeric 6A1 mAb to recombinant *E.coli*-expressed human IL-13 and cynomolgus IL-13 at increasing concentrations.

Supernatant and purified 6A1 chimaeric antibody (6A1c) were analysed in human and cynomolgus IL-13 binding ELISAs. Supernatant from CHO cells transiently transfected with chimaeric 6A1 monoclonal antibody, bound both *E.coli*-expressed recombinant human and cynomolgus IL-13 in a sandwich ELISA. Purified antibody also bound both *E.coli*-expressed recombinant human and cynomolgus IL-13 in the sandwich ELISA (data not shown). See FIG. 8.

The amino acid sequence and a cDNA sequence for cynomolgus IL-13 (including signal sequence) is set forth as SEQ.I.D.NO:90 and 91 respectively.

These results confirm that the correct 6A1 variable regions have been cloned successfully to produce an antigen binding chimaeric antibody capable of binding both human and cynomologus IL-13.

4. Humanisation of Clone 6A1

4.1 Humanisation Strategy

4.1.1 Search of the Mouse Database 12 mouse sequences with the highest homology for the 6A1 $V_H$ amino acid sequence and 11 mouse sequences with the highest homology for the $V_L$ amino acid sequence were identified by searching a peptide database (Genbank)

The 6A1 $V_H$ amino acid sequence was compared to all 12 mouse sequences from the database search and the following framework residues were identified as significant:

| Position | 6A1 VH | mouse | occurrence |
|---|---|---|---|
| 19 | R | K | 12/12 |
| 38 | I | K | 12/12 |
| 81 | R | Q | 12/12 |

Position is according to the Kabat et al numbering system. The 6A1 $V_L$ amino acid sequence was compared to 11 mouse sequences from the database search no framework residues were identified as significant.

4.1.2. Search of the Human Database

Human framework sequences with the highest homology to 6A1 $V_H$ and $V_L$ frameworks were identified using the Easy-Blast in a peptide database.

One set of human sequences were identified for 6A1 $V_H$ of which the following framework was selected for humanisation:

SEQ.I.D.NO:92

The following framework residues were identified as potentially important in recovering affinity and may need to be backmutated:

| Position (Kabat#) | Human $V_H$ | 6A1 $V_H$ |
|---|---|---|
| 19 | K | R |
| 38 | R | I |
| 73 | E | T |
| 81 | E | R |

4 humanised VH constructs with different backmutations were designed, one as a straight graft according to the definitions of CDR given above (A1), the others with various backmutations (A2, A3, A4).

Therefore
A2 is A1 plus R381
A3 is A2 plus E73T
A4 is A3 plus K19R plus E81R

One set of human sequences was identified for 6A1 $V_L$ of which the following framework was selected for humanisation:

SEQ.I.D.NO:93

The following residues were identified as potentially important in recovering affinity and may need to be backmutated:

| Position (Kabat#) | mouse 6A1 $V_L$ | Human $V_L$ |
|---|---|---|
| 85 | V | I |

Two constructs were designed, one as a straight graft (L1), the other with the backmutation (L2) (i.e. L1 with 185V).

Humanised $V_H$ construct A1:

SEQ.I.D.NO:11

Humanised $V_H$ construct A2:

SEQ.I.D.NO:12

Humanised $V_H$ construct A3:

SEQ.I.D.NO:13

Humanised $V_H$ construct A4:

SEQ.I.D.NO:14

Humanised $V_L$ construct L1:

SEQ.I.D.NO:15

Humanised $V_L$ construct L2:

SEQ.I.D.NO:16

4.2 Humanisation of 6A1

Humanised $V_H$ and $V_L$ constructs were prepared de novo by build up of ovserlapping oligonucleotides including restriction sites for cloning into RId and RIn mammalian expression vectors as well as a human signal sequence. Hind III and Spe I restriction sites were introduced to frame the $V_H$ domain containing the human signal sequence for cloning into RId containing the human γ1 wild type constant region. Hind III and BsiW I restriction sites were introduced to frame the $V_L$ domain containing the human signal sequence for cloning into RIn containing the human kappa constant region.

Human signal sequence: SEQ.I.D.NO:17

4 humanised $V_H$ constructs and two humanised VL constructs were designed. This would result in 8 different heavy chain-light chain combinations.

Approximately 10 oligonucleotides of approximately 60 bases long with approximately 18 base overlap were designed for build up.

4.2.1 Oligonucleotide Build-Up

Oligonucleotide pool solutions were prepared from 5 µl of each oligo stock solution at 100 µM. Synthesis of the humanised $V_H$ and $V_L$ genes by build up of overlapping oligonucleotides was carried out generally according to Stemmer WP et al (1995) Gene 164(1):49-53 using software described in Ertl PF et al (2003) Methods 31:199-206.

| 4.2.1.1 Representative assembly PCR reaction: | water | 41.5 μl |
|---|---|---|
| | 10 × ProofStart PCR buffer | 5 μl |
| | dNTP (10 mM) | 1.5 μl |
| | oligo pool | 1 μl |
| | ProofStart DNA Polymerase | 1 μl |
| | total vol | 50 μl |
| Assembly PCR cycle: | 1-94° C. for 2 min | |
| | 2-94° C. for 30 sec | |
| | 3-40° C. for 2 min | |
| | 4-72° C. for 10 sec | |
| | 5-94° C. for 15 sec | |
| | 6-40° C. for 30 sec | |
| | 7-72° C. for 20 sec + 3 sec/cycle | |
| | steps 4 to 7 were repeated 25 times | |

4.2.1.2 Representative Recovery PCR

Primers 1 and 2 were the first upper and lower oligonucleotides used in the assembly PCR. The recovery PCR allows the amplification of the complete V gene.

| Recovery PCR reaction: | water | 42 μl |
|---|---|---|
| | 10 × ProofStart PCR buffer | 4 μl |
| | dNTP (10 mM) | 1.5 μl |
| | primer 1 (100 μM) | 0.5 μl |
| | primer 2 (100 μM) | 0.5 μl |
| | assembly PCR reaction | 1 μl |
| | ProofStart DNA Polymerase | 0.5 μl |
| | total vol | 50 μl |
| Recovery PCR cycle: | 1-94° C. for 2 min | |
| | 2-94° C. for 45 sec | |
| | 3-60° C. for 30 sec | |
| | 4-72° C. for 2 min | |
| | 5-72° C. for 4 min | |
| | steps 2 to 4 were repeated 25 times | |

The recovery PCR products were purified using the MinElute PCR Purification kit from Qiagen according to manufacturer's instructions.

4.2.2 Restriction Digests

Humanised 6A1 $V_H$ constructs A1, A2, A3, A4 were digested with Hind III-Spe I, humanised 6A1 $V_L$ constructs L1, L2 were digested with Hind-III-BsiW I as described similarly to section 3.

4.2.3 Gel Purification

The products of restriction digest were purified similarly to section 3.

4.2.4 Ligation

The 6A1 humanised VH fragments Hind III-Spe I digested were ligated into the RId hCγ1wt vector Hind III-Spe I digested.

The 6A1 humanised $V_L$ fragments Hind III-BsiW I digested were ligated into the RIn hCκ vector Hind III-BsiW I digested. The ligation was carried out using the LigaFast Rapid DNA Ligation System from Promega according to manufacturer's instructions.

4.2.5 Transformation

Similarly as described previously in section 3

4.2.6 Representative Sequencing Method

Colonies from each reaction plate were cultured overnight at 37° C. in 5 ml LB medium supplemented with 100 μg/ml ampicillin. Plasmids were extracted and purified using the QIAprep Spin Miniprep kit from Qiagen according to manufacturer's instructions and sequenced using primers described previously in section 3. Clones with the correct humanised VH and $V_L$ sequences were identified and plasmids prepared for expression in CHO cells.

5. Expression and Characterisation of Humanised Antibodies

Four humanised VH constructs (A1, A2, A3, A4) and two humanised $V_L$ constructs (L1 and L2) were prepared in RId hCγ1wt and RIn hCκ mammalian expression vectors. Eight plasmid heavy chain-light chain combinations (A1L1, A1L2, A2L1, A2L2, A3L1, A3L2, A4L1, A4L2) were transiently co-transfected into CHO cells and expressed at small scale to give 8 different humanised antibodies. The antibodies produced in the CHO cell supernatant were analysed in the human IL-13 binding ELISA.

5.1 Representative Plasmid Purification Method

DH5α cells containing one of the plasmids described above were cultured in 5 ml of LB media supplemented with 100 μg/ml ampicillin for 8 h at 37° C. in a shaker incubator. 200ml of LB media supplemented with 100 μg/ml ampicillin was inoculated with 1 ml of day culture and incubated overnight at 37° C. in a shaker incubator. The plasmids were extracted and purified using the QIAfilter Plasmid Maxi kit from Qiagen according to manufacturer's instructions. The ethanol pellet was resuspended in 200 μl TE buffer and plasmid concentration was measured by absorbance at 260 nm after 100 fold dilution of stock solution.

5.2 Representative Transfection Method 9 wells of Corning Costar 3506 6-well plates were seeded with $10^6$ CHO cells and cultured overnight in Dulbecco's MEM with Glutamax-1 (DMEM) media supplemented with Ultra Low Fetal Bovine Serum and 1% Penicillin-Streptomycin at 37° C.

For each well, the following were added in a 5 ml Bijou so that each transfection contained a different combination of light and heavy chains.

1 ml Optimem 1 with Glutamax-1
5 μg plasmid carrying humanised $V_H$
5 μg plasmid carrying humanised $V_L$
30 μg TransFast Transfection Reagent under vortex Incubation took place for 10-15 min at room temperature. DMEM media was removed from wells then vortex mixture and added to the appropriate well. Incubation took place at 37° C. for 1 h. 2 ml Optimem was added per well and incubated at 37° C. for 48-72 h.

5.3 Analysis of Humanised Antibodies

Figure 9:
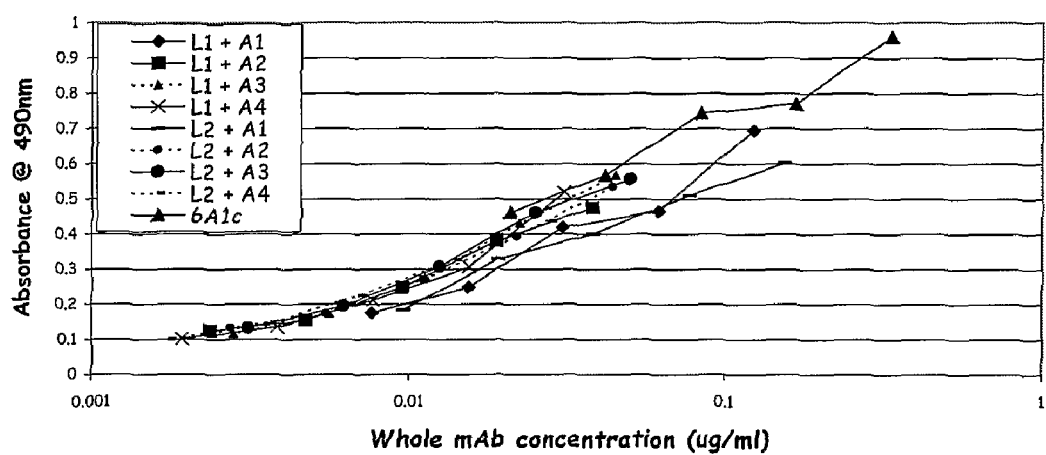
FIG. 9
Sandwich ELISA illustrating the binding of 8 humanised anti-human IL-13 mAbs to recombinant *E.coli*-expressed human IL-13 at increasing concentrations.

Media from each well was recovered and centrifuged at 13000 rpm for 1 min on an Eppendorf 5415R bench centrifuge and supernatant passed through a 0.2 μm Pall Acrodisc 25 mm syringe filter. Cell supernatant was assessed for binding to human IL-13 in an ELISA. All 8 humanised antibodies bound human IL-13 with a similar profile to the 6A1 chimaeric antibody in a human IL-13 binding ELISA. See FIG. 9.

Humanised antibodies L1+A1 and L2+A1 were selected for expression scale-up, purification and further analysis.

6. Assessment of Humanised Anti-Human IL-13 Antibodies L1+A1 and L2+A1

6.1 Activity in Human and Cynomolqus IL-13 Binding ELISAs

Figure 10A:
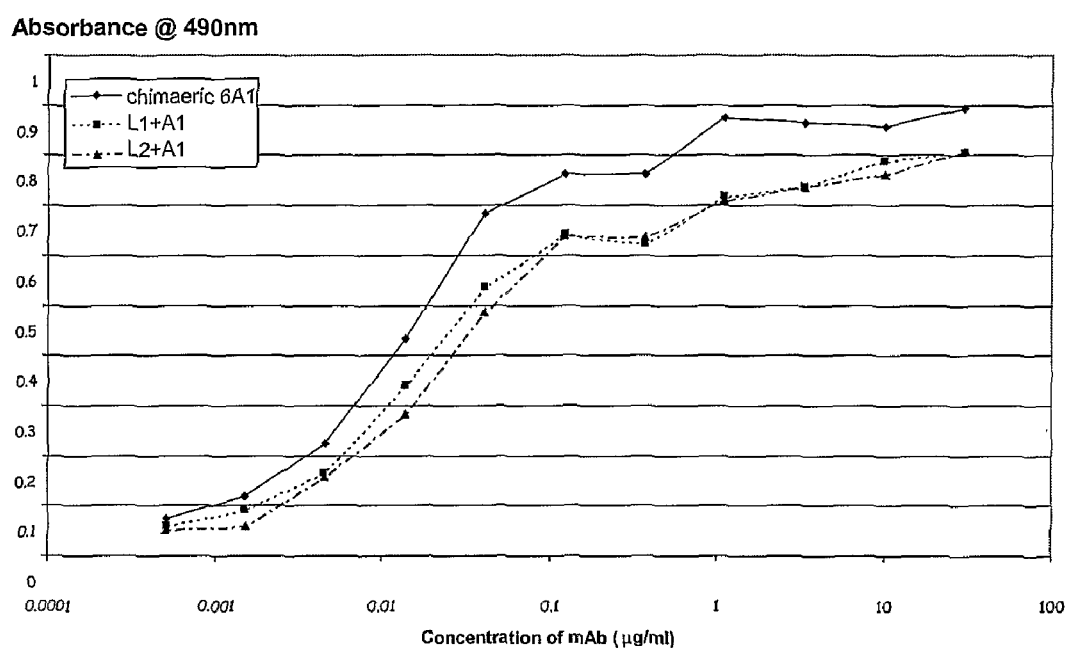
FIG. 10a
Sandwich ELISA illustrating the binding of chimaeric 6A1, L1+A1 and L2+A1 to recombinant *E.coli*-expressed human IL-13 at increasing concentrations.
Figure 10B:
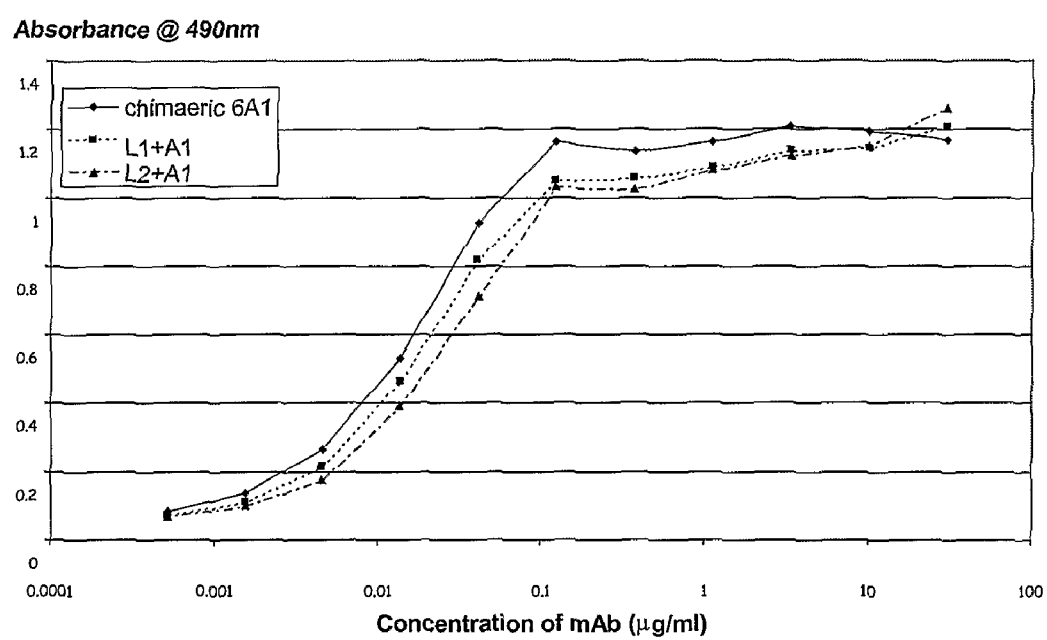
FIG. 10b
Sandwich ELISA illustrating the binding of chimaeric 6A1, L1+A1 and L2+A1 to recombinant *E.coli*-expressed cynomolgus IL-13 at increasing concentrations.

L1+A1 and L2+A1 were successfully generated from scale-up and assessed for binding to E.coli-expressed human and cynomolgus IL-13 by ELISA. See FIGS. 10a and 10b and Table B.

TABLE B

| ELISA | mAb | EC$_{50}$ (µg/ml) |
|---|---|---|
| Human IL-13 binding | 6A1 parental mAb | 0.049 |
| | chimaeric 6A1 | 0.015 |
| | L1 + A1 | 0.018 |
| | L2 + A1 | 0.024 |
| Cynomolgus IL-13 binding | 6A1 parental mAb | 0.039 |
| | chimaeric 6A1 | 0.018 |
| | L1 + A1 | 0.021 |
| | L2 + A1 | 0.028 |

Both L1+A1 and L2+A1 bound *E.coli*-expressed human and cynomolgus IL-13 with a similar profile. EC$_{50}$ values (generated using an Excel 'Robosage' curve fitting function) indicated binding activity is very similar to the chimaeric 6A1 mAb standard.

6.2 Assessment of L1+A1 and L2+A1 for Binding to Native (PBMC Derived) Human IL-13

Figure 11:
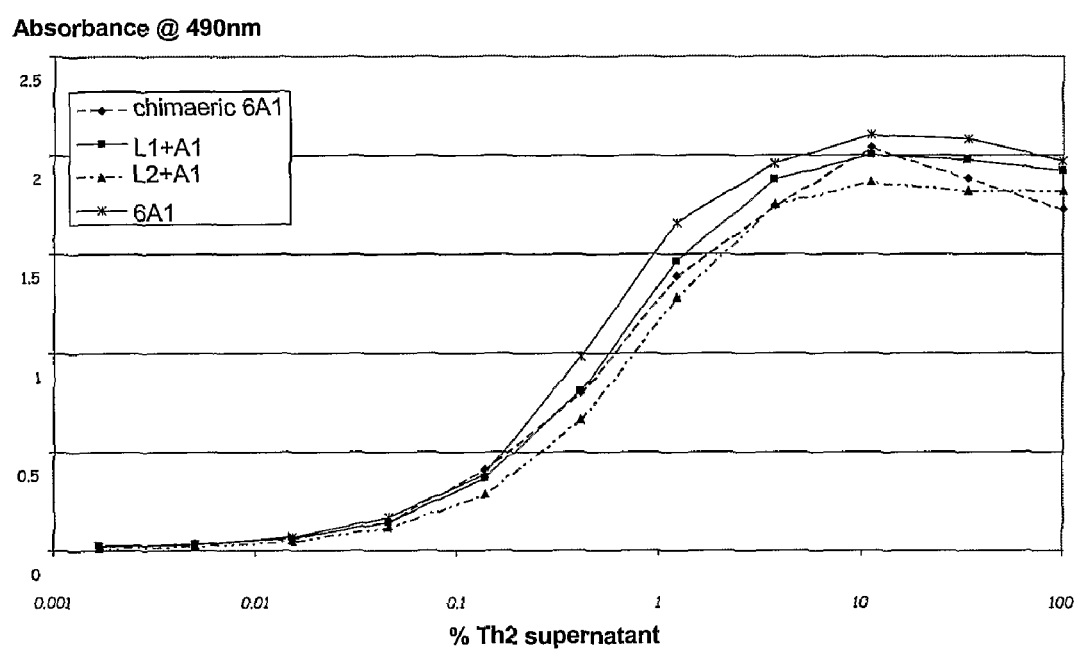
FIG. 11
Sandwich ELISA illustrating the binding of chimaeric 6A1, L1+A1 and L2+A1 to native human IL-13 at increasing concentrations.

Supernatant from CD4+Th2 cells (generated from human PBMC cultures) stimulated with anti-CD3 and anti-CD28 was used to assess the binding of chimaeric 6A1 mAb, L1+A1 and L2+A1 to native (PBMC derived) human IL-13. In an ELISA, all 3 antibodies bound native human IL-13 in the Th2 cell supernatant with very similar performance to that of the parental 6A1 mAb. See FIG. 11.

In addition, a standard curve was generated using commercially available reagents, to determine the level of native human IL-13 present in the Th2 cell supernatant. All 3 antibodies and a commercially available anti-human IL-13 mAb detected equivalent amounts of IL-13 in the Th2 supernatant sample. See Table 2 below.

TABLE 2

| mAb | Native IL-13 (ng/ml) |
|---|---|
| 6A1 parental mAb | 22.5 |
| chimaeric 6A1 | 19.6 |
| L1 + A1 | 25.1 |
| L2 + A1 | 22.7 |
| + control mAb | 28.0 |

Figure 12A:
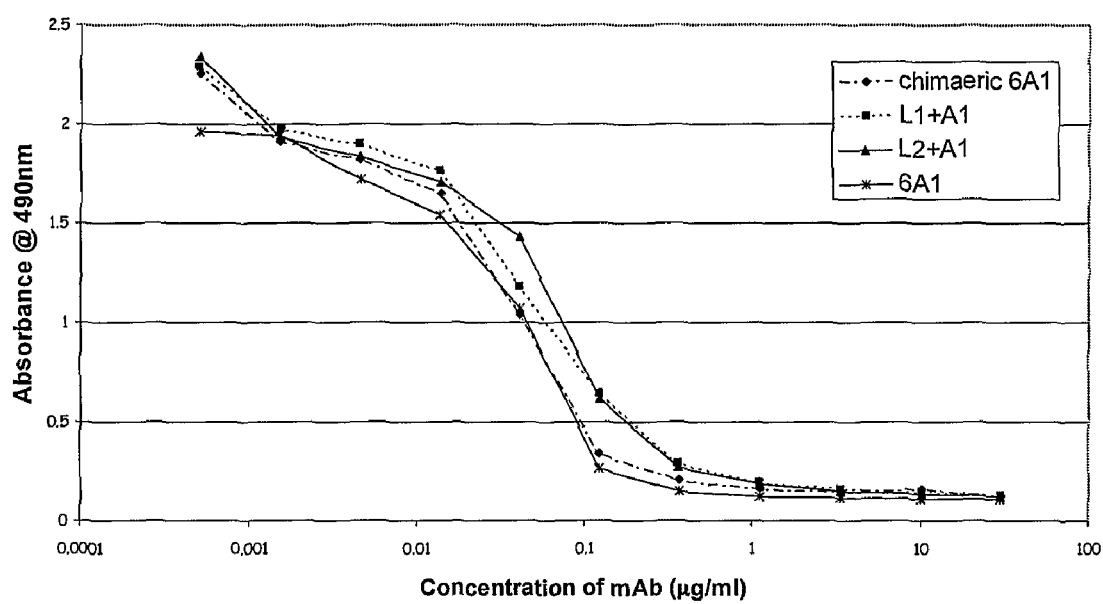
FIG. 12a
ELISA illustrating the ability of monoclonal antibody 6A1, chimaeric 6A1, L1+A1 and L2+A1 at increasing concentrations to inhibit recombinant *E.coli*-expressed human IL-13 binding to the human IL-13 receptor a 1 chain.
Figure 12B:
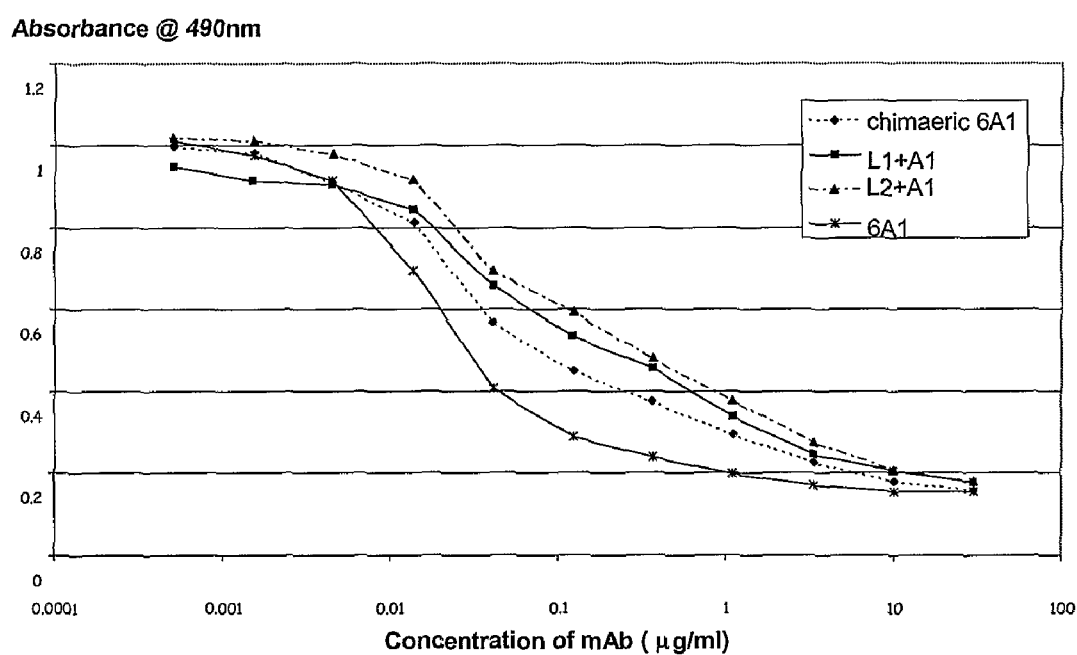
FIG. 12b
ELISA illustrating the ability of monoclonal antibody 6A1, chimaeric 6A1, L1+A1 and L2+A1 at increasing concentrations to inhibit recombinant *E.coli*-expressed human IL-13 binding to the human IL-13 receptor α2 chain.
Figure 13A:
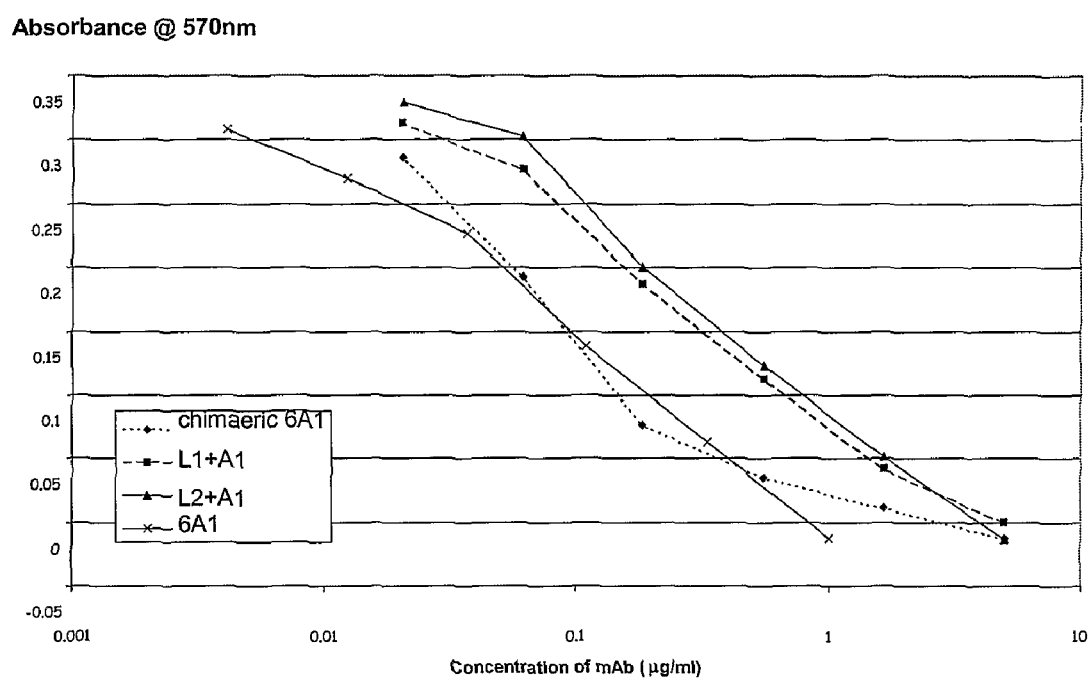
FIG. 13a
Neutralisation assay illustrating the ability of 6A1, chimaeric 6A1, L1+A1 and L2+A1 at increasing concentrations to inhibit the bioactivity of recombinant *E.coli*-expressed human IL-13 in a TF-1 cell proliferation assay.
Figure 13B:
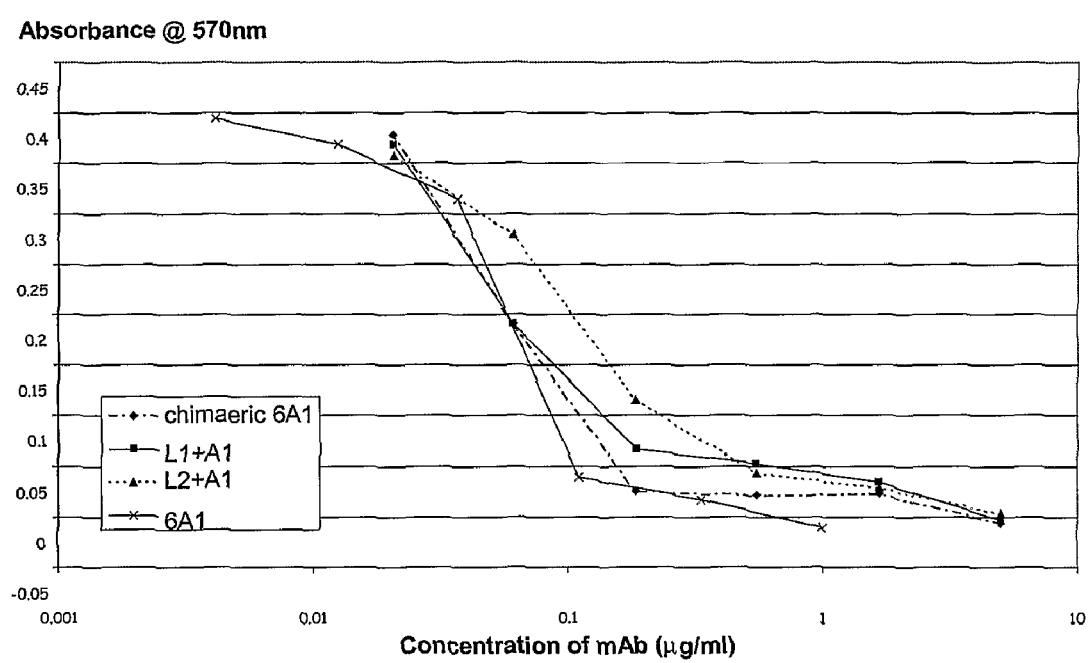
FIG. 13b
Neutralisation assay illustrating the ability of 6A1, chimaeric 6A1, L1+A1 and L2+A1 at increasing concentrations to inhibit the bioactivity of recombinant *E.coli*-expressed cynomolgus IL-13 in a TF-1 cell proliferation assay.
Figure 13C:
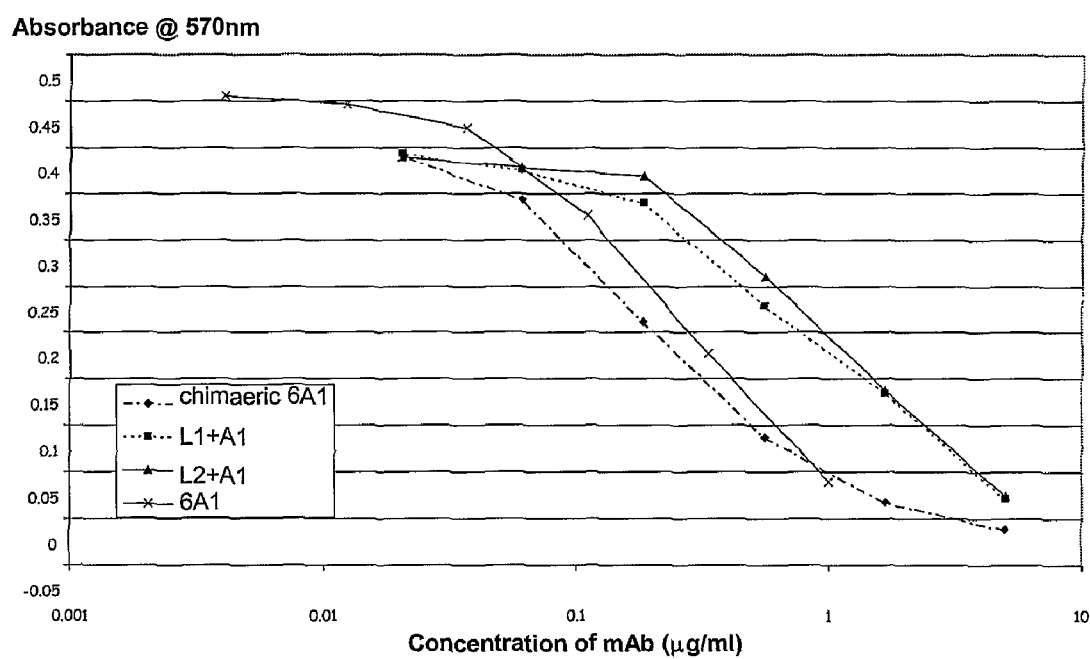
FIG. 13c
Neutralisation assay illustrating the ability of 6A1, chimaeric 6A1, L1+A1 and L2+A1 at increasing concentrations to inhibit the bioactivity of recombinant *E.coli*-expressed Q130 human IL-13 in a TF-1 cell proliferation assay.
Figure 13D:
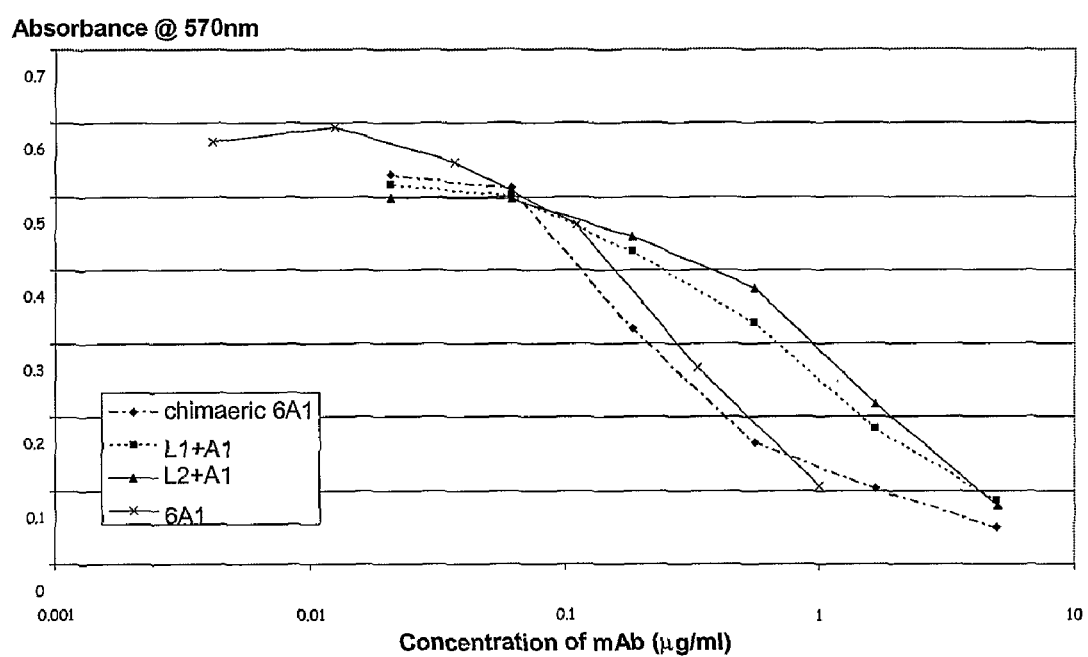
FIG. 13d
Neutralisation assay illustrating the ability of 6A1, chimaeric 6A1, L1+A1 and L2+A1 at increasing concentrations to inhibit the bioactivity of mammalian-expressed (CHO cell) human IL-13 in a TF-1 cell proliferation assay.

6.3 Inhibitory Activity of L1+A1 and L2+A1 for Human IL-13 in IL-13 Receptor Binding ELISAs 6A1 parental mouse mAb, chimaeric 6A1, L1+A1 and L2+A1, were assessed for ability to inhibit binding of human IL-13 to IL-13Rα1 and IL-13Rα2 chains in a competition ELISA. See FIGS. 12*a* and 12*b* and Table 3 below.

TABLE 3

| ELISA | mAb | IC$_{50}$ (µg/ml) |
|---|---|---|
| Human IL-13Rα1 competition | 6A1 parental mAb | 0.039 |
| | chimaeric 6A1 | 0.034 |
| | L1 + A1 | 0.044 |
| | L2 + A1 | 0.056 |
| Human IL-13Rα2 competition | 6A1 parental mAb | 0.020 |
| | chimaeric 6A1 | 0.040 |
| | L1 + A1 | 0.113 |
| | L2 + A1 | 0.117 |

All antibodies inhibited the binding of *E.coli*-expressed det-1 tagged human IL-13 to human IL-13Rα1 with a similar profile. Similarly, all antibodies inhibited the binding of *E.coli*-expressed det-1 tagged human IL-13 to human IL-13Rα2, though with some reduction in potency for L1+A1 and L2+A1 in this assay (IC$_{50}$ values were generated using the Excel 'Robosage' curve fitting function).

6.4 Affinity Assessment of L1+A1 and L2+A1 for Binding to Human IL-13

The binding kinetics of L1+A1 and L2+A1 for human IL-13 were assessed using the BIAcore™ system. See Section 7 below for methods used.

Analysis 1:

Completed for both human and cynomolgus IL-13 (*E.coli*-expressed protein). The quoted KD values are the average from 5 different IL-13 concentration curves (done in triplicate). Note that mass transfer issues were apparent in this analysis and that a modified experimental protocol (to correct for this issue) has been completed in analysis 4 (where no mass transfer issues were present). See Table 4.

TABLE 4

| IL-13 sample | mAb | On rate ka (Ms$^{-1}$) | Off rate kd (s$^{-1}$) | Affinity constant KD (pM) |
|---|---|---|---|---|
| Human IL-13 | 6A1 parental mAb | 1.96 × 10$^6$ | 6.78 × 10$^{-5}$ | 35 |
| | chimaeric 6A1 | 4.64 × 10$^5$ | 2 × 10$^{-5}$ | 43 |
| | L1 + A1 | 5.07 × 10$^5$ | 1.55 × 10$^{-4}$ | 300 |
| | L2 + A1 | 5.07 × 10$^5$ | 1.56 × 10$^{-4}$ | 310 |
| Cynomolgus IL-13 | 6A1 parental mAb | 9.14 × 10$^5$ | 5.6 × 10$^{-5}$ | 61 |
| | chimaeric 6A1 | 5.92 × 10$^5$ | 3.27 × 10$^{-5}$ | 55 |
| | L1 + A1 | 4.46 × 10$^5$ | 1.55 × 10$^{-5}$ | 35 |
| | L2 + A1 | 5.77 × 10$^5$ | 5.58 × 10$^{-5}$ | 97 |

Analysis 2:

Completed for human IL-13 (*E.coli*-expressed protein) binding to L1+A1. See Table 5.

TABLE 5

| IL-13 sample | mAb | On rate ka (Ms–1) | Off rate kd (s–1) | Affinity constant KD (pM) |
|---|---|---|---|---|
| Human IL-13 | L1 + A1 | 4.66 × 105 | 6.95 × 10$^{-5}$ | 149 |

Analysis 3:

Completed for the 16 mer biotinylated human IL-13 peptide number 24 (identified as the linear binding epitope for parental mAb 6A1, see section 6.7). Note that the absolute KD values obtained for binding to peptide ligands are often quite different to those seen for binding to whole protein targets. However, it is believed that this data is consistent with the whole protein data and the IL-13 neutralisation data (in the TF-1 bioassay) in that they indicate a reduction in affinity of about 3-fold between the chimaeric 6A1 and L1+A1. See Table 6.

TABLE 6

| IL-13 sample | mAb | On rate ka (Ms$^{-1}$) | Off rate kd (s$^{-1}$) | Affinity constant KD (nM) |
|---|---|---|---|---|
| Peptide 24 | 6A1 parental mAb | 2.95 × 10$^5$ | 9.15 × 10$^{-4}$ | 3.11 |
| | chimaeric 6A1 | 2.57 × 10$^5$ | 9.19 × 10$^{-4}$ | 3.58 |
| | L1 + A1 | 1.95 × 10$^5$ | 1.7 × 10$^{-3}$ | 9.03 |
| | L2 + A1 | 1.79 × 10$^5$ | 1.67 × 10$^{-3}$ | 9.35 |

Analysis 4:

Completed for both human and cynomolgus IL-13 (*E.coli*-expressed protein). The quoted KD values are the average from 5 different IL-13 concentration curves (done in triplicate). Note that no mass transfer issues were apparent for this data set. See Table 7.

TABLE 7

| IL-13 sample | mAb | On rate $k_a$ (Ms$^{-1}$) | Off rate $k_d$ (s$^{-1}$) | Affinity constant KD (pM) |
| --- | --- | --- | --- | --- |
| Human IL-13 | chimaeric 6A1 | $1.05 \times 10^6$ | $4 \times 10^{-5}$ | 38 |
|  | L1 + A1 | $8.24 \times 10^5$ | $1.4 \times 10^{-4}$ | 170 |
|  | L2 + A1 | $9.07 \times 10^5$ | $1.39 \times 10^{-4}$ | 153 |
| Cynomolgus IL-13 | chimaeric 6A1 | $8.85 \times 10^5$ | $2.65 \times 10^{-5}$ | 30 |
|  | L1 + A1 | $7.3 \times 10^5$ | $5.86 \times 10^{-5}$ | 80 |
|  | L2 + A1 | $7.72 \times 10^5$ | $4.25 \times 10^{-5}$ | 55 |

The results indicate no significant difference between the humanised constructs L1+A1 and L2+A1.

L1+A1 shows an affinity for human IL-13 of approximately 168 pM. The kinetics are dominated by a exceptionally slow off-rate, as would be predicted from the significant neutralising activity of the antibody. Data for the association constant $k_{on}$ are consistently around $6 \times 10^5$ M$^{-1}$s$^{-1}$. Estimates of the dissociation constant $k_{off}$ are more variable, covering the range $1.4 \times 10^{-4}$ to $8.22 \times 10^{-5}$ s$^{-1}$, reflecting the technical challenge of obtaining precise quantification for slow off-rates.

6.5 Activity of L1+A1 and L2+A1 in IL-13 Neutralisation Bioassays

6A1 parental mouse mAb, chimaeric 6A1, L1+A1 and L2+A1 were assessed for IL-13 neutralisation activity in an in vitro TF-1 cell bioassay (this bioassay is the industry standard for assessment of IL-13 bioactivity and for assessment of the neutralization capacity of commercially supplied anti-IL-13 antibodies). A number of IL-13 variants were assessed in this assay, including *E.coli*-expressed human IL-13, *E.coli*-expressed cynomolgus IL-13, *Ecoli*-expressed Q130 human IL-13 (the asthma-associated variant), and mammalian CHO cell-expressed human IL-13 (note: native human IL-13 in the Th2 cell supernatant sample could not be used in this bioassay, as this supernatant also contains other cytokines that are able to proliferate TF-1 cells). See FIGS. 13a, 13b, 13c and 13d.

All antibodies tested neutralised the bioactivity of all IL-13 variants in this bioassay system; the neutralisation capacity of each antibody for each IL-13 variant was determined and expressed as an ND$_{50}$ value. See Table 8

TABLE 8

| IL-13 variant | mAb | Mean ND$_{50}$ for 2 assays (µg/ml) |
| --- | --- | --- |
| *E. coli*-expressed human IL-13 | chimaeric 6A1 | 0.119 |
|  | L1 + A1 | 0.428 |
|  | L2 + A1 | 0.608 |
|  | 6A1 parental mAb | 0.193 |
| *E. coli*-expressed cynomolgus IL-13 | chimaeric 6A1 | 0.059 |
|  | L1 + A1 | 0.078 |
|  | L2 + A1 | 0.120 |
|  | 6A1 parental mAb | 0.078 |
| *E. coli*-expressed Q130 human IL-13 | chimaeric 6A1 | 0.128 |
|  | L1 + A1 | 0.438 |
|  | L2 + A1 | 0.705 |
|  | 6A1 parental mAb | 0.213 |
| CHO-expressed human IL-13 | chimaeric 6A1 | 0.285 |
|  | L1 + A1 | 0.975 |
|  | L2 + A1 | 1.200 |
|  | 6A1 parental mAb | 0.440 |

Note:
as different amounts of each IL-13 variant are required to proliferate the TF-1 cells to the same extent in this bioassay, it may not be desirable to compare the ND$_{50}$ values generated by one particular antibody across each IL-13 variant used. However, it is appropriate to compare the ND$_{50}$ values generated by each antibody for a single IL-13 variant.

In general, the level of neutralisation achieved by the parental 6A1 mAb and chimaeric 6A1 was similar, indicating no detectable loss of potency between the parental mAb and the chimaera. However, the potencies of L1+A1 and L2+A1 were measurably reduced in comparison with both parental 6A1 mAb and chimaeric 6A1 by an average of approximately 3 to 4 fold for each individual IL-13 variant tested. These data are in close agreement with those obtained from the BIAcore™ assessment.

6.6 Specificity of L1 +A1 and L2+A1 for Binding to Human IL-13

Figure 14A:
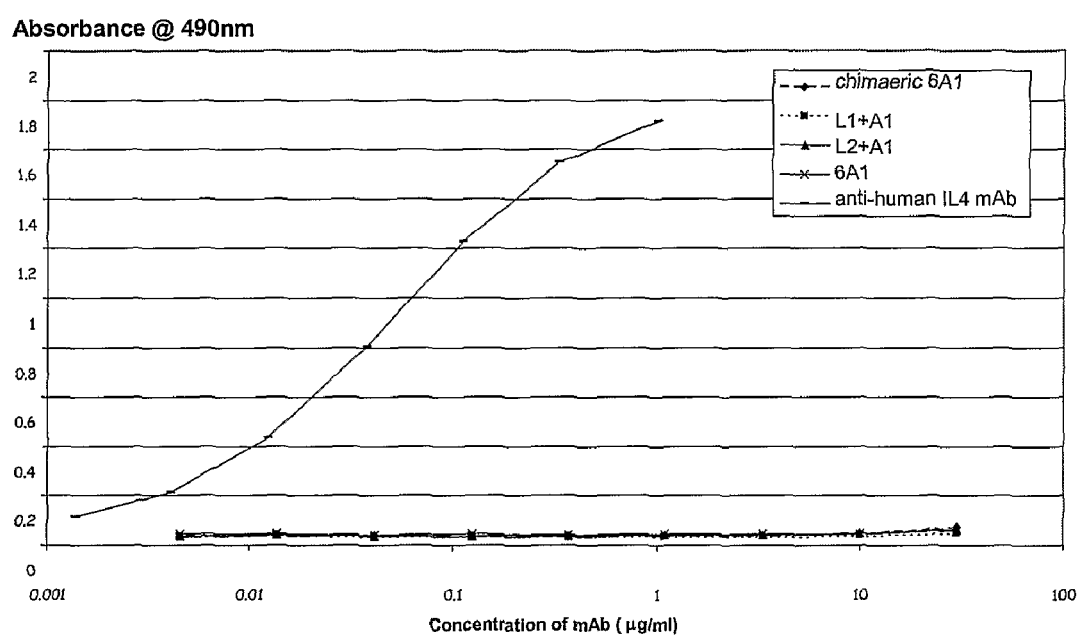
FIG. 14a
Sandwich ELISA demonstrating that 6A1, chimaeric 6A1, L1+A1 and L2+A1 do not bind recombinant *E.coli*-expressed human IL-4.
Figure 14B:
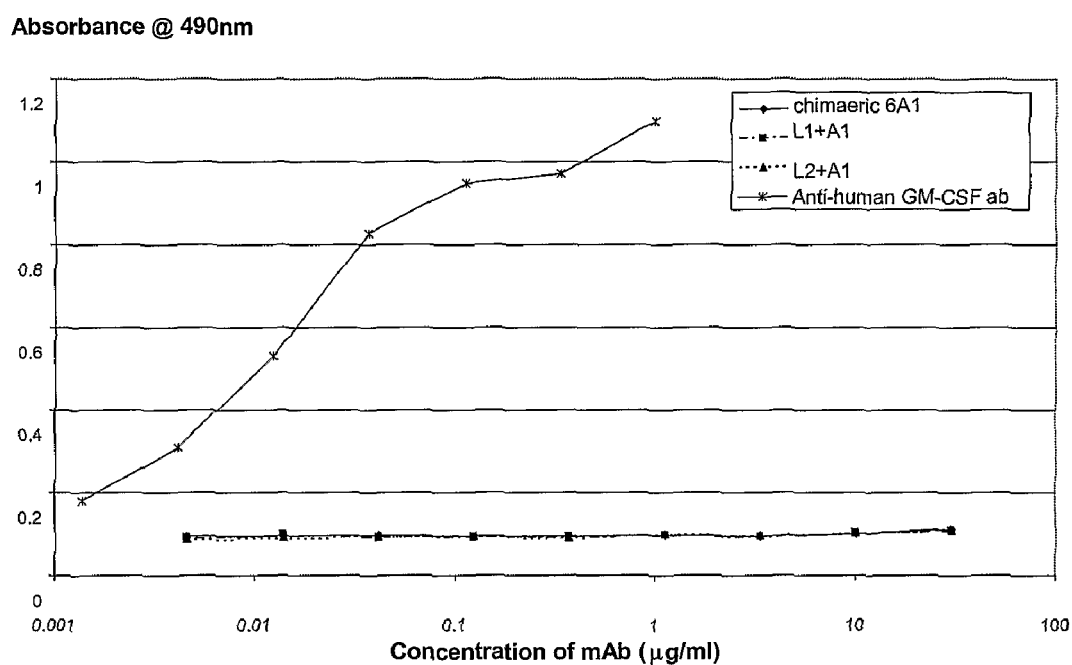
FIG. 14b
Sandwich ELISA demonstrating that 6A1, chimaeric 6A1, L1+A1 and L2+A1 do not bind recombinant *E.coli*-expressed human GM-CSF.

The specificities of L1+A1 and L2+A1 for human IL-13 were assessed by analysis of the cross-reactivity potential against human IL-4 and human GM-CSF in binding ELISAs. See FIGS. 14a and 14b.

Figure 14C:
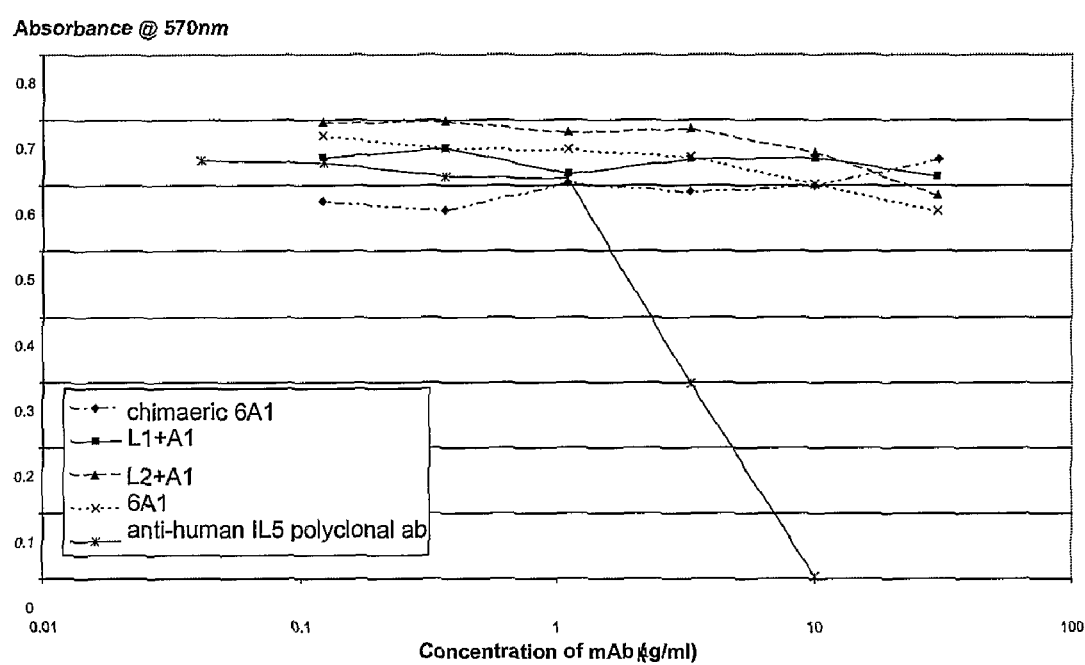
FIG. 14c
An IL5 neutralisation assay, demonstrating that 6A1, chimaeric 6A1, L1+A1 and L2+A1 do not inhibit the bioactivity of recombinant *E.coli*-expressed human IL-5 in a TF-I cell proliferation assay.

These mAbs were found to be specific for binding to IL-13, with no cross-reactivity for human IL-4 or human GM-CSF at mAb concentrations up to 30 µg/ml. In addition, these mAbs did not cross-neutralise the bioactivity of human IL5 in an IL5 bioassay. See FIG. 14c.

6.7 Epitope Mapping of 6A1 using Biotinylated Peptides

Human IL-13 and cynomolgus IL-13 proteins were run on a denaturing SDS-PAGE gel. Western blotting with mouse mAb 6A1 detected bands of the expected size for both human (*E.coli* expressed, in house) and cynomolgus (*E.coli* expressed, in house) IL-13 proteins. 6A1 did not detect hIL-13 (*E.coli* expressed, Cambridge Bioscience), due to a probable technical failure. This analysis suggested that mAb 6A1 recognised a linear peptide epitope within the human and cynomolgus IL-13 sequences (data not shown).

Biotinylated 16 mer peptides offset by 4 were synthesised to map the location of the B cell epitope recognised by mAb 6A1 on both human and cynomolgus IL-13. An ELISA method was used to detect binding of immobilised biotinylated peptide to the parental mAb 6A1.

Details of 16 mer custom designed Peptides: 88×16 mers, offset by 4 (supplied by Mimotopes, Australia).

Format: Peptides 25 & 44 = Biotin-SGSG-PEPTIDE-acid
Peptides 2-24 & 27-43 = Biotin-SGSG-PEPTIDE-amide

| # | Hydro | MolWt | N-term | Sequence | C-term |
| --- | --- | --- | --- | --- | --- |
| 2 | 0.42 | 2,311.66 | Biotin- | SEQ.I.D.NO: 38 | —NH2 |
| 3 | 0.27 | 2,453.82 | Biotin- | SEQ.I.D.NO: 39 | —NH2 |
| 4 | 0.38 | 2,326.70 | Biotin- | SEQ.I.D.NO: 40 | —NH2 |
| 5 | 0.31 | 2,231.58 | Biotin- | SEQ.I.D.NO: 41 | —NH2 |
| 6 | 0.43 | 2,289.66 | Biotin- | SEQ.I.D.NO: 42 | —NH2 |
| 7 | 0.59 | 2,190.57 | Biotin- | SEQ.I.D.NO: 43 | —NH2 |
| 8 | 0.57 | 2,260.64 | Biotin- | SEQ.I.D.NO: 44 | —NH2 |
| 9 | 0.62* | 2,255.64 | Biotin- | SEQ.I.D.NO: 45 | —NH2 |
| 10 | 0.51 | 2,197.56 | Biotin- | SEQ.I.D.NO: 46 | —NH2 |
| 11 | 0.56 | 2,144.52 | Biotin- | SEQ.I.D.NO: 47 | —NH2 |

-continued

Format: Peptides 25 & 44 = Biotin-SGSG-PEPTIDE-acid
Peptides 2-24 & 27-43 = Biotin-SGSG-PEPTIDE-amide

| #  | Hydro | MolWt    | N-term | Sequence        | C-term |
|----|-------|----------|--------|-----------------|--------|
| 12 | 0.46  | 2,090.38 | Biotin- | SEQ.I.D.NO: 48 | —NH2   |
| 13 | 0.29  | 2,219.54 | Biotin- | SEQ.I.D.NO: 49 | —NH2   |
| 14 | 0.29  | 2,180.53 | Biotin- | SEQ.I.D.NO: 50 | —NH2   |
| 15 | 0.36  | 2,318.70 | Biotin- | SEQ.I.D.NO: 51 | —NH2   |
| 16 | 0.32  | 2,303.73 | Biotin- | SEQ.I.D.NO: 52 | —NH2   |
| 17 | 0.47  | 2,209.57 | Biotin- | SEQ.I.D.NO: 53 | —NH2   |
| 18 | 0.48  | 2,257.60 | Biotin- | SEQ.I.D.NO: 54 | —NH2   |
| 19 | 0.17  | 2,273.57 | Biotin- | SEQ.I.D.NO: 55 | —NH2   |
| 20 | 0.27  | 2,300.60 | Biotin- | SEQ.I.D.NO: 56 | —NH2   |
| 21 | 0.29  | 2,383.77 | Biotin- | SEQ.I.D.NO: 57 | —NH2   |
| 22 | 0.35  | 2,401.83 | Biotin- | SEQ.I.D.NO: 58 | —NH2   |
| 23 | 0.45  | 2,407.92 | Biotin- | SEQ.I.D.NO: 59 | —NH2   |
| 24 | 0.42  | 2,541.08 | Biotin- | SEQ.I.D.NO: 60 | —NH2   |
| 25 | 0.33  | 2,513.97 | Biotin- | SEQ.I.D.NO: 61 | —OH    |
| 27 | 0.42  | 2,283.64 | Biotin- | SEQ.I.D.NO: 62 | —NH2   |
| 28 | 0.27  | 2,425.81 | Biotin- | SEQ.I.D.NO: 63 | —NH2   |
| 29 | 0.57  | 2,228.57 | Biotin- | SEQ.I.D.NO: 64 | —NH2   |
| 30 | 0.62* | 2,223.57 | Biotin- | SEQ.I.D.NO: 65 | —NH2   |
| 31 | 0.51  | 2,165.49 | Biotin- | SEQ.I.D.NO: 66 | —NH2   |
| 32 | 0.56  | 2,112.45 | Biotin- | SEQ.I.D.NO: 67 | —NH2   |
| 33 | 0.27  | 2,207.56 | Biotin- | SEQ.I.D.NO: 68 | —NH2   |
| 34 | 0.33  | 2,345.73 | Biotin- | SEQ.I.D.NO: 69 | —NH2   |
| 35 | 0.29  | 2,330.76 | Biotin- | SEQ.I.D.NO: 70 | —NH2   |
| 36 | 0.45  | 2,236.60 | Biotin- | SEQ.I.D.NO: 71 | —NH2   |
| 37 | 0.43  | 2,276.64 | Biotin- | SEQ.I.D.NO: 72 | —NH2   |
| 38 | 0.12  | 2,292.62 | Biotin- | SEQ.I.D.NO: 73 | —NH2   |
| 39 | 0.22  | 2,319.64 | Biotin- | SEQ.I.D.NO: 74 | —NH2   |
| 40 | 0.24  | 2,402.82 | Biotin- | SEQ.I.D.NO: 75 | —NH2   |
| 41 | 0.33  | 2,387.80 | Biotin- | SEQ.I.D.NO: 76 | —NH2   |
| 42 | 0.43  | 2,393.90 | Biotin- | SEQ.I.D.NO: 77 | —NH2   |
| 43 | 0.39  | 2,527.05 | Biotin- | SEQ.I.D.NO: 78 | —NH2   |
| 44 | 0.35  | 2,471.88 | Biotin- | SEQ.I.D.NO: 79 | —OH    |

(*indicates a high hydrophobicity value)

EXAMPLE

A Typical 96 Well Plate Set-up for this Assay.

|   | 1 | 2 | 3 | 4 | 5 | 6 | 7 | 8 | 9 | 10 | 11 | 12 |
|---|---|---|---|---|---|---|---|---|---|----|----|----|
| A | 2 | 3 | 4 | 5 | 6 | 7 | 8 | 9 | 10 | 11 | 12 | 13 |
| B | 2 | 3 | 4 | 5 | 6 | 7 | 8 | 9 | 10 | 11 | 12 | 13 |
| C | 14 | 15 | 16 | 17 | 18 | 19 | 20 | 21 | 22 | 23 | 24 | 25 |
| D | 14 | 15 | 16 | 17 | 18 | 19 | 20 | 21 | 22 | 23 | 24 | 25 |
| E | 27 | 28 | 29 | 30 | 31 | 32 | 33 | 34 | 35 | 36 | 37 | 38 |
| F | 27 | 28 | 29 | 30 | 31 | 32 | 33 | 34 | 35 | 36 | 37 | 38 |
| G | 39 | 39 | 40 | 40 | 41 | 41 | 42 | 42 | 43 | 43 | 44 | 44 |
| H | +VE (4) | +VE (16) | +VE (32) | +VE (4) | +VE (16) | +VE (32) | −VE (4) | −VE (16) | −VE (32) | −VE (4) | −VE (16) | −VE (32) |

NB:
Numbers indicate the peptide in each well
Numbers in brackets indicate the dilution factor of the control antibody Absorbencies at 490 nm of the 96-wells

|   | 1 | 2 | 3 | 4 | 5 | 6 | 7 | 8 | 9 | 10 | 11 | 12 |
|---|---|---|---|---|---|---|---|---|---|----|----|----|
| A | 0.057 | 0.067 | 0.079 | 0.063 | 0.072 | 0.061 | 0.084 | 0.061 | 0.075 | 0.064 | 0.075 | 0.066 |
| B | 0.068 | 0.070 | 0.105 | 0.065 | 0.075 | 0.072 | 0.071 | 0.070 | 0.064 | 0.061 | 0.062 | 0.063 |
| C | 0.119 | 0.081 | 0.099 | 0.064 | 0.073 | 0.077 | 0.060 | 0.061 | 0.090 | 0.144 | 2.109 | 2.200 |
| D | 0.115 | 0.129 | 0.141 | 0.060 | 0.090 | 0.063 | 0.104 | 0.078 | 0.076 | 0.135 | 2.148 | 2.210 |
| E | 0.060 | 0.074 | 0.098 | 0.062 | 0.064 | 0.071 | 0.088 | 0.082 | 0.089 | 0.073 | 0.068 | 0.067 |
| F | 0.082 | 0.078 | 0.071 | 0.062 | 0.056 | 0.057 | 0.084 | 0.067 | 0.090 | 0.074 | 0.063 | 0.056 |
| G | 0.057 | 0.055 | 0.060 | 0.060 | 0.058 | 0.058 | 0.104 | 0.108 | 2.236 | 2.237 | 2.229 | 2.229 |
| H | 1.499 | 1.197 | 0.739 | 1.548 | 1.209 | 0.976 | 0.077 | 0.080 | 0.072 | 0.072 | 0.082 | 0.103 |

Figure 15:
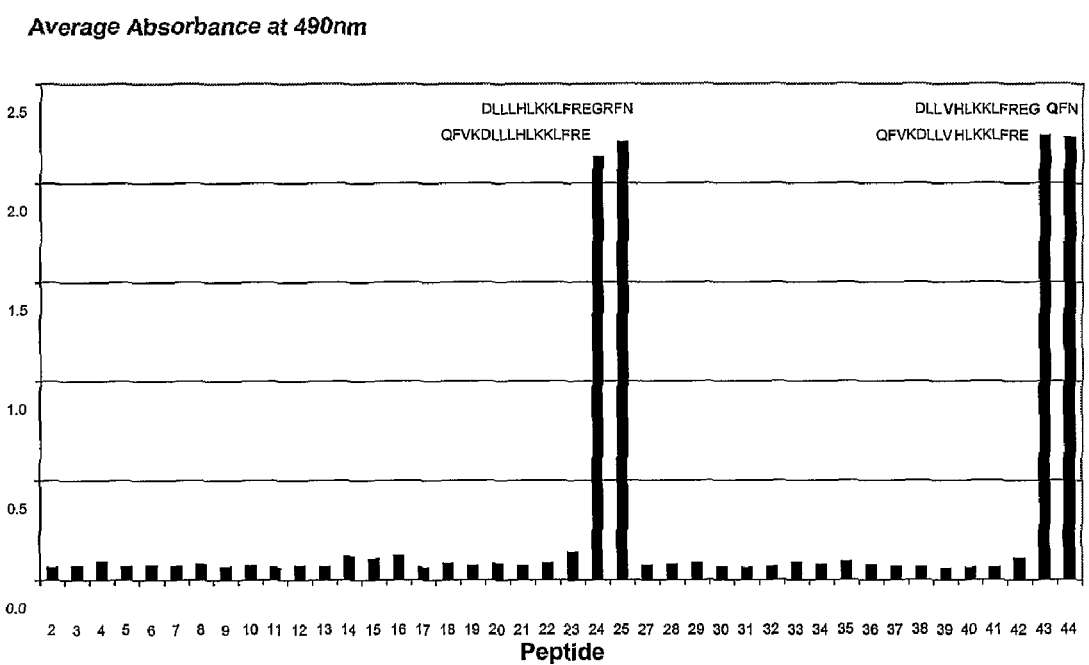
FIG. 15
An epitope mapping ELISA to determine the binding epitope for 6A1 on human and cynomolgus IL-13.

This result (one of a number of attempts) correlates to a positive result for peptides 24, 25, 43 and 44 as shown below (as well as the positive control peptides). See FIG. 15. All attempts demonstrated that peptides 24,25,43 and 44 were positive.

```
Peptide 24:    QFVKDLLLHLKKLFRE    (SEQ. I.D. NO: 80)
Peptide 25:    DLLLHLKKLFREGRFN    (SEQ. I.D. NO: 81)
Peptide 43:    QFVKDLLVHLKKLFRE    (SEQ. I.D. NO: 82)
Peptide 44:    DLLVHLKKLFREGQFN    (SEQ. I.D. NO: 83)
```

Peptides 24 and 25 are derived from hIL-13. Peptides 43 and 44 are derived from cynoIL-13.

In addition, chimaeric 6A1, L1+A1 and L2+A1 mAbs all bound to the same linear epitope at the C-terminal region in both human and cynomolgus IL-13 (data for chimaeric 6A1, L1+A1 and L2+A1 mAbs are not shown).

In summary, ELISA results indicated that parental mouse mAb 6A1, chimaeric 6A1, L1+A1 and L2+A1 mAbs all bound within the following sequence from the human IL-13 protein:

```
    DLLLHLKKLFRE       (SEQ. I.D. NO: 84)
```

And within the following sequence from the cynomolgus IL-13 protein:

```
    DLLVHLKKLFRE       (SEQ. I.D. NO: 85)
```

NB: BOLD indicates residue differences between human IL-13 and the cynomolgus IL-13 orthologue.

Accordingly it has been determined that parental mouse mAb 6A1, chimaeric 6A1, L1+A1 and L2+A1 mAbs immunospecifically bind human IL-13 between residues 97 to 108 of SEQ.I.D.NO:9.

6.8 Epitope Fine-Mappina of 6A1 using Biotinylated Peptides

A binding epitope for mAb 6A1 was determined using a peptide set based around KDLLLHLKKLFREG for binding to human IL-13 and KDLLVHLKKLFREG for binding to cynomolgus IL-13. Peptides were ordered with 1 amino acid sequentially removed from either the N or C-terminus of these parental peptide sequences (ie. KDLLLHLKKLFREG or KDLLVHLKKLFREG), in order to define the precise linear binding epitope for mAb 6A1.

An ELISA method was used to detect binding of immobilised biotinylated peptide to the parental mAb 6A1.

The peptide identification number (413 to 447) and corresponding sequences are shown below.

Peptide Sequences:

| Peptide # | N-Term | Sequence | C-Term |
|---|---|---|---|
| 413 | Biotin- | SEQ.I.D.NO: 94 | —NH2 |
| 414 | Biotin- | SEQ.I.D.NO: 95 | —NH2 |
| 415 | Biotin- | SEQ.I.D.NO: 96 | —NH2 |
| 416 | Biotin- | SEQ.I.D.NO: 97 | —NH2 |
| 417 | Biotin- | SEQ.I.D.NO: 98 | —NH2 |
| 418 | Biotin- | SEQ.I.D.NO: 99 | —NH2 |
| 419 | Biotin- | SEQ.I.D.NO: 100 | —NH2 |
| 420 | Biotin- | SEQ.I.D.NO: 101 | —NH2 |
| 421 | Biotin- | SEQ.I.D.NO: 102 | —NH2 |
| 422 | Biotin- | SEQ.I.D.NO: 103 | —NH2 |
| 423 | Biotin- | SEQ.I.D.NO: 104 | —NH2 |
| 424 | Biotin- | SEQ.I.D.NO: 105 | —NH2 |
| 425 | Biotin- | SEQ.I.D.NO: 106 | —NH2 |
| 426 | Biotin- | SEQ.I.D.NO: 107 | —NH2 |
| 427 | Biotin- | SEQ.I.D.NO: 108 | —NH2 |
| 428 | Biotin- | SEQ.I.D.NO: 109 | —NH2 |
| 429 | Biotin- | SEQ.I.D.NO: 110 | —NH2 |
| 430 | Biotin- | SEQ.I.D.NO: 111 | —NH2 |
| 431 | Biotin- | SEQ.I.D.NO: 112 | —NH2 |
| 432 | Biotin- | SEQ.I.D.NO: 113 | —NH2 |
| 433 | Biotin- | SEQ.I.D.NO: 114 | —NH2 |
| 434 | Biotin- | SEQ.I.D.NO: 115 | —NH2 |
| 435 | Biotin- | SEQ.I.D.NO: 116 | —NH2 |
| 436 | Biotin- | SEQ.I.D.NO: 117 | —NH2 |
| 437 | Biotin- | SEQ.I.D.NO: 118 | —NH2 |
| 438 | Biotin- | SEQ.I.D.NO: 119 | —NH2 |
| 439 | Biotin- | SEQ.I.D.NO: 120 | —NH2 |
| 440 | Biotin- | SEQ.I.D.NO: 121 | —NH2 |
| 441 | Biotin- | SEQ.I.D.NO: 122 | —NH2 |
| 442 | Biotin- | SEQ.I.D.NO: 123 | —NH2 |
| 443 | Biotin- | SEQ.I.D.NO: 124 | —NH2 |
| 444 | Biotin- | SEQ.I.D.NO: 125 | —NH2 |
| 445 | Biotin- | SEQ.I.D.NO: 126 | —NH2 |
| 446 | Biotin- | SEQ.I.D.NO: 127 | —NH2 |
| 447 | Biotin- | SEQ.I.D.NO: 128 | —NH2 |
| 44 (Control) | Biotin- | SEQ.I.D.NO: 79 | —OH |

EXAMPLE

A 96 Well Plate Set-up for this Assay

| | 1 | 2 | 3 | 4 | 5 | 6 | 7 | 8 | 9 | 10 | 11 | 12 |
|---|---|---|---|---|---|---|---|---|---|---|---|---|
| A | 413 | 414 | 415 | 416 | 417 | 418 | 419 | 420 | 421 | 422 | 423 | 424 |
| B | 413 | 414 | 415 | 416 | 417 | 418 | 419 | 420 | 421 | 422 | 423 | 424 |
| C | 425 | 426 | 427 | 428 | 429 | 430 | 431 | 432 | 433 | 434 | 435 | 436 |
| D | 425 | 426 | 427 | 428 | 429 | 430 | 431 | 432 | 433 | 434 | 435 | 436 |
| E | 437 | 438 | 439 | 440 | 441 | 442 | 443 | 444 | 445 | 446 | 447 | 44 |
| F | 437 | 438 | 439 | 440 | 441 | 442 | 443 | 444 | 445 | 446 | 447 | 44 |
| G | BLANK | BLANK | BLANK | BLANK | BLANK | BLANK | BLANK | BLANK | BLANK | BLANK | BLANK | BLANK |
| H | BLANK | BLANK | BLANK | BLANK | BLANK | BLANK | BLANK | BLANK | BLANK | BLANK | BLANK | BLANK |

NB:
Numbers indicate the peptide in each well

Absorbencies at 490 nm of the 96-wells

|   | 1 | 2 | 3 | 4 | 5 | 6 | 7 | 8 | 9 | 10 | 11 | 12 |
|---|---|---|---|---|---|---|---|---|---|---|---|---|
| A | 2.456 | 2.501 | 2.434 | 2.419 | 2.746 | 2.661 | 2.224 | 2.407 | 0.059 | 0.052 | 0.052 | 2.527 |
| B | 2.480 | 2.452 | 2.444 | 2.624 | 2.639 | 3.106 | 2.188 | 2.473 | 0.059 | 0.055 | 0.052 | 2.568 |
| C | 2.472 | 0.099 | 0.065 | 0.059 | 0.070 | 0.058 | 0.053 | 0.054 | 0.162 | 2.479 | 2.389 | 2.883 |
| D | 2.399 | 0.100 | 0.067 | 0.053 | 0.049 | 0.051 | 0.052 | 0.047 | 0.485 | 2.838 | 2.783 | 2.640 |
| E | 2.582 | 2.359 | 2.585 | 2.512 | 0.096 | 0.052 | 0.054 | 0.048 | 0.049 | 0.183 | 0.051 | 2.424 |
| F | 2.431 | 2.872 | 2.522 | 2.243 | 0.097 | 0.059 | 0.052 | 0.049 | 0.057 | 0.047 | 0.050 | 2.342 |
| G | 0.056 | 0.051 | 0.058 | 0.065 | 0.056 | 0.067 | 0.049 | 0.047 | 0.053 | 0.057 | 0.052 | 0.056 |
| H | 0.047 | 0.052 | 0.050 | 0.070 | 0.054 | 0.047 | 0.056 | 0.053 | 0.049 | 0.050 | 0.052 | 0.049 |

Figure 16A:
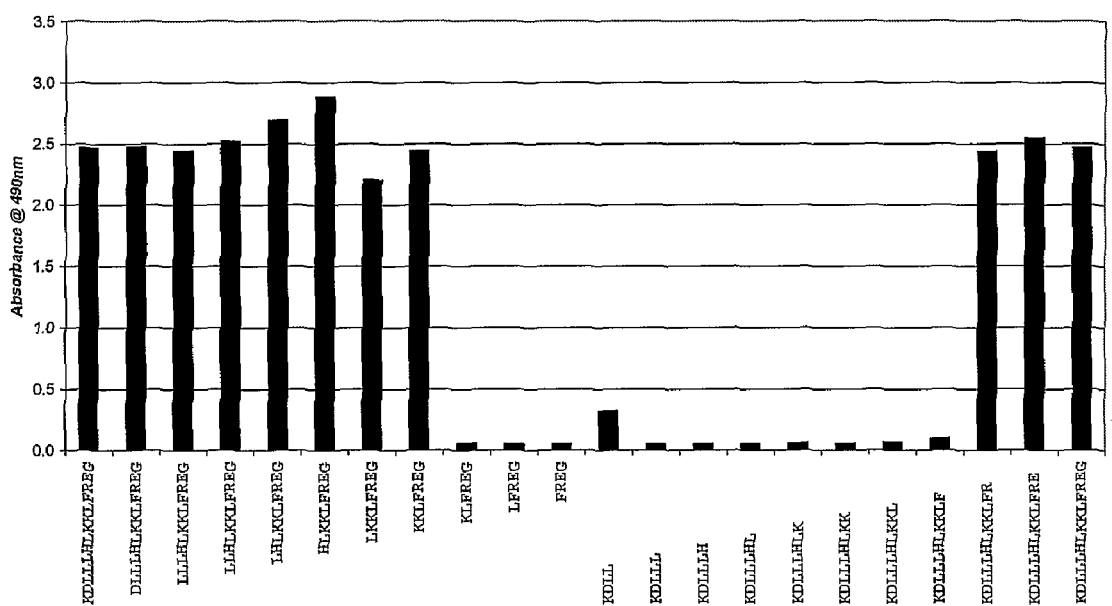
FIG. 16a
An epitope mapping ELISA to identify the fine binding specificity of 6A1 on human IL-13
Figure 16B:
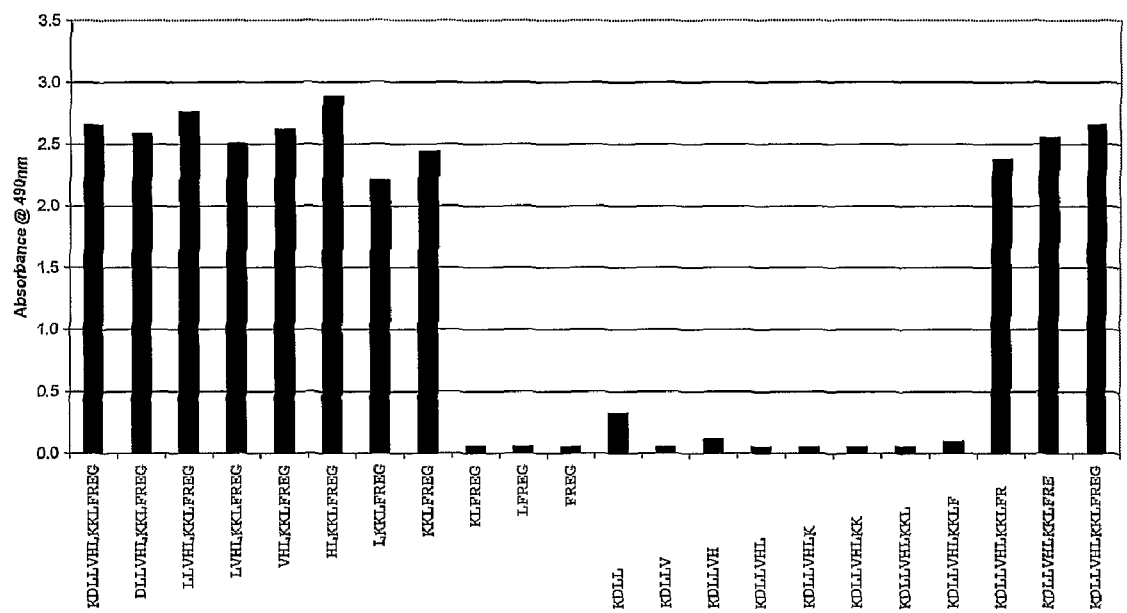
FIG. 16b
An epitope mapping ELISA to identify the fine binding specificity of 6A1 on cynomolgus IL-13

See FIGS. 16a and 16b. The results indicate that parental mAb 6A1 binds to the linear amino acid epitope KKLFR (SEQ I.D.NO:137) in the C-terminal region of both human IL-13 and the cynomolgus IL-13 orthologue.

In addition chimaeric 6A1, L1+A1 and L2+A1 mAbs all bound to the same Linear epitope (ie. KKLFR (SEQ I.D.NO: 137) at the C-terminal region in human IL-13 (data for chimaeric 6A1, L1+A1 and L2+A1 mAbs are not shown). Subsequently it was shown that parental mAb 6A1 bound the same epitope in cynomolgus IL-13.

In summary, ELISA results indicated that parental mouse mAb 6A1, chimaeric 6A1, L1+A1 and L2+A1 mAbs all bound within the following sequence from the human IL-13 protein: KKLFR (SEQ I.D.NO:137).

6.9 Alanine Scanning of the 6A1 Binding Epitope using Biotinylated Peptides

In order to identify certain key residues involved in the interaction of IL-13 with mAb 6A1, an alanine scanning approach was adopted using a parental peptide sequence containing the KKLFR (SEQ I.D.NO:137) binding epitope (ie.QFVKDLLLHLKKLFREGRFN (SEQ I.D.NO:129)). For this analysis, peptides were generated (supplied by AnaSpec Inc) where one amino acid was sequentially substituted for an alanine residue at each amino acid position in the KKLFR (SEQ.I.D.NO:137)epitope (and also for each of the amino acids directly bordering this epitope).

An ELISA method was used to detect binding of immobilised biotinylated peptide to the parental mAb 6A1 and L1+A1.

The peptides generated for this analysis and a corresponding peptide identification number are shown below:

| Peptide # | N-Term | Sequence |
|---|---|---|
| 1 | Biotin | SEQ.I.D.NO: 129 |
| 62 | Biotin | SEQ.I.D.NO: 130 |
| 63 | Biotin | SEQ.I.D.NO: 131 |
| 64 | Biotin | SEQ.I.D.NO: 132 |
| 65 | Biotin | SEQ.I.D.NO: 133 |
| 66 | Biotin | SEQ.I.D.NO: 134 |

-continued

| Peptide # | N-Term | Sequence |
|---|---|---|
| 67 | Biotin | SEQ.I.D.NO: 135 |
| 68 | Biotin | SEQ.I.D.NO: 136 |

Results: Absorbencies at 490 nm

Average test results (n=2).

For parental (murine) 6A1 mAb:

| | Peptide number | | | | | | | |
|---|---|---|---|---|---|---|---|---|
| | 1 | 62 | 63 | 64 | 65 | 66 | 67 | 68 |
| Average $A_{490}$ | 3.543 | 3.489 | 3.2795 | 1.468 | 3.8495 | 3.5995 | 0.595 | 3.581 |

For L1+A1:

| | Peptide number | | | | | | | |
|---|---|---|---|---|---|---|---|---|
| | 1 | 62 | 63 | 64 | 65 | 66 | 67 | 68 |
| Average $A_{490}$ | 2.8535 | 2.832 | 2.6535 | 1.8175 | 3.0165 | 2.84 | 0.816 | 2.8085 |

Figure 17A:
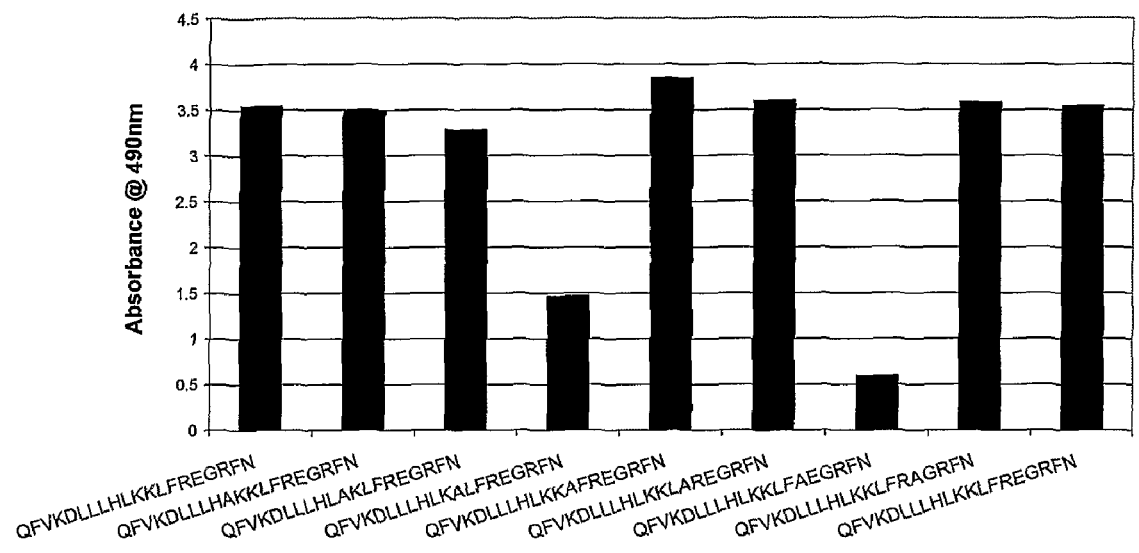
FIG. 17a
An epitope mapping ELISA to determine the key amino acid residues required for binding of 6A1 to human IL-13
Figure 17B:
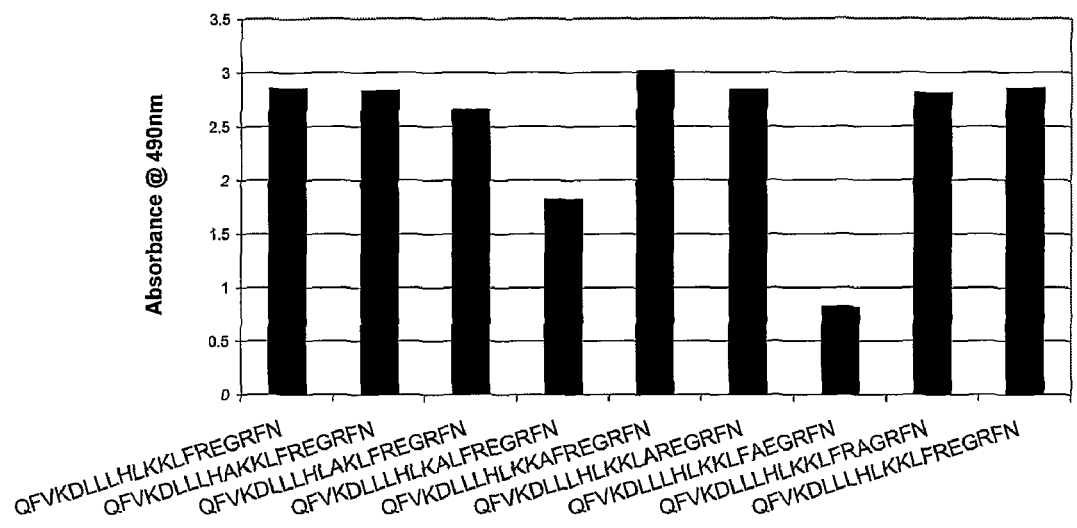
FIG. 17b
An epitope mapping ELISA to determine the key amino acid residues required for binding of L1+A1 to human IL-13.

See FIGS. 17a and 17b.

These data suggest that the key amino acid residues involved in the interaction of mAb 6A1 or L1+A1 with human IL-13 are arginine (R) at position 107, and lysine (K) at position 103.

This analysis was repeated, but using 6A1 and L1+A1 mAbs at a range of concentrations in order to confirm this effect over a mAb dilution range.

The parental mouse mAb 6A1 (FIG. 17c) and the humanised candidate L1+A1 were assayed for binding to the alanine scanning peptides (SEQ I.Ds 129, 131-135) at varying concentrations. As the peptides had to be split across two 96 well plates, the parental sequence peptide containing no alanine substitutions (SED I.D: 129) was assayed on both plates—hence two results per graph. This was to determine if there was any major plate-to-plate variation and in both cases, there was no apparent variation.

The peptides containing the substitutions K103A, L105A and F106A (SEQ I.Ds 131, 133 and 134 respectively, residue numbering as set forth in SEQ ID 9) showed very similar binding to the mAbs as the parental peptide (SEQ ID 129)—therefore these residues are not critical for 6A1/L1+A1 binding to IL-13. Peptides containing the substitutions K104A and R107A (SEQ I.Ds 132 and 135 respectively, residue numbering as set forth in SEQ ID 9) however, show reduced binding of 6A1/L+A1 compared to the parental peptide (SEQ ID 129), particularly at the lower concentrations, indicating that these residues are critical for optimal binding of 6A1/L1+A1 to IL-13.

Figure 17C:
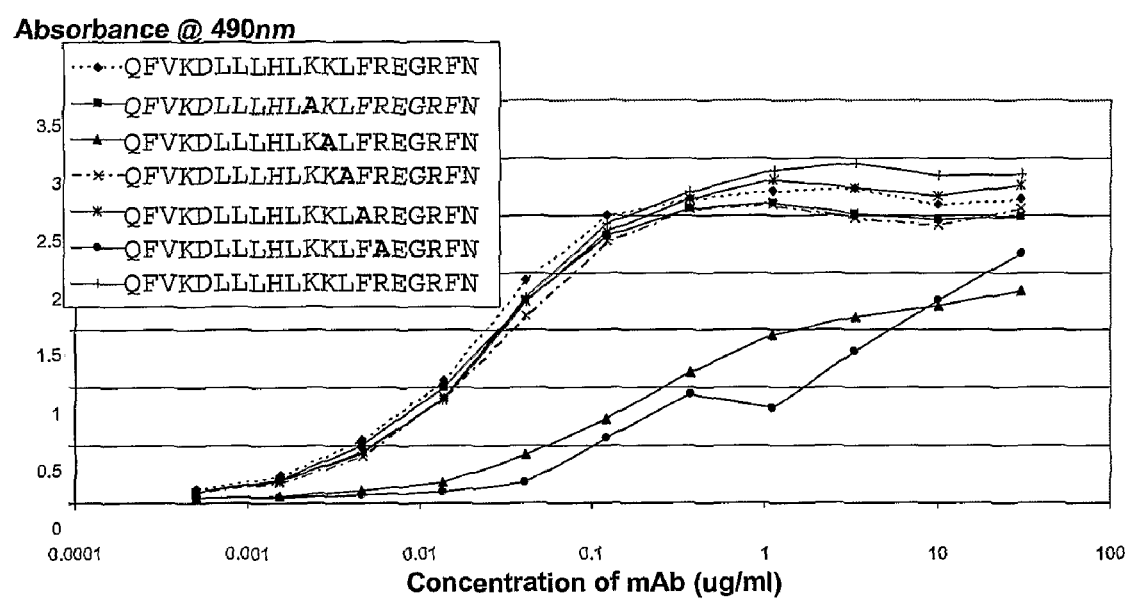
FIG. 17c is a graph illustrating the alanine scanning analysis for the parental (murine) 6A1.

See FIG. 17c.

These data indicate that the key amino acid residues involved in the interaction of parental (i.e. murine) 6A1 or L1+A1 with human IL-13 are arginine (R) at position 107, and lysine (K) at position 103 of SEQ.I.D.NO:9.

Section 7.—Materials and Methods

In the following section the following materials and methods were used where appropriate. These are representative material and methods. Minor changes in materials and methods may have occurred in repeat experiments.

Materials
SV Total RNA Isolation System: Promega Z3100
Access RT-PCR System: Promega A1250
QIAquick Gel Extraction kit: Qiagen 28704
Gel loading solution: Sigma G7654
Agarose: Invitrogen 15510-019
Ethidium bromide: Sigma E1510
TAE buffer: in-house
100 bp DNA ladder: New England BioLabs N3231S
TA cloning kit: Invitrogen 45-0046
TOP10F' cells: Invitrogen 44-0300
L-agar+100 µg/ml ampicillin: in-house
X-Gal, 50 mg/ml in DMF: Promega V394A
AmpliTaq DNA Polymerase: Applied Biosystems
10× PCR buffer: Applied Biosystems
E-Gel 1.2% agarose: Invitrogen G501801
LB medium+100 µg/ml ampicillin: in-house
QIAprep Spin Miniprep kit: Qiagen 27106
MinElute PCR Purification kit: Qiagen 28004
NEBuffer2 10×conc: New England Biolabs B7002S
Purified BSA 100×conc: New England Biolabs B9001S
BsiW I: New England Biolabs R0553L
Hind III: Promega R604A
Spe I: New England Biolabs R0133S
LigaFast Rapid DNA Ligation System: Promega M8225
MAX Efficiency DH5α Chemically Competent cells: Invitrogen 18258-012
SOC media: in-house
QIAfilter Plasmid Maxi kit: Qiagen 12263
Dulbecco's MEM with Glutamax-1: Invitrogen 31966-021
Optimem 1 with Glutamax-1: Invitrogen 51985-026
TransFast Transfection Reagent: Promega E2431
1 ml HiTrap rProtein A Sepharose FF: Amersham Biosciences 17-5079-01
Dulbecco's PBS: Sigma D8537
ImmunoPure IgG Elution Buffer: Pierce 21009
1M Trizma-HCl pH8.0: Sigma T2694
ProofStart DNA Polymerase: Qiagen 1016816
ProofStart PCR buffer: Qiagen 1016961

7.1. Human or Cynomolgus IL-13 Binding ELISA

This assay describes an ELISA that detects binding of an antibody to human or cynomolgus IL-13. It is a sandwich ELISA format.

7.1.1 Materials
1. Nunc Immunoplate 1 F96 Maxisorp (Life Technologies, 4-39454A)
2. Human IL-13 (Cambridge Biosciences, cat. no. CH1-013)
3. Cynomolgus IL-13 (made by GlaxoSmithkline)
4. Goat anti-human IL-13 polyclonal antibody (R+D Systems, cat. no. AF-213-NA)
5. Anti-human IgG-HRP (Sigma, Cat No. A-6029)
6. Anti-mouse IgG-HRP (Sigma, Cat No. A-9309)
7. Carbonate/bicarbonate buffer (Sigma; cat. no. C-3041)
8. TBST [Tris buffered saline (6.06 g Tris+8.06 g NaCl+0.2 g KCl+H20 to 1 L)+0.05% Tween 20]
9. BSA (Sigma A-7030)
10. OPD (Sigma, Cat. No. P-9187)
11. Sulphuric acid 7.1.2 Method
1. Blocking solution is 3% BSA+TBST
2. Washing solution is TBST
3. Coat 'Nunc Maxisorp' ELISA plates with 50 ul of 5 g/ml goat anti-human IL-13 polyclonal antibody (R+D Systems, cat. no. AF-213-NA. Made up at a stock concentration of 500 ug/ml according to maufacturers instructions, and stored in aliquots at −20C) in carbonate/bicarbonate buffer (Sigma; cat. no. C-3041, made up as per maufacturers instructions), cover with a plate sealer and incubate O/N at 4° C.
4. Block with 100 ul of 3% BSA/TBST incubate at rtp for 1 hr.
5. Wash X3 in TBST (at least 200 ul wash solution per well per wash).
6. Add 20 ng per well (in a 50 ul volume) human IL-13 (Cambridge Bioscience, cat. no. CH1-013. Made up at a stock concentration of 10 ng/ul according to maufacturers instructions, and stored in aliquots at −20C) or 20ng per well cynomolgus IL-13, in block solution and incubate at room temperature for 1 hr.
7. Wash X3 in TBST.
8. Add 50 ul antibody sample (titrate out to obtain endpoint titre data, if required) in block solution, incubate at rtp for 1 hr.
9. Wash X3 in TBST.
10. For 6A1 chimaeric antibody or humanised antibody, detect binding using 50 ul per well anti-human IgG-HRP (Sigma, Cat No. A-6029) at a 1/2000 dilution in block solution for 1 hr at rtp. For 6A1 mouse monoclonal antibody, detect binding using 50 ul per well anti-mouse IgG-HRP (Sigma, Cat No. A-9309) at a 1/1000 dilution in block solution for 1 hr at rtp.
11. Wash X3 in TBST.
12. Develop with 100 ul OPD (Sigma, Cat. No. P-9187. Made up as per maufacturers instructions), stop with 50 ul 3M $H_2SO_4$, read at an absorbance of 490 nm. Development time is ~12 minutes.

7.2. Human IL-13 Binding to the Human IL-13Rα1 Chain ELISA

This ELISA determines whether an antibody can inhibit human IL-13 binding to the human IL-13Rα1chain.

7.2.1 Materials
1. Nunc Immunoplate 1 F96 Maxisorp (Life Technologies, 4-39454A)
2. Human IL-13Rα1-Fc (R&D Systems, cat.no. 146-IR)
3. Det-1 tagged human IL-13 (made in-house)
4. Biotinylated anti-human IL-13 (R&D Systems, cat. no. BAF213)
5. Streptavidin-HRP
6. Carbonate/bicarbonate buffer (Sigma; cat. no. C-3041)
7. TBST [Tris buffered saline (6.06 g Tris+8.06 g NaCl+ 0.2g KCl+H20 to 1 L)+0.05% Tween 20]
8. BSA (Sigma A-7030)
9. OPD (Sigma, Cat. No. P-9187)
10. Sulphuric acid 7.2.2 Method
1. Blocking solution is 3% BSA+TBST
2. Washing solution is TBST
3. Coat 'Nunc Maxisorp' ELISA plates with 50 ul of 5 ng/ul human IL-13Rα1-Fc in carbonate/bicarbonate buffer. Cover with a plate sealer and incubate overnight at 4° C.
4. Block with 100 ul of 3% BSA/TBST incubate at rtp for 1 hr.
5. Wash x3 TBST (at least 200 ul wash solution per well per wash).
6. In a total volume of 50 ul, pre-incubate 0.04 ng/ul det-1 tagged human IL-13 with antibody sample (titrated) in block solution for 30 minutes. Add the pre-incubated sample to the receptor-coated ELISA plate and incubate at room temperature for 1 hr.
7. Wash x3 in TBST
8. Detect any bound human IL-13 using 50 ul per well biotinylated anti-human IL-13 diluted at 1 ug/ml. Incubate for 1 hour at room temperature
9. Wash x3 in TBST
10. Add 50 ul per well streptavidin-HRP conjugate at 1/1000 dilution. Incubate for 1 hour at room temperature.
11. Wash x3 in TBST
12. Develop with 100 ul per well OPD (Sigma, Cat. No. P-9187. Made up as per maufacturers instructions), stop with 50 ul per well 3M $H_2SO_4$, read at an absorbance of 490 nm. Development time is ~2 minutes.

7.3. Human IL-13 Binding to the Human IL-13Rα2 Chain ELISA

This ELISA determines whether an antibody can inhibit human IL-13 binding to the human IL-13Rα2 chain.

7.3.1 Materials
1. Nunc Immunoplate 1 F96 Maxisorp (Life Technologies, 4-39454A)
2. Anti-human IgG (Sigma, cat. no. I-3382)
3. Human IL-13Rα2-Fc (R&D Systems, cat.no. 614-IR)
4. Det-1 tagged human IL-13 (made in-house)
5. Biotinylated anti-human IL-13 (R&D Systems, cat. no. BAF213)
6. Streptavidin-HRP
7. Carbonate/bicarbonate buffer (Sigma; cat. no. C-3041)
8. TBST [Tris buffered saline (6.06g Tris+8.06g NaCl+ 0.2g KCl+H20 to 1 L)+0.05% Tween 20]
9. BSA (Sigma A-7030)
10. OPD (Sigma, Cat. No. P-9187)
11. Sulphuric acid 7.3.2 Method
1. Blocking solution is 3% BSA+TBST
2. Washing solution is TBST
3. Coat 'Nunc Maxisorp' ELISA plates with 50 ul of anti-human IgG diluted to 1/1000 in carbonate/bicarbonate buffer. Cover with a plate sealer and incubate overnight at 4° C.
4. Block with 100 ul of 3% BSA/TBST incubate at rtp for 1 hr.
5. Wash X3 TBST (at least 200 ul wash solution per well per wash).
6. Add 50 ul per well of 1 ug/ml human IL-13Rα2-Fc in block solution. Cover with a plate sealer and incubate at room temperature for 1 hr.
7. Wash x3 in TBST
8. In a total volume of 50 ul, pre-incubate 0.004 ng/ul det-1 tagged human IL-13 with antibody sample (titrated) in block solution for 30 minutes. Add the pre-incubated sample to the receptor-coated ELISA plate and incubate at room temperature for 1 hr.
9. Wash x3 in TBST
10. Detect any bound human IL-13 using 50 ul per well biotinylated anti-human IL-13 diluted at 1 ug/ml. Incubate for 1 hour at room temperature.
11. Wash x3 in TBST
12. Add 50 ul per well streptavidin-HRP conjugate at 1/1000 dilution. Incubate for 1 hour at room temperature.
13. Wash x3 in TBST
14. Develop with 100 ul per well OPD (Sigma, Cat. No. P-9187. Made up as per maufacturers instructions), stop with 50 ul per well 3M $H_2SO_4$, read at an absorbance of 490 nm. Development time is ~2 minutes.

7.4. IL-13 Neutralisation Bioassay (TF-1 Cell Proliferation Assay)

This is an IL-13 bioassay that can be used to determine the neutralisation capacity of an anti-IL-13 antibody. The method described below uses recombinant human or cynomolgus IL-13. Mammalian-expressed human IL-13 or the Q130 human IL-13 variant can also be used in this assay too. (TF-1 cells also proliferate in response to human IL5. This assay was also used to assess the neutralisation capacity of 6A1 on human IL5 bioactivity).

7.4.1 Materials
1. TF-1 cell line (obtained in-house)
2. 96 well tissue culture plates (Invitrogen)
3. Human IL-13 (Cambridge Bioscience, cat. no. CH1-013)
4. CellTiter 96 non-radioactive cell proliferation assay (Promega, Cat. No. G4000)

7.4.2 Method
1. Method to measure the ability of an anti-human IL-13 mAb to neutralise the bioactivity of recombinant human or cynomolgus IL-13 in a TF-1 cell bioassay (TF-1 cell line obtained in-house, not the ATCC version).
2. This assay is performed in sterile 96 well tissue culture plates (Invitrogen), under sterile conditions. All tests are performed in triplicate.
3. Pre-incubate long/ml human IL-13 (Cambridge Bioscience, cat. no. CH1-013. Make up at a stock concentration of 100 ng/ul according to maufacturers instructions using sterile technique in a class 2 tissue culture hood, store in small aliquots at −20C) or 10 ng/ml cyno IL-13 (obtained in-house from CA) with various dilutions of the anti-human IL-13 mAb (diluted from 6 ug/ml in 3 fold dilutions down to 0.025 ug/ml) in a total volume of 50 ul for 1 hour at 37C. Also included will be positive control wells, having IL-13 present but no anti-human IL-13 mAb. In addition, negative control wells will have no IL-13 and no anti-human IL-13 mAb present. Use a sterile, low protein binding, round bottom 96 well plate for this pre-incubation. (Note that the concentration of IL-13 and anti-human IL-13 mAb will be halved at a later stage when cells are added).

4. Plate out 50 ul of TF-1 cells at $2\times10^5$ per ml in a sterile 96 well tissue culture plate. After the 1 hour pre-incubation, add the IL-13 and anti-human IL-13 mAb sample to the cells. The final 100 ul assay volume, containing various anti-human IL-13 mAb dilutions, recombinant IL-13 and TF-1 cells, is incubated at 37° C. for ~70 hours in a humidified $CO_2$ incubator.

5. At ~66 hrs, scan the wells to confirm that they are sterile and that no bacterial contamination has occurred.

6. Add 15 ul of filter sterilised MTT substrate per well (Cat. No. G4000, Promega. Made up as per maufacturers instructions) for the final 4 hours of incubation.

7. Stop the reaction with 100 ul of stop solution (provided in the MTT kit) to solubilise the metabolised blue formazan product. Leave for at least 2 hours, then pipette up and down to help dissolve the crystals. Alternatively, cover with a plate sealer and leave at 4C O/N, then pipette up and down the next day (this is easier in terms of pipefting)

8. Read the absorbance of the solution in each well in a 96-well plate reader at 570 nm wavelength.

9. The capacity of the anti-human IL-13 mAb to neutralise human or cynomolgus IL-13 bioactivity is expressed as, that concentration of anti-human IL-13 mAb required to neutralise the bioactivity of a defined amount of human or cynomolgus IL-13 (5 ng/ml) by 50% (=$ND_{50}$). The lower the concentration required, the more potent the neutralisation capacity.

EXAMPLE

A 96 Well Plate Set-up for this Assay.

| Sample 1 | | | | | | | | | | | Antibody positive |
|---|---|---|---|---|---|---|---|---|---|---|---|
| | 1 | 2 | 3 | 4 | 5 | 6 | 7 | 8 | 9 | 10 | 11 | 12 |
| A | 3 ug/ml anti-hIL-13 mAb+ IL-13 + TF-1 | | | mAb sample 2 | | | mAb sample 3 | | | 3 ug/ml anti-hIL-13 poly + IL-13 + TF-1 | | |
| B | 1 ug/ml anti-hIL-13 mAb+ IL-13 + TF-1 | | | | | | | | | 1 ug/ml anti-hIL-13 poly + IL-13 + TF-1 | | |
| C | 0.33 ug/ml anti-hIL-13 mAb+ IL-13 + TF-1 | | | ↓ | | | ↓ | | | 0.33 ug/ml anti-hIL-13 poly + IL-13 + TF-1 | | |
| D | 0.11 ug/ml anti-hIL-13 mAb+ IL-13 + TF-1 | | | | | | | | | 0.11 ug/ml anti-hIL-13 poly + IL-13 + TF-1 | | |
| E | 0.037 ug/ml anti-hIL-13 mAb + IL-13 + TF-1 | | | | | | | | | 0.037 ug/ml anti-hIL-13 poly + IL-13 + TF-1 | | |
| F | 0.0123 ug/ml anti-hIL-13 mAb + IL-13 + TF-1 | | | | | | | | | 0.0123 ug/ml anti-hIL-13 poly + IL-13 + TF-1 | | |
| G | Positive control for TF-1 cell proliferation = TF-1 cells + IL-13 (no mAb, 12 wells) | | | | | | | | | | | |
| H | Control for background = Just TF-1 cells present (no IL-13, no mAb sample, 12 wells) | | | | | | | | | | | |

7.5. Human IL-4 Binding ELISA

This assay describes an ELISA that detects binding of an antibody to human IL-4. It is a sandwich ELISA format.

7.5.1 Materials
1. Nunc Immunoplate 1 F96 Maxisorp (Life Technologies, 4-39454A)
2. Human IL-4 (R+D Systems, cat. no.)
3. Goat anti-human IL-4 polyclonal antibody (R+D Systems, Cat. No. AF-204-NA)
4. Biotinylated rat anti-human IL-4 monoclonal antibody (BD/Pharmingen, Cat. No.)
5. Anti-mouse IgG-HRP (Dako, Cat No. P0260)
6. Anti-mouse IgG-HRP (Sigma, Cat No. A-9309)
7. Carbonate/bicarbonate buffer (Sigma; cat. no. C-3041)
8. PBST (PBS+0.05% Tween 20)
9. BSA (Sigma A-7030)
10. OPD (Sigma, Cat. No. P-9187)
11. Sulphuric acid 7.5.2 Method
1. Blocking solution is 3% BSA in PBST
2. Washing solution is PBST
3. Coat 'Nunc Maxisorp' ELISA plates with 50 ul of 5 ug/ml goat anti-human IL-4 polyclonal antibody (R+D Systems, cat. no. AF-204-NA. Made up at a stock concentration of 500 ug/ml according to maufacturers instructions, and stored in aliquots at −20C) in carbonate/bicarbonate buffer (Sigma; cat. no. C-3041, made up as per manufacturers instructions), cover with a plate sealer and incubate O/N at 4° C.
4. Block with 100 ul of 3% BSA/PBST incubate at room temperature pressure (rtp) for 1 hr.
5. Wash X3 in PBST (at least 200 ul wash solution per well per wash).
6. Add 1 ng/ml (in a 50 ul volume) human IL-4 in block solution and incubate at room temperature for 1 hr.
7. Wash X3 in PBST.
8. Add 50 ul antibody sample (titrate out to obtain end-point titre data, if required) in block solution, incubate at rtp for 1 hr. As a positive control for binding to human IL-4, use a biotinylated anti-human IL-4 monoclonal antibody (titrated out).
9. Wash X3 in PBST.
10. For 6A1 mouse monoclonal antibody, detect binding using 50 ul per well anti-mouse IgG-HRP (Sigma, Cat No. A-9309) at a 1/1000 dilution in block solution for 1 hr at rtp. For 6A1 chimaeric antibody or humanised antibody, detect binding using 50 ul per well anti-human IgG-HRP (Sigma, Cat No. A-6029) at a 1/2000 dilution in block solution for 1 hr at rtp. For the positive control biotinylated rat anti-human IL-4 monoclonal antibody, detect using a streptavidin-HRP conjugated antibody. (Alternatively, the anti-mouse HRP antibody, P0260, will detect both 6A1 and the biotinylated rat anti-human IL-4 monoclonal antibody).
  11. Wash X3 in PBST.
  12. Develop with 100 ul OPD (Sigma, Cat. No. P-9187. Made up as per maufacturers instructions), stop with 50 ul 3M $H_2SO_4$, read at an absorbance of 490 nm.

7.6. Epitope Mapping ELISA

This assay describes an ELISA that detects binding of mouse mAb 6A1 to human or cynomolgus IL-13 peptides.

7.6.1 Materials
  1. Nunc Immunoplate 1 F96 Maxisorp (Life Technologies, 4-39454A)
  2. ImmunoPure© Streptavidin (Pierce, cat. no. 21125)
  3. PBST (Phosphate buffered saline+0.05% Tween 20)
  4. BSA (Sigma A-7030)
  5. Human and cynomolgus IL-13 16 mer peptides, offset=4 (Mimotopes custom order)
  6. Positive and negative control 20 mer peptides (Supplied with Mimotopes custom order)

7.6A1 MAb
  8. Control Ab (Supplied with Mimotopes custom order)
  9. Rabbit anti-mouse Ig HRP conjugated (DAKO, code no. P0260)
  10. OPD (Sigma, Cat. No. P-9187)
  11. 3M Sulphuric acid 7.6.2 Method
  1. Blocking solution is 3% BSA+PBST.
  2. Washing solution is PBST.
  3. Coat 'Nunc Maxisorp' ELISA plates with 100 µl of 5 µg/ml ImmunoPure© Streptavidin (Pierce, cat. no. 21125 made up at a stock concentration of 1 mg/ml according to manufacturers instructions, and stored in aliquots at +4° C.) using PBST as a diluent. Incubate O/N at 37° C. to allow solution to dry.
  4. Block with 200 µl of 3% BSA/PBST. Add plate sealer and incubate at rtp for 1 hr.
  5. Wash X3 in PBST (at least 200 µl wash solution per well per wash).
  6. In duplicate and using PBST as a diluent, add 100 µl per well (except control wells) of 1,000-fold dilutions of each peptide (dissolved as per manufacturers instructions in 200 µl 40% Acetonitrile 60% Water, then aliquoted in 10-fold dilutions in the same solvent and stored at −20° C.).
  7. In the control wells, in duplicate and using PBST as a diluent add 100 µl per well of 10-fold dilutions of control peptides (dissolved as per manufacturers instructions in 1 ml 40% Acetonitrile 60% Water and stored at −20° C.). Add plate sealer and incubate at rtp for 1 hr on a shaking table.
  8. Wash X3 in PBST (at least 200 µl wash solution per well per wash).
  9. Add 100 per well (except control wells) of 1.506 µg/ml mouse mAb in PBST.
  10. Add 100 µl per well to control wells only, 4, 16 and 32-fold dilutions of control antibody (used as supplied by the manufacturer and stored at −20° C.) using PBST as a diluent. Add plate sealer and incubate at rtp (room temperature and pressure) for 1 hr on a shaking table.
  11. Wash X3 in PBST (at least 200 µl wash solution per well per wash).
  12. Add 100 per well of 2,000-fold dilution of rabbit anti-mouse Ig HRP-conjugated (DAKO, code no. P0260 used as supplied, stored at+4° C.) using PBST as a diluent. Add plate sealer and incubate at rtp for 1 hr on a shaking table.
  13. Wash X3 in PBST (at least 200 µl wash solution per well per wash).
  14. Develop with 100 µl OPD (Sigma, Cat. No. P-9187. Made up as per manufacturers instructions), stop with 50 µl 3M $H_2SO_4$, read at an absorbency of 490 nm. Development time is ~10 minutes.

7.7. Epitope Fine Mapping ELISA

This assay describes an ELISA that detects binding of mAb 6A1 to human or cynomolgus IL-13 peptides.

7.7.1 Materials
  1. Nunc Immunoplate 1 F96 Maxisorp (Life Technologies, 4-39454A)
  2. ImmunoPure© Streptavidin (Pierce, cat. no. 21125)
  3. PBST (Phosphate buffered saline+0.05% Tween 20)
  4. BSA (Sigma A-7030)
  5. Human and cynomolgus IL-13 partial window net peptides (14-mer truncated by one amino acid at a time from both the N- and C-terminal ends; Mimotopes custom order)
  6. Positive control 16 mer peptide (Supplied with previous Mimotopes custom order)
  7. 6A1 mAb (made in-house)
  8. Goat anti-mouse IgG (Fc specific) HRP conjugated antibody (Sigma A-9309)
  9. OPD (Sigma, Cat. No. P-9187)
  10. 3M Sulphuric acid 7.7.2 Method
  1. Blocking solution is 3% BSA+PBST.
  2. Washing solution is PBST.
  3. Coat 'Nunc Maxisorp' ELISA plates with 100 µl of 5 µg/ml ImmunoPure© Streptavidin in ultra pure water (Pierce, cat. no. 21125 made up at a stock concentration of l mg/ml according to manufacturer's instructions, and stored at+4° C.). Incubate overnight at+37° C.
  4. Block with 200 µl of 3% BSA in PBST. Add plate sealer and incubate overnight at +4° C.
  5. Wash X3 in PBST (at least 200 µl wash solution per well per wash).
  6. In duplicate and using 3% BSA in PBST as a dilutent, add 100µl per well of 1,000-fold dilutions of each peptide (dissolved as per manufacturers instructions in 200 µl of 40% Acetonitrile 60% Water and stored at −20° C.). Add plate sealer and incubate at room temperature for 1 hour on a shaking table.
  7. Wash X3 in PBST (at least 200 µl wash solution per well per wash).
  8. Add 100 µl per well of 3 µg/ml 6A1 diluted in 3% BSA in PBST. Add plate sealer and incubate at room temperature for 1 hour on a shaking table.
  9. Wash X3 in PBST (at least 200 µl wash solution per well per wash).
  10. Add 100 µl per well of 1,000-fold dilution of goat anti-mouse IgG HRP-conjugated antibody (Sigma A-9309 used as supplied, stored at +4° C.) using 3% BSA in PBST as a dilutent. Add plate sealer and incubate at room temperature for 1 hour on a shaking table.

11. Wash X3 in PBST (at least 200 μl wash solution per well per wash).
12. Develop with 100 μl OPD (Sigma, Cat. No. P-9187. Made up as per manufacturers instructions), stop with 50 μl 3M $H_2SO_4$, read at an absorbency of 490 nm. Development time is ~10 minutes.

7.8 Biacore™ Method Humanised Constructs for IL13 Antibody vs Full Length IL13

The kinetics analysis was performed on a Biacore 3000 machine, using an antibody capture method. Briefly, for the chimeric 6A1 and humanised antibody constructs Protein A capture was used, whilst for the parental murine 6A1 antibody, capture was by a anti-mouse Fc antibody supplied by Biacore.

Briefly, the method is as follows, the capture ligand was immobilised to a CM5 Biosensor chip by primary amine coupling in accordance with Biacore standard protocols and using the reagents supplied in Biacores' primary amine coupling kit. The method involves activation CM5 sensor surface by passing a solution of 50 mM N-hydroxy-succinimide (NHS) and 200 mM N-ethyl-N'-dimethylaminopropyl carbonide (EDC) over the surface. Then, the capture ligand (dissolved in acetate buffer pH5 or pH4.5) was coupled to the activated sensor surface after which any still activated esters were blocked by an injection of 1M ethanolamine hydrochloride, pH8.5.

The candidate antibody was then passed over the Protein A or anti-mouse Fc antibody surface, depending on whether it was human or mouse in origin and captured. Once a stable binding signal was seen IL13 was passed over the captured antibody surface at various defined concentrations. The subsequent binding curves were analysed with Biacore analysis software BIAeval v4.1 to determine kinetics. The experiments were carried out using Biacore HBS-EP buffer.

7.8.1 Biacore™ Method for IL-13 Antibody vs Peptide

The kinetics analysis was performed on a Biacore 3000 machine using direct binding of antibody to immobilised IL-13 peptide. Briefly, IL-13 biotinylated peptide was captured using a Biacore SA (strepavidin) Biosensor chip. The antibodies were then passed over the sensor surface at various concentrations. The subsequent binding curves were analysed with Biacore analysis software BIAeval 4.1 to determine kinetics. The experiment was carried out using Biacore HBS-EP buffer

8. Efficacy of L1+A1 Humanised anti-IL-13 mAb in Cynomolgus Asthma Model.

This section is prophetic.

The model of Ascaris suum-induced (A.suum) pulmonary bronchoconstriction in cynomolgus monkeys (*Macaca fascicularis*) is recognised as a non-clinical model of or related to asthma in humans (Patterson R, et al *Trans. Assoc. Am. Physicians* 1980 93:317-325; Patterson R, et al *J. Lab. Clin. Med.* 1983 101:864-872).

In this model, animals having an innate pulmonary sensitivity to A.suum are exposed to nebulised A.suum to induce an asthmatic response. This asthmatic response can be characterised by measuring airways hyper-responsiveness (AHR), cellular infiltration as measured in broncho alveolar lavage (BAL) fluid and serum IgE levels. Experimental methods are similar to those previously described by Mauser P, et al in Am. J. Resp. Crit. Care Med. 1995 204:467-472 and by Evanoff H, et al in Immunologic Investigation 1992 21:39.

This study uses 30 animals, preselected for entry having demonstrated a positive bronchoconstrictor response to a specific dose of A.suum antigen. A.suum is administered at the optimal response dose (ORD) for each animal. It is a predetermined dose of A.suum that produces an increase in $R_L$ (lung resistance) of at least 40% and a decrease in $C_{DYN}$ (dynamic compliance) of at least 35%, by aerosol inhalation (for a single dose given over 15 breaths using a neublizer).

The study takes place in 2 phases. During phase 1, AHR is assessed in response to intravenous (i/v) histamine challenge (that is a dose of histamine sufficient to induce an increase in $R_L$ of at least 30% above baseline ($PC_{30}$)) both before (the baseline pulmonary function assessment on day 1) and after (on day 11) administering A.suum antigen (on days 9 and 10, when A.suum is administered at an optimal pre-determined dose for each animal by aerosol inhalation).

Phase 2 is identical to phase 1 except that animals receive treatment with antibody (see below), each antibody is given as 3 doses of approximately 30 mg/kg administered by i/v infusion on days 1, 5 and 9.

Group 1 (n=12): L1+A1 (humanised anti-IL-13 mAb, SEQ.I.D.NO:18 and SEQ.I.D.NO:22)

Group 2 (n=12): L1+A1 (humanised anti-IL-13 mAb, 30 mg/kg) and Pascolizumab (humanised anti-IL4 mAb, 30 mg/kg)

Group 3 (n=6): vehicle alone negative control treatment

The AHR readouts from phases 1 and 2 are calculated by taking pressure and airflow readings—lung resistance ($R_L$) and dynamic compliance ($C_{DYN}$) —in response to histamine, using the Buxco pulmonary mechanics system. The maximum percentage change from the baseline compared to post A.suum antigen challenge [for lung resistance ($R_L$) and dynamic compliance ($C_{DYN}$)] is compared for phases 1 and 2 i.e. with or without antibody treatment, and these data are used to assess the AHR phenotype.

In addition BAL samples are taken at days 1 and 11 in phases 1 and 2, to measure cellular infiltration and in particular eosinophilia. Serum samples are also taken to monitor IgE levels.

TABLE A

| Protein or polynucleotide (PN) description | Sequence identifier (SEQ.I.D.NO:) |
|---|---|
| 6A1, CDRH1 | 1 |
| 6A1, CDRH2 | 2 |
| 6A1, CDRH3 | 3 |
| 6A1, CDRL1 | 4 |
| 6A1, CDRL2 | 5 |
| 6A1, CDRL3 | 6 |
| 6A1, VH (murine) | 7 |
| 6A1, VL (murine) | 8 |
| hIL-13 | 9 |
| hIL-13 (PN) | 10 |
| 6A1, VH, humanised construct A1 | 11 |
| 6A1, VH, humanised construct A2 | 12 |
| 6A1, VH, humanised construct A3 | 13 |
| 6A1, VH, humanised construct A4 | 14 |
| 6A1, VL, humanised construct L1 | 15 |
| 6A1, VL, humanised construct L2 | 16 |
| 6A1, heavy chain, humanised construct A1 | 18 |
| 6A1, heavy chain, humanised construct A2 | 19 |
| 6A1, heavy chain, humanised construct A3 | 20 |
| 6A1, heavy chain, humanised construct A4 | 21 |
| 6A1, light chain, humanised construct L1 | 22 |
| 6A1, light chain, humanised construct L2 | 23 |
| 6A1, PN encoding SEQ.I.D.NO: 7 | 24 |
| 6A1, PN encoding SEQ.I.D.NO: 8 | 25 |
| 6A1, PN encoding SEQ.I.D.NO: 11 | 26 |

TABLE A-continued

| Protein or polynucleotide (PN) description | Sequence identifier (SEQ.I.D.NO:) |
|---|---|
| 6A1, PN encoding SEQ.I.D.NO: 12 | 27 |
| 6A1, PN encoding SEQ.I.D.NO: 13 | 28 |
| 6A1, PN encoding SEQ.I.D.NO: 14 | 29 |
| 6A1, PN encoding SEQ.I.D.NO: 15 | 30 |
| 6A1, PN encoding SEQ.I.D.NO: 16 | 31 |
| 6A1, PN encoding SEQ.I.D.NO: 18 | 32 |

TABLE A-continued

| Protein or polynucleotide (PN) description | Sequence identifier (SEQ.I.D.NO:) |
|---|---|
| 6A1, PN encoding SEQ.I.D.NO: 19 | 33 |
| 6A1, PN encoding SEQ.I.D.NO: 20 | 34 |
| 6A1, PN encoding SEQ.I.D.NO: 21 | 35 |
| 6A1, PN encoding SEQ.I.D.NO: 22 | 36 |
| 6A1, PN encoding SEQ.I.D.NO: 23 | 37 |

The invention claimed is:

1. An isolated therapeutic antibody or antigen binding fragment thereof that specifically binds hIL-13 and modulates the interaction between hIL-13 and hIL-13R which antibody or fragment thereof comprises the following CDRs:

| | |
|---|---|
| CDRH1: | SEQ ID NO:1 |
| CDRH2: | SEQ ID NO:2 |
| CDRH3: | SEQ ID NO:3 |
| CDRL1: | SEQ ID NO:4 |
| CDRL2: | SEQ ID NO:5 |
| CDRL3: | SEQ ID NO:6. |

2. The therapeutic antibody or antigen binding fragment of claim 1 wherein the antibody is an intact antibody.

3. The therapeutic antibody of claim 1 wherein the antibody is selected from a mouse antibody, a humanized antibody and a chimeric antibody.

4. The antibody of claim 2 wherein the antibody comprises a human constant region.

5. The antibody of claim 4 wherein the antibody comprises a constant region of IgG isotype.

6. The antibody of claim 5 wherein the antibody is selected from IgG1 and IgG4.

7. A mouse antibody of claim 3 comprising a VH domain of SEQ ID NO:7 and a VL domain of SEQ ID NO:8.

8. A humanized antibody of claim 3 comprising a VL domain of SEQ ID NO:15; and a VH domain selected from the group consisting of SEQ ID NO:11, SEQ ID NO:12, SEQ ID NO:13, and SEQ ID NO:14.

9. A humanized antibody of claim 3 comprising a VL domain of SEQ ID NO:16; and a VH domain selected from the group consisting of SEQ ID NO:11, SEQ ID NO:12, SEQ ID NO:13, and SEQ ID NO:14.

10. A humanized antibody of claim 3 further comprising a human constant region of a IgG isotype.

11. A humanized antibody comprising a light chain of SEQ ID NO:22; and a heavy chain selected from the group consisting of SEQ ID NO:18, SEQ ID NO:19, SEQ ID NO:20, and SEQ ID NO:21.

12. A humanized antibody comprising a light chain of SEQ ID NO:23; and a heavy chain selected from the group consisting of SEQ ID NO:18, SEQ ID NO:19, SEQ ID NO:20, and SEQ ID NO:21.

13. An antigen binding fragment of claim 1 wherein the fragment is a Fab, Fab', F(ab')$_2$, Fv, diabody, triabody, tetrabody, miniantibody, or minibody.

14. An antibody according to claim 4 comprising a mutated Fc region such that said antibody has reduced ADCC and/or complement activation.

15. A pharmaceutical composition comprising a therapeutic antibody or antigen binding fragment thereof of claim 1 and a pharmaceutically acceptable carrier.

16. A kit comprising the composition of claim 15.

17. The antibody or antigen binding fragment thereof of claim 1 wherein the antibody inhibits the binding between hIL-13 and hIL-13R.

18. The antibody or antigen binding fragment thereof of claim 17 wherein the antibody blocks the binding between hIL-13 and hIL-13R.

19. An isolated therapeutic antibody that specifically binds hIL-13 and modulates the interaction between hIL-13 and hIL-13R and has a dissociation constant $k_{off}$ in the range $1.4 \times 10^{-4}$ to $8.22 \times 10^{-5}$ s$^{-1}$ comprising CDRH1 of SEQ ID NO:1, CDRH2 of SEQ ID NO:2, CDRH3 of SEQ ID NO:3, CDRL1 of SEQ ID NO:4, CDRL2 of SEQ ID NO:5 and CDRL3 of SEQ ID NO:6.

20. The therapeutic antibody of claim 19 wherein the antibody is humanized.

21. A pharmaceutical composition comprising a first antibody of claim 1 and a second antibody wherein said second antibody is an anti-IL-4 antibody and a pharmaceutically acceptable carrier.

* * * * *